(12) United States Patent
Lorenz et al.

(10) Patent No.: US 6,410,483 B1
(45) Date of Patent: Jun. 25, 2002

(54) PHENYLSULFONYLUREAS, PROCESSES FOR THEIR PREPARATION, AND THEIR USE AS HERBICIDES AND PLANT GROWTH REGULATORS

(75) Inventors: Klaus Lorenz, Weiterstadt; Lothar Willms, Hofheim; Klaus Bauer, Hanau; Hermann Bieringer, Eppstein; Christopher Rosinger, Hofheim, all of (DE)

(73) Assignee: Hoechst Schering AgrEvo GmbH, Berlin (DE)

( * ) Notice: Subject to any disclaimer, the term of this patent is extended or adjusted under 35 U.S.C. 154(b) by 0 days.

(21) Appl. No.: 09/010,457

(22) Filed: Jan. 21, 1998

(30) Foreign Application Priority Data

Jan. 23, 1997 (DE) .......................................... 197 02 200

(51) Int. Cl.⁷ .................... C07D 239/69; C07D 403/12; A01N 43/54
(52) U.S. Cl. ........................ 504/215; 504/214; 544/122; 544/123; 544/295; 544/296; 544/321
(58) Field of Search ................................ 504/214, 215; 544/321, 295, 296, 122, 123

(56) References Cited

U.S. PATENT DOCUMENTS

| | | | | |
|---|---|---|---|---|
| 4,786,314 A | * | 11/1988 | Artz | 544/197 |
| 4,927,453 A | * | 5/1990 | Gee | 544/321 |
| 5,209,771 A | | 5/1993 | Meyer | 504/178 |
| 5,449,812 A | | 9/1995 | Schnabel | 560/13 |
| 5,648,315 A | | 7/1997 | Lorenz et al. | 504/214 |

FOREIGN PATENT DOCUMENTS

| | | |
|---|---|---|
| DE | 43 34 297 | 4/1995 |
| DE | 44 39 675 | 5/1996 |
| DE | 196 16 445 | 11/1997 |
| EP | 0496701 | 7/1992 |
| WO | WO 89/10921 | 11/1989 |
| WO | WO 94/10154 | 5/1994 |
| WO | WO 95/10507 | 4/1995 |
| ZA | 94/8063 | 8/1995 |
| ZA | 97/3549 | 3/1998 |

\* cited by examiner

*Primary Examiner*—John M. Ford
(74) *Attorney, Agent, or Firm*—Frommer Lawrence & Haug LLP

(57) ABSTRACT

Compounds of the formula (I) and salts thereof

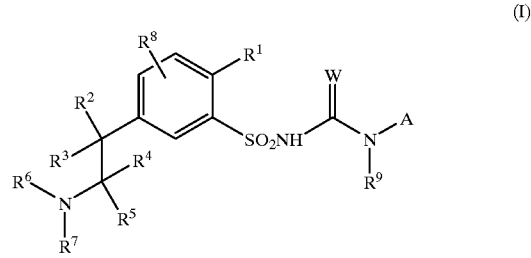

in which
R¹–R⁹, W and A are as defined in formula (I) of claim 1 are suitable as herbicides and plant growth regulators. They can be prepared by processes according to claim 5 via intermediates according to claim 9, some of which are novel.

10 Claims, No Drawings

PHENYLSULFONYLUREAS, PROCESSES FOR THEIR PREPARATION, AND THEIR USE AS HERBICIDES AND PLANT GROWTH REGULATORS

It is known that some phenylsulfonylureas have herbidical and plant-growth-regulating properties; cf. U.S. Pat. No. 4,786,314, U.S. Pat. No. 4,927,453, WO 89/10921 and WO 95/10507 (=ZA 94/8063). However, some of these show disadvantages upon use, such as, for example, high persistence or insufficient selectivity in important crops of useful plants.

There have now been found novel phenylsulfonylureas which have specific radicals on the phenyl ring and which can be employed advantageously as herbicides and plant growth regulators.

The present invention relates to compounds of the formula (I) or salts thereof

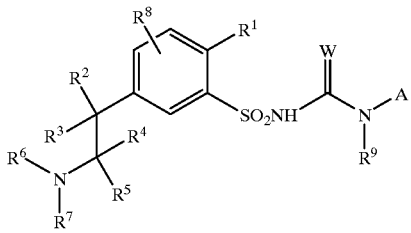

(I)

in which
- $R^1$ is an acyl radical of the formula $S(O)_n$—$R^{10}$ or CO—Q—$R^{11}$,
- $R^2$, $R^3$, $R^4$, $R^5$ are identical or different radicals selected from the group consisting of H, (1–6)alkyl, (1–4) alkoxy, (1–4)haloalkyl, (1–4)haloalkoxy and halogen,
- $R^6$ is H, OH, formyl, a radical of the formula R, R—O—, R—CO, R—O—CO—, R—SO$_2$—, R—SO— or RR$^0$NSO$_2$—, in which each of the radicals R and $R^0$ is a hydrocarbon radical which is unsubstituted or substituted and, inclusive of substituents, preferably has 1 to 20 carbon atoms,
- $R^7$ is an acyl radical or
- $NR^6R^7$ together are a heterocyclic radical which has 2 to 8 ring atoms and which, besides the nitrogen atom of the group $NR^6R^7$ as hetero ring atom, optionally has 1 to 3 further hetero ring atoms selected from the group consisting of N, O and S and which is unsubstituted or substituted and, inclusive of substituents, preferably has 2 to 18 carbon atoms and which has at least one electron-attracting group in neighboring position to the nitrogen atom of the group $NR^6R^7$,
- W is an oxygen or sulfur atom,
- $R^8$ is H, (1–6)alkyl, (2–6)alkenyl, (1–6)alkoxy, (1–4) alkylthio, [(1–4)alkyl]carbonyl or [(1–4)alkoxy] carbonyl, each of the six last-mentioned radicals being unsubstituted or substituted by one or more radicals selected from the group consisting of halogen, (1–4) alkoxy, (1–4)alkylthio and CN, or is halogen, NO$_2$, CN, NH$_2$ or mono- or disubstituted amino,
- $R^9$ is H or (1–6)alkyl,
- $R^{10}$ is NH$_2$, mono- or disubstituted amino or a hydrocarbon radical which is unsubstituted or substituted and which, inclusive of substituents, preferably has 1 to 30 carbon atoms,
- n is the number 0, 1 or 2, with the exception of the case $R^{10}$=NH$_2$ or mono- or disubstituted amino, in which case n=2,
- $R^{11}$ is H or a hydrocarbon radical which is unsubstituted or substituted and, inclusive of substituents, preferably has 1 to 30 C atoms, or is a heterocycle which has 3 to 8 ring atoms and which is unsubstituted or substituted and, inclusive of substituents, preferably has 1 to 20 carbon atoms,
- Q is an oxygen or sulfur atom or a group of the formula —NR'— in which R' is H or a hydrocarbon radical which is unsubstituted or substituted, or is an acyl radical in which R' is preferably H or has 1 to 10 carbon atoms,
- A is a radical of the formula

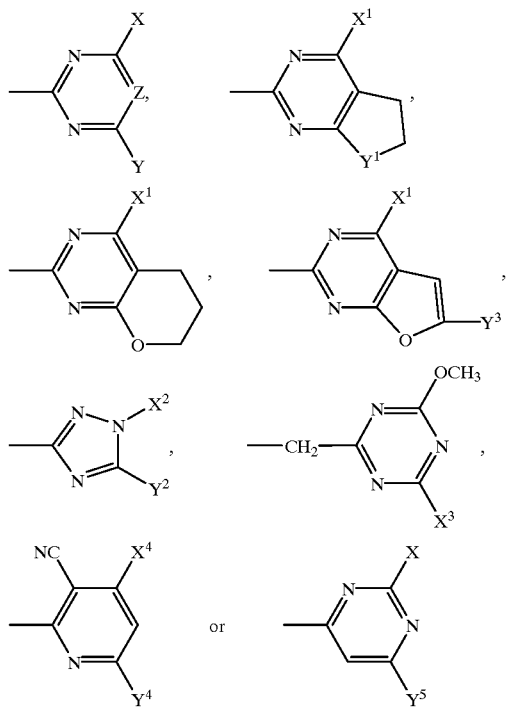

one of the radicals X and Y is hydrogen, halogen, (1–3)alkyl or (1–3)alkoxy, each of the two last-mentioned radicals being unsubstituted or substituted by one or more radicals selected from the group consisting of halogen, (1–3)alkoxy and (1–3) alkylthio, and the other of the radicals X and Y is hydrogen, halogen, (1–3)alkyl, (1–3)alkoxy or (1–3)alkylthio, each of the three last-mentioned alkyl-containing radicals being unsubstituted or substituted by one or more radicals selected from the group consisting of halogen, (1–3)alkoxy and (1–3)alkylthio, or is a radical of the formula $NR^aR^b$, (3–6)cycloalkyl, (2–4) alkenyl, (2–4)alkynyl, (3–4)alkenyloxy or (3–4) alkynyloxy, Z is CH or N,
$R^a$ and $R^b$ independently of one another are H, (1–4)alkyl or (2–4)alkenyl,
$X^1$ is CH$_3$, OCH$_3$, OC$_2$H$_5$ or OCHF$_2$,
$Y^1$ is —O— or —CH$_2$—,
$X^2$ is CH$_3$, C$_2$H$_5$ or CH$_2$CF$_3$,
$Y^2$ is OCH$_3$, OC$_2$H$_5$, SCH$_3$, SCH$_2$CH$_3$, CH$_3$ or C$_2$H$_5$,
$X^3$ is CH$_3$ or OCH$_3$,
$Y^3$ is H or CH$_3$, X⁴ is CH₃, OCH₃, OC₂H₅, CH₂OCH₃ or Cl,
Y⁴ is CH₃, OCH₃, OC₂H₅ or Cl and
Y⁵ is CH₃, C₂H₅, OCH₃ or Cl.

Of greater interest are those compounds of the formula (I) according to the invention and salts thereof in which $R^1$ is $S(O)_n-R^{10}$ or $COQR^{11}$, $R^2$, $R^3$, $R^4$, $R^5$ independently of one another are H or (1–4)alkyl, $R^6$ is H, OH, formyl, (1–6)alkyl, (2–6)alkenyl, (2–4)alkynyl, (1–6)alkoxy, (2–6)alkenyloxy, (2–6)alkynyloxy, [(1–6)alkyl]carbonyl, [(2–6)alkenyl]carbonyl, [(2–6)alkynyl]carbonyl), (1–4)alkylsulfonyl, (2–6)alkenylsulfonyl, (2–6)alkynylsulfonyl, (3–6)cycloalkyl, (5–6)cycloalkenyl, [(3–6)cycloalkyl]carbonyl, [(5–6)cycloalkenyl]carbonyl, [(3–6)cycloalkyl]sulfonyl, [(5–6)cycloalkenyl]sulfonyl, each of the 18 last-mentioned radicals being unsubstituted or substituted by one or more radicals selected from the group consisting of halogen, (1–4)alkoxy, (1–4)alkylthio, (1–4)alkylsulfinyl, (1–4)alkylsulfonyl, [(1–4)alkoxy]carbonyl, [(1–4)alkyl]carbonyl, [(1–4)alkyl]carbonyloxy and CN and, in the case of cyclic radicals, also by (1–4)alkyl and (1–4)haloalkyl, or phenylcarbonyl or phenylsulfonyl, each of the two last-mentioned radicals being unsubstituted or substituted in the phenyl ring by one or more radicals selected from the group consisting of halogen, CN, NO₂, (1–4)alkyl, (1–4)haloalkyl, (1–4)alkoxy and (1–4)haloalkoxy, $R^7$ is CHO, [(1–6)alkyl]carbonyl, [(2–6)alkenyl]carbonyl, [(2–6)alkynyl]carbonyl, (1–6)alkylsulfonyl, (2–6)alkenylsulfonyl, (2–6)alkynylsulfonyl, [(3–6)cycloalkyl]carbonyl, [(5–6)cycloalkenyl]carbonyl, [(3–6)cycloalkyl]sulfonyl, (5–6)cycloalkenylsulfonyl, each of the 10 last-mentioned radicals being unsubstituted or substituted by one or more radicals selected from the group consisting of halogen, (1–4)alkoxy, (1–4)alkylthio, (1–4)alkylsulfonyl, (1–4)alkylsulfinyl, (1–4)alkylcarbonyl, [(1–4)alkoxy]-carbonyl, [(1–4)alkyl]carbonyloxy and CN and, in the case of cyclic radicals, also by (1–4)alkyl and (1–4)haloalkyl, or phenylcarbonyl or phenylsulfonyl, each of the two last-mentioned radicals being unsubstituted or substituted in the phenyl ring by one or more radicals selected from the group consisting of halogen, CN, NO₂, (1–4)alkyl, (1–4)haloalkyl, (1–4)alkoxy and (1–4)haloalkoxy, or mono- or di[(1–4)alkyl]aminosulfonyl which is unsubstituted or substituted in the alkyl moiety by one or more radicals selected from the group consisting of halogen, (1–4)alkoxy, (1–4)alkylthio, (1–4)alkylsulfinyl, (1–4)alkylsulfonyl, [(1–4)alkyl]carbonyl, [(1–4)alkyl]carbonyloxy, [(1–4)alkoxy]carbonyl and CN, or a group of the formula COCOR' in which R'=H, OH, (1–4)alkoxy or (1–4)alkyl, or a group of the formula

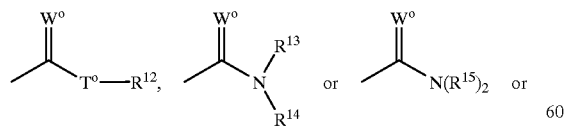

$R^6$ and $R^7$ together are a chain of the formula $(-CH_2)_{m1}B^1-$ or $-B^1-(CH_2)_{m2}B^2-$, the chain being unsubstituted or substituted by one or more (1–3)alkyl radicals or halogen and m1 is 3, 4 or 5 and m2 is 2, 3 or 4, and W, W° are an oxygen atom or a sulfur atom,
$B^1$, $B^2$ independently of one another are $SO_2$ or CO,
Q is O, S or $NR^{16}$,
T° is an oxygen atom or a sulfur atom, $R^8$ is H, (1–4)alkyl, (1–4)alkoxy, (1–4)alkylthio, [(1–4)alkyl]carbonyl or [(1–4)alkoxy]carbonyl, each of the last-mentioned 5 radicals being unsubstituted or substituted in the alkyl moiety by one or more halogen atoms, or is halogen, NO₂, CN or mono- or di(1–4)alkylamino, $R^9$ is H or CH₃, $R^{10}$ is $NR^{17}R^{18}$, (1–6)alkyl, (2–6)alkenyl, (2–6)alkynyl, (3–6)cycloalkyl, (5–6)cycloalkenyl or phenyl, each of the last-mentioned 6 radicals being unsubstituted or substituted by one or more radicals selected from the group consisting of halogen, CN, (1–4)alkoxy, (1–4)alkylthio, (1–4)alkylsulfinyl, (1–4)alkylsulfonyl, [(1–4)alkyl]carbonyl, [(1–4)alkoxy]carbonyl and [(1–4)alkyl]carbonyloxy, n is the number 0, 1 or 2, unless $R^{10}=NR^{17}R^{18}$, in which case n=2, and $R^{11}$ is H, (1–6)alkyl, (2–6)alkenyl, (2–6)alkynyl, (3–6)cycloalkyl, (5–6)cycloalkenyl or phenyl, each of the last-mentioned 6 radicals being unsubstituted or substituted by one or more radicals selected from the group consisting of halogen, CN, (1–4)alkoxy, (1–4)alkylthio, (1–4)alkylsulfinyl, (1–4)alkylsulfonyl, [(1–4)alkyl]carbonyl, [(1–4)alkoxy]carbonyl and [(1–4)alkyl]carbonyloxy, and, in the case of cyclic radicals, also by (1–4)alkyl and (1–4)haloalkyl, or is a radical of the heterocyclyl or heterocyclyl(1–4)alkyl type which has 3–7 ring atoms, preferably having 1 to 3 hetero ring atoms selected from the group consisting of N, O and S, in particular a radical of the formula A-1 to A-6,

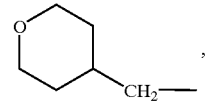
A-1

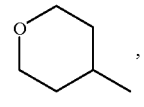
A-2

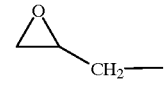
A-3

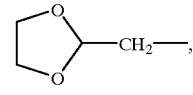
A-4

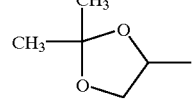
A-5

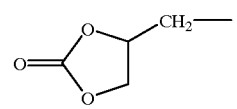
A-6

$R^{12}$ is (1–4)alkyl, (3–4)alkenyl or (3–4)alkynyl, each of the three last-mentioned radicals being unsubstituted or substituted by one or more radicals selected from the group consisting of halogen, (1–4)alkoxy, (1–4) alkylthio, [(1–4)alkyl]carbonyl and [(1–4)alkoxy] carbonyl, $R^{13}$, $R^{14}$ independently of one another are H, (1–4) alkyl, (3–4)alkenyl oder (3–4)alkynyl, each of the three last-mentioned radicals being unsubstituted or substituted by one or more of the radicals selected from the group consisting of halogen, (1–4)alkoxy, (1–4)alkylthio, [(1–4)alkyl]carbonyl and [(1–4) alkoxy]carbonyl, the radicals $R^{15}$ together with the nitrogen atom are a heterocyclic ring which has 5 or 6 ring members, may contain further hetero atoms selected from the group consisting of N, O and S at the oxidation levels which are possible and which is unsubstituted or substituted by (1–4)alkyl or the oxo group, or which is benzo-fused, $R^{16}$ is H, (1–4)alkyl, (3–4)alkenyl or (3–4)alkynyl, each of the three last-mentioned radicals being unsubstituted or substituted by one or more radicals selected from the group consisting of halogen, (1–4)alkoxy and (1–4) alkylthio, $R^{17}$ is H, (1–4)alkyl or (1–4)alkoxy, and $R^{18}$ is H or (1–4)alkyl.

Definitions of general radicals with carbon atoms in formula (I) frequently contain ranges or individual data for the number of carbon atoms possible. The indication of a range, or number, of the carbon atoms precedes the name of the general chemical group in brackets; for example, (1–4) alkyl denotes an alkyl radical having 1 to 4 carbon atoms; or (1–4)haloalkyl denotes haloalkyl having 1 to 4 carbon atoms in the alkyl moiety or alkyl skeleton; (1)alkyl equals methyl; the general definition of unsubstituted (3)alkyl thus embraces n-propyl and i-propyl.

The compounds of the formula (I) may form salts where the hydrogen of the —SO$_2$—NH— group is replaced by a cation which is suitable for agriculture. Examples of these salts are metal salts, in particular alkali metal salts or alkaline earth metal salts, in particular sodium salts and potassium salts, or else ammonium salts or salts with organic amines. Equally, salt formation may be effected by subjecting an acid to an addition reaction with basic groups, such as, for example, amino and alkylamino. Acids which are suitable for this purpose are strong inorganic and organic acids, for example HCl, HBr, H$_2$SO$_4$ or HNO$_3$.

In formula (I) and all subsequent formulae, the radicals alkyl, alkoxy, haloalkyl, haloalkoxy, alkylamino and alkylthio and the corresponding unsaturated and/or substituted radicals in the carbon skeleton may in each case be straight-chain or branched. Unless specifically indicated, the lower carbon skeletons, e.g. those having 1 to 6 carbon atoms, or, in the case of unsaturated groups, those having 2 to 6 carbon atoms, are preferred amongst these radicals. Alkyl radicals, also in the composite meanings such as alkoxy, haloalkyl and the like, are, for example, methyl, ethyl, n- or i-propyl, n-, i-, t- or 2-butyl, pentyl radicals, hexyl radicals, such as n-hexyl, i-hexyl and 1,3-dimethylbutyl, heptyl radicals such as n-heptyl, 1-methylhexyl and 1,4-dimethylpentyl; alkenyl and alkynyl radicals have the meanings of the unsaturated radicals which are possible and which correspond to the alkyl radicals; alkenyl is, for example, allyl, 1-methylprop-2-en-1-yl, 2-methylprop-2-en-1-yl, but-2-en-1-yl, but-3-en-1-yl, 1-methylbut-3-en-1-yl and 1-methylbut-2-en-1-yl; alkynyl is, for example, propargyl, but-2-yn-1-yl, but-3-yn-1-yl, 1-methylbut-3-yn-1-yl.

Cycloalkyl is a carbocyclic saturated ring system, for example one having 3–8 carbon atoms, for example cyclopropyl, cyclopentyl or cyclohexyl.

Alkenyl in the form "(3–4)alkenyl" or "(3–6)alkenyl" is, preferably, an alkenyl radical having 3 to 4, or 3 to 6, carbon atoms where the double bond is not on the carbon atom which is linked to the remaining moiety of the compound (I) ("yl" position). The same applies analogously to (3–4) alkynyl and the like.

Halogen is, for example, fluorine, chlorine, bromine or iodine. Haloalkyl, -alkenyl and -alkynyl are alkyl, alkenyl and alkynyl, respectively, which are partially or fully substituted by halogen, preferably by fluorine, chlorine and/or bromine, in particular by fluorine or chlorine; for example CF$_3$, CHF$_2$, CH$_2$F, CF$_3$CF$_2$, CH$_2$FCHCl, CCl$_3$, CHCl$_2$, CH$_2$CH$_2$Cl; haloalkoxy is, for example, OCF$_3$, OCHF$_2$, OCH$_2$F, CF$_3$CF$_2$O, OCH$_2$CF$_3$ and OCH$_2$CH$_2$Cl; the same applies analogously to haloalkenyl and other halogen-substituted radicals.

A hydrocarbon radical is a straight-chain, branched or cyclic and saturated or unsaturated aliphatic or aromatic hydrocarbon radical, for example alkyl, alkenyl, alkynyl, cycloalkyl, cycloalkenyl or aryl; aryl is a mono-, bi- or polycyclic aromatic system, for example phenyl, naphthyl, tetrahydronaphthyl, indenyl, indanyl, pentalenyl, fluorenyl and the like, preferably phenyl; a hydrocarbon radical is preferably alkyl, alkenyl or alkynyl having up to 12 carbon atoms or cycloalkyl having 3, 4, 5, 6 or 7 ring atoms or phenyl; the same applies analogously to a hydrocarbon radical in a hydrocarbon-oxy radical.

A heterocyclic radical or ring (heterocyclyl) can be saturated, unsaturated or heteroaromatic; preferably it has one or more hetero atoms in the ring, preferably selected from the group consisting of N, O and S; preferably it is an aliphatic heterocyclyl radical having 3 to 7 ring atoms or a heteroaromatic radical having 5 or 6 ring atoms, and has 1, 2 or 3 hetero atoms. The heterocyclic radical may be, for example, a heteroaromatic radical or ring (heteroaryl), such as, for example, a mono-, bi- or polycyclic aromatic system in which at least 1 ring has one or more hetero atoms, for example pyridyl, pyrimidinyl, pyridazinyl, pyrazinyl, thienyl, thiazolyl, oxazolyl, furyl, pyrrolyl, pyrazolyl and imidazolyl, or it is a partially or fully hydrogenated radical such as oxiranyl, pyrrolidyl, piperidyl, piperazinyl, dioxolanyl, morpholinyl, tetrahydrofuryl. Suitable substituents for a substituted heterocyclic radical are the substituents mentioned further below, and additionally also oxo. The oxo group may also occur on the hetero ring atoms which may exist at various oxidation levels, for example in the case of N and S.

Substituted radicals, such as substituted hydrocarbon radicals, for example substituted alkyl, alkenyl, alkynyl, aryl, phenyl and benzyl, or substituted heterocyclyl or heteroaryl, are, for example, a substituted radical which is derived from the unsubstituted skeleton, the substituents being, for example, one or more, preferably 1, 2 or 3, radicals selected from the group consisting of halogen, alkoxy, haloalkoxy, alkylthio, hydroxyl, amino, nitro, carboxyl, cyano, azido, alkoxycarbonyl, alkylcarbonyl, formyl, carbamoyl, mono- and dialkylaminocarbonyl, substituted amino such as acylamino, mono- and dialkylamino, and alkylsulfinyl, haloalkylsulfinyl, alkylsulfonyl, haloalkylsulfonyl and, in the case of cyclic radicals, also alkyl and haloalkyl, and also unsaturated aliphatic radicals which correspond to the abovementioned saturated hydrocarbon-containing radicals, such as alkenyl, alkynyl, alkenyloxy, alkynyloxy and the like. Amongst the radicals having carbon atoms, those having 1 to 4 carbon atoms, in particular 1 or 2 carbon atoms, are preferred. As a rule, preferred substituents are those selected from the group consisting of halogen, for example fluorine and chlorine, (1–4)alkyl, preferably methyl or ethyl, (1–4)haloalkyl, preferably trifluormethyl, (1–4)alkoxy, preferably methoxy or ethoxy, (1–4)haloalkoxy, nitro and cyano. Especially preferred are the substituents mothyl, mothoxy and chlorine.

Mono- or disubstituted amino means a chemically stable radical selected from the group of the substituted amino radicals which are N-substituted, for example, by one or two identical or different radicals selected from the group consisting of alkyl, alkoxy, acyl and aryl; preferably monoalkylamino, dialkylamino, acylamino, arylamino, N-alkyl-N-arylamino and also N-heterocycles; alkyl radicals having 1 to 4 carbon atoms are preferred; aryl is, preferably, phenyl or substituted phenyl; the definition mentioned further below applies to acyl, preferably (1–4)alkanoyl. The same applies analogously to substituted hydroxylamino or hydrazino.

Optionally substituted phenyl is, preferably, phenyl which is unsubstituted or mono- or polysubstituted, preferably up to trisubstituted, by identical or different radicals selected from the group consisting of halogen, (1–4)alkyl, (1–4)alkoxy, (1–4)halogenoalkyl, (1–4)halogenoalkoxy and nitro, for example o-, m- and p-tolyl, dimethylphenyl radicals, 2-, 3- and 4-chlorophenyl, 2-, 3- and 4-trifluoro- and -trichlorophenyl, 2,4-, 3,5-, 2,5- and 2,3-dichlorophenyl, o-, m- and p-methoxyphenyl.

An acyl radical is the radical of an organic acid, for example the radical of a carboxylic acid, and radicals of acids derived therefrom, such as of thiocarboxylic acid, optionally N-substituted iminocarboxylic acids, or the radical of carbonic monoesters, of optionally N-substituted carbamic acid, sulfonic acids, sulfinic acids, phosphonic acids and phosphinic acids. Acyl is, for example, formyl, alkylcarbonyl such as [(1–4)alkyl]carbonyl, phenylcarbonyl, it being possible for the phenyl ring to be substituted, for example as shown above for phenyl, or alkyloxycarbonyl, phenyloxycarbonyl, benzyloxycarbonyl, alkylsulfonyl, alkylsulfinyl, N-alkyl-1-iminoalkyl and other radicals of organic acids.

The invention also relates to all stereoisomers which the formula (I) embraces, and mixtures of these. Such compounds of the formula (I) have one or more asymmetric carbon atoms, or else double bonds which are not indicated specifically in formula (I). Possible stereoisomers which are defined by their specific spatial form, such as enantiomers, diastereomers and Z- and E-isomers, are all embraced by formula (I) and can be obtained by customary methods from stereoisomer mixtures, or else be prepared by stereoselective reactions in combination with the use of stereochemically pure starting materials.

The above examples of radicals or ranges of radicals which come under the general terms such as "alkyl", "acyl", "substituted radicals" and the like, are no complete enumeration. In particular, the general terms also embrace the definitions mentioned further below of ranges of radicals in groups of preferred compounds, in particular ranges of radicals which embrace specific radicals from the tabulated examples.

Compounds of the formula (I) according to the invention or salts thereof which are of particular interest, mainly for reasons of more potent herbicidal action, better selectivity and/or greater ease of preparation are those in which $R^1$ is $S(O)_n$—$R^{10}$ or CO—$OR^{11}$, n is the number 0, 1 or 2, with the exception of the case $R^{10}$=$NR^{17}R^{18}$, in which case n=2, $R^6$ is H or (1–4)alkyl which is unsubstituted or substituted by one or more halogen atoms or by one or more radicals selected from the group (1–4)alkoxy and (1–4)alkylthio, $R^7$ is formyl, [(1–6)alkyl]carbonyl, [(2–4)alkenyl]carbonyl, [(2–4)alkynyl]carbonyl, [(3–6)cycloalkyl]carbonyl or (1–6)alkylsulfonyl, each of the 5 last-mentioned radicals being unsubstituted or substituted by one or more radicals selected from the group consisting of halogen, (1–4)alkoxy, (1–4)alkylthio, (1–4)alkylsulfonyl, [(1–4)alkyl]carbonyl, [(1–4)alkoxyl]carbonyl, [(1–4)alkyl]carbonyloxy and CN and, in the case of cyclic radicals, also (1–4)alkyl and (1–4)haloalkyl, or phenylcarbonyl or phenylsulfonyl, each of the two last-mentioned radicals being unsubstituted or substituted by one or more radicals selected from the group consisting of halogen, CN, $SO_2$, (1–4)alkyl, (1–4)haloalkyl, (1–4)alkoxy and C1–4)haloalkoxy, or mono- or di[(1–4)-alkyl]aminosulfonyl, or a group of the formula —CO—CO—R' in which R' is (1–4)alkoxy, or a group of the formula —$CW^\circ$—$R^{12}$, —$CW^\circ$—$NR^{13}R^{14}$ or —$CW^\circ$—$N(R^{15})_2$ or $R^6$, $R^7$ together are a chain of the formula (—$CH_2$)$_{m1}$$B^1$— or —$B^1$—(CH_2)$_{m2}$$B^2$—, m1 being 3, 4 or 5 and m2 being 2, 3 or 4, and W, $W^\circ$ in each case independently are an oxygen or sulfur atom, $T^\circ$ is an oxygen or sulfur atom, $B^1$ is $SO_2$ or CO, $B^2$ is $SO_2$ or CO, Q is O, S or $NR^{16}$, $R^8$ is a hydrogen atom, $R^9$ is H or $CH_3$, $R^{10}$ is $NR^{17}R^{18}$, (1–6)alkyl or (3–6)cycloalkyl, $R^{11}$ is H, (1–6)alkyl, (3–6)cycloalkyl or a radical of the formulae A-1 to A-6,

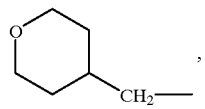

A-1

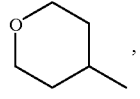

A-2

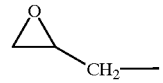

A-3

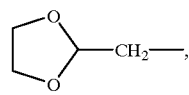

A-4

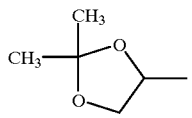

A-5

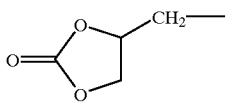

A-6

$R^{12}$ is (1–4)alkyl or (1–4)haloalkyl, $R^{13}$, $R^{14}$ independently of one another are H or (1–4) alkyl, the radicals $R^{15}$ together are a divalent chain of the formula —(CH$_2$)$_{m3}$— in which m3 is 3, 4 or 5, or of the formula —CH$_2$CH$_2$—O—CH$_2$CH$_2$—, $R^{16}$ is H or (1–4)alkyl, $R^{17}$ is H or (1–4)alkyl and $R^{18}$ is H or (1–4)alkyl.

Preferred compounds of the formula (I) according to the invention and salts thereof are those in which $R^6$ is H or (1–4)alkyl, $R^7$ is CHO, [(1–6)alkyl]carbonyl, [(1–4)haloalkyl]carbonyl, [(1–4)alkoxy-(1–4)alkyl]carbonyl, [(3–6)cycloalkyl]carbonyl, phenylcarbonyl which is unsubstituted or substituted by one or more radicals selected from the group consisting of halogen, CN, NO$_2$, (1–4)alkyl, (1–4)haloalkyl, (1–4)alkoxy and (1–4)haloalkoxy, or is phenylsulfonyl which is unsubstituted or substituted by one or more radicals selected from the group consisting of (1–4)alkyl and (1–4)alkoxy, or is mono- or di[(1–4)alkyl]aminosulfonyl, (1–6)alkylsulfonyl, (1–4)haloalkylsulfonyl or a group of the formula —CW$^o$—R$^{12}$ or —CW$^o$—NR$^{13}$R$^{14}$ W, W$^o$ independently of one another are in each case O or S, T$^o$ is O or S, Q is O, S or NR$^{16}$, $R^{10}$ is NR$^{17}$R$^{18}$, (1–4)alkyl or (3–6)cycloalkyl, $R^{11}$ is H or (1–4)alkyl, $R^{12}$ is (1–4)alkyl, $R^{13}$, $R^{14}$ independently of one another are H or (1–4) alkyl, $R^{16}$ is H or (1–3)alkyl, $R^{17}$ is (1–4)alkyl and $R^{18}$ is H or (1–4)alkyl.

Other preferred compounds of the formula (I) according to the invention or salts thereof are those which contain a combination of radicals of the abovementioned compounds of particular interest or of the preferred compounds, and those which contain individual or several radicals from amongst the compounds listed in Table 1 or 2 (see below).

The present invention also relates to processes for the preparation of the compounds of the formula (I) or salts thereof, which comprise a) reacting a compound of the formula (II)

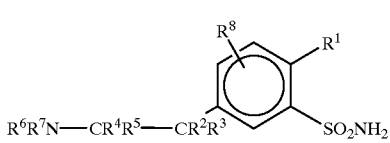

(II)

with a heterocyclic carbamate of the formula (III)

  (III)

in which R* is optionally substituted phenyl or (C$_1$–C$_4$)alkyl, or b) reacting an arylsulfonylcarbamate of the formula (IV)

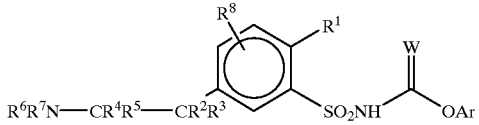

(IV)

in which Ar is an aryl radical, preferably an optionally substituted phenyl, with an amino heterocycle of the formula (V)

  (V), or c) reacting a sulfonyl isocyanate of the formula (VI)

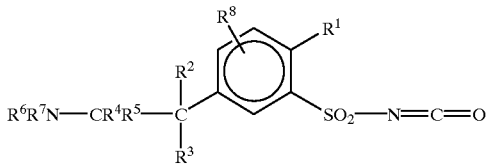

(VI)

with an amino heterocycle of the formula H—NR$^9$—A (V), or d) first reacting, in a one-pot reaction, an amino heterocycle of the formula H—NR$^9$—A (V) with phosgene in the presence of a base and reacting the intermediate formed with a phenylsulfonamide of the formula (II), or e) reacting a sulfonyl chloride of the formula (VII)

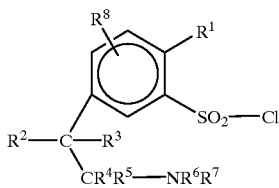

(VII)

with a cyanate M—OCN in which M=a cation, for example NH$_4$, Na or K, and with an amino heterocycle of the formula H—NR$^9$—A (V) in the presence of a base, or f) reacting a sulfonamide of the abovementioned formula (II) with a (thio)isocyanate of the formula (V')

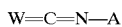  (V')

in the presence of a base, where, in formulae (II)–(VII) and (V'), the radicals or symbols $R^1$–$R^9$, A, W and n are as defined in formula (I) and where, in variants a) and c)–e), the initial products are compounds of the formula (I) where W=O.

The reaction of the compounds of the formulae (II) and (III) is preferably carried out with base catalysis in an inert organic solvent such as, for example, dichloromethane, acetonitrile, dioxane or THF, at temperatures between 0° C.

and the boiling point of the solvent. Bases which are used for this purpose are, for example, organic amine bases such as 1,8-diazabicyclo[5.4.0]undec-7-ene (DBU), in particular when R*=(substituted) phenyl (cf. EP-A-44807), or trimethylaluminum or triethylaluminum, the latter two substances in particular when R*=alkyl (cf. EP-A-166516).

The sulfonamides (II) are novel compounds. They and their preparation are also subject of the present invention.

With reference to the compounds (II) where $R^2$ to $R^5$=H and $R^1$=COQR$^{11}$ where Q=O, the following text will illustrate in greater detail possible preparation methods which, when modified slightly, may also be employed for compounds where $R^2$–$R^5$ are other than hydrogen or where $R^1$ is as described above.

Starting from optionally substituted benzyl halides (VIII) (see Diagram 1; cf. WO 95/10507), benzyl cyanide (IX) may be obtained by nucleophilic exchange of the halide for cyanide. After reduction or hydrogenolysis of (IX) and, if appropriate, subsequent functionalization of the amino group, for example by alkylation, phenethylamines (X) or phenethylamines (XI) are obtained in which $R^1$=COR$^{11}$, $R^2$=$R^3$=$R^4$=$R^5$=$R^7$=H and which, if appropriate after further functionalization, for example by acylation or by eliminating the tert-butyl group, are reacted in analogy to known processes (for example with CF$_3$COOH) to give the sulfonamides (II') (see Diagram 1).

Diagram 1

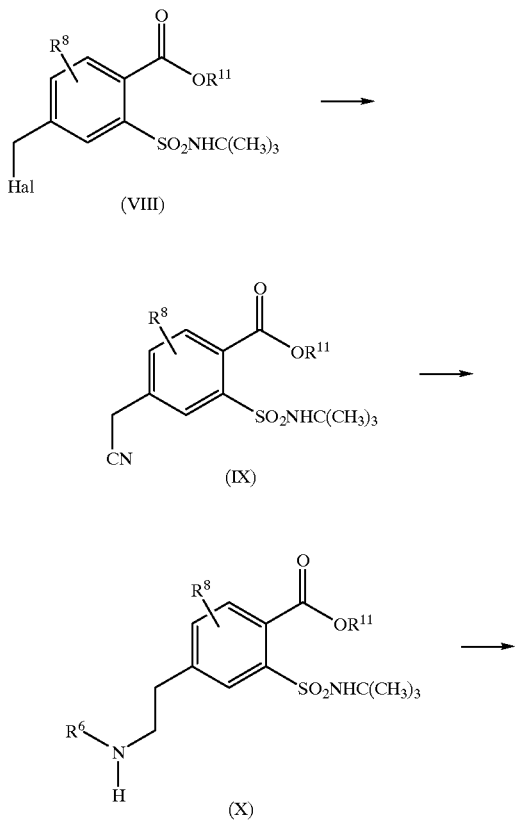

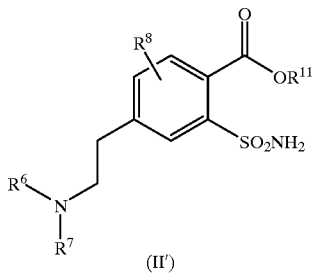

The procedure may also be employed analogously for the preparation of other compounds of the formula (II), the compound of the formula (XI)

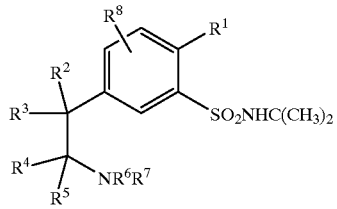

being employed in the last step.

The carbamates of the formula (II) can be prepared by methods described in the South African Patent Applications 82/5671 and 82/5045, and EP-A-70804 (U.S. Pat. No. 4,480,101) or RD 275056.

The reaction of the compounds (IV) with the amino heterocycles (V) is preferably carried out in inert aprotic solvents such as, for example, dioxane, acetonitrile or tetrahydrofuran at temperatures between 0° C. and the boiling point of the solvent. The starting materials (V) required are known from the literature or can be prepared by processes known from the literature. The arylsulfonylcarbamates of the formula (IV) are obtained analogously to U.S. Pat. No. 4,684,393 or U.S. Pat. No. 4,743,290.

The aryl- or phenylsulfonyl isocyanates of the formula (VI) can be prepared analogously to U.S. Pat. No. 4,481,029 and reacted with the amino heterocycles (V).

The phosgenation of compounds of the formula (V) in accordance with variant d) can preferably be carried out in the presence of bases, such as sterically hindered organic amine bases, for example triethylamine. The subsequent reaction with compounds of the formula (II) in accordance with variant d) can be carried out in analogy to known processes (cf. EP-A-232 067).

The sulfochlorides (VII) can be obtained from corresponding sulfonic acids, for example by standard methods such as reacting the potassium salt with phosphorus oxychloride or thionyl chloride in inert solvents such as acetonitrile and/or sulfolane or in substance by refluxing (cf. Houben-Weyl-Klamann, "Methoden der organischen Chemie" [Methods in Organic Chemistry], 4th Ed. Vol 3 XI/2, pp. 1067–1073, Thieme Verlag Stuttgart, 1985).

The corresponding sulfonic acids are obtainable from corresponding nitro compounds in analogy to the reaction of compounds (XI).

Alternatively, sulfochlorides (VII) can be obtained in individual cases by sulfonating (+chlorinating) or sulfochlorinating suitable substituted benzoic esters; sulfochlorination in analogy to Houben-Weyl-Klamann, "Methoden der organischen Chemie" [Methods in Organic Chemistry], 4th Ed. Vol. E XI/2, p. 1067 et seq., Thieme Verlag Stuttgart, 1985; Houben-Weyl-Müller, "Methoden der organischen Chemie" [Methods in Organic Chemistry], 4th Ed. Vol. IX, p. 563 et seq., Thieme Verlag Stuttgart, 1955; sulfonation in analogy to Houben-Weyl-Klamann, "Methoden der organischen Chemie" [Methods in Organic Chemistry], 4th PEd. Vol. E XI/2, p 1055 et seq., Thieme Verlag Stuttgart, 1985; Houben-Weyl-Müller, "Methoden der organischen Chemie" [Methods in Organic Chemistry], 4th Ed. Vol. IX, p. 435 et seq., Thieme Verlag Stuttgart, 1955.

The (thio)isocyanates of the formula (V') can be obtained by processes known from the literature (EP-A-232067, EP-A-166516). The reaction of the (thio)isocyanates (V') with compounds (II) is carried out, for example, at −10° C. to 100° C., preferably 20 to 100° C., in an inert aprotic solvent such as, for example, acetone or acetonitrile, in the presence of a suitable base, for example $N(C_2H_5)_3$ or $K_2CO_3$.

The salts of the compounds of the formula (I) are preferably prepared in inert polar solvents such as, for example, water, methanol or acetone at temperatures from 0–100° C. Bases which are suitable for the preparation of the salts according to the invention are, for example, alkali metal carbonates such as potassium carbonate, alkali metal hydroxides and alkaline earth metal hydroxides, eg. NaOH or KOH, or ammonia or ethanolamine.

The term "inert solvents" used in the above process variants is to be understood as meaning in each case solvents which are inert under the reaction conditions in question, but which need not be inert under all reaction conditions.

The compounds of the formula (I) according to the invention have an outstanding herbicidal activity against a broad spectrum of economically important monocotyledonous and dicotyledonous harmful plants. The active ingredients also act efficiently on perennial weeds which produce shoots from rhizomes, root stocks or other perennial organs and which are difficult to control. In this context, it is immaterial whether the substances are applied pre-sowing, pre-emergence or post-emergence.

Specifically, examples may be mentioned of some representatives of the monocotyledonous and dicotyledonous weed flora which can be controlled by the compounds according to the invention, without these being a restriction to certain species.

Examples of weed species on which the active ingredient acts efficiently are, from amongst the monocotyledons, Avena, Lolium, Alopecurus, Phalaris, Echinochloa, Digitaria, Setaria and also Cyperus species from the annual sector and from amongst the perennial species Agropyron, Cynodon, Imperata and Sorghum, and also perennial Cyperus species.

In the case of the dicotyledonous weed species, the spectrum of action extends to species such as, for example, Galium, Viola, Veronica, Lamium, Stellaria, Amaranthus, Sinapis, lpomoea, Matricaria, Abutilon and Sida from amongst the annuals, and Convolvulus, Cirsium, Rumex and Artemisia in the case of the perennial weeds.

The active ingredients according to the invention also effect outstanding control of weeds which occur under the specific conditions of rice growing such as, for example, Sagittaria, Alisma, Eleocharis, Scirpus and Cyperus.

If the compounds according to the invention are applied to the soil surface prior to germination, then the weed seedlings are either prevented completely from emerging, or the weeds grow until they have reached the cotyledon stage but then their growth stops, and, eventually, after three to four weeks have elapsed, they die completely.

If the active ingredient is applied post-emergence to the green parts of the plants, growth also stops drastically a very short time after the treatment and the weed plants remain at the developmental stage of the point in time of application, or they die completely after a certain time, so that in this manner competition by the weeds, which is harmful to the crop plants, is eliminated at a very early point in time and in a sustained manner.

Although the compounds according to the invention have an excellent herbicidal activity against monocotyledonous and dicotyledenous weeds, crop plants of economically important crops such as, for example, wheat, barley, rye, rice, maize, sugar beet, cotton and soya, are not damaged at all, or only to a negligible extent. For these reasons, the present compounds are highly suitable for selectively controlling undesired plant growth in plantings for agricultural use.

In addition, the substances according to the invention have excellent growth-regulating properties in crop plants. They engage in the plant metabolism in a regulating manner and can thus be employed for the targeted control of plant constituents and for facilitating harvesting, such as, for example, by provoking desiccation and stunted growth. Furthermore, they are also suitable for generally regulating and inhibiting undesired vegetative growth, without destroying the plants in the process. Inhibition of vegetative growth plays an important role in many monocotyledonous and dicotyledenous crops since lodging can be reduced hereby, or prevented completely.

The compounds according to the invention can be employed in the conventional preparations in the form of wettable powders, emulsifiable concentrates, sprayable solutions, dusts or granules. Another subject of the invention are therefore also herbicidal and plant-growth-regulating compositions which comprise the compounds of the formula (I).

The compounds of the formula (I) can be formulated in various ways, depending on the prevailing biological and/or chemico-physico parameters. Examples of possible formulations which are suitable are: wettable powders (WP), water-soluble powders (SP), water-soluble concentrates, emulsifiable concentrates (EC), emulsions (EW) such as oil-in-water and water-in-oil emulsions, sprayable solutions, suspension concentrates (SC), oil- or water-based dispersions, solutions which are miscible with oil, capsule suspensions (CS), dusts (DP), seed-dressing products, granules for broadcasting and soil application, granules (GR) in the form of microgranules, spray granules, coated granules and adsorption granules, water-dispersible granules (WG), water-soluble granules (SG), ULV formulations, microcapsules and waxes.

These individual formulation types are known in principle and are described, for example, in: Winnacker-Küchler, "Chemische Technologie" [Chemical Technology], Volume 7, C. Hauser Verlag Munich, 4th Ed. 1986, Wade van Valkenburg, "Pesticide Formulations", Marcel Dekker, N.Y., 1973; K. Martens, "Spray Drying" Handbook, 3rd Ed. 1979, G. Goodwin Ltd. London.

The necessary formulation auxiliaries such as inert materials, surfactants, solvents and other additives are also known and described, for example, in: Watkins, "Handbook of Insecticide Dust Diluents and Carriers", 2nd Ed., Darland Books, Caldwell N.J., H.v. Olphen, "Introduction to Clay Colloid Chemistry"; 2nd Ed., J. Wiley & Sons, N.Y.; C. Marsden, "Solvents Guide"; 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface-active Ethylene Oxide Adducts], Wiss. Verlagsgesell., Stuttgart 1976; Winnacker-Küchler, "Chemische Technologie" [Chemical Technology], Volume 7, C. Hauser Verlag Munich, 4th Ed. 1986.

Based on these formulations, it is also possible to prepare combinations with other pesticidally active substances such as, for example, insecticides, acaricides, herbicides, fungicides, and with safeners, fertilizers and/or growth regulators, for example in the form of a readymix or a tank mix.

Wettable powders are preparations which are uniformly dispersible in water and which, in addition to the active ingredient, also comprise ionic and/or non-ionic surfactants (wetters, dispersants), for example polyoxyethylated alkylphenols, polyoxyethylated fatty alcohols, polyoxyethylated fatty amines, fatty alcohol polyglycol ether sulfates, alkanesulfonates, alkylbenzenesulfonates, sodium lignosulfonate, sodium 2,2'-dinaphthylmethane-6,6'-disulfonate, sodium dibutylnaphthalenesulfonate, or else sodium oleoylmethyltaurinate, in addition to a diluent or inert substance. To prepare the wettable powders, the herbicidally active ingredients are ground finely, for example in customary apparatuses such as hammer mills, blower mills and air-jet mills, and mixed with the formulation auxiliaries, either simultaneously or subsequently.

Emulsifiable concentrates are prepared, for example, by dissolving the active ingredient in an organic solvent, for example butanol, cyclohexanone, dimethylformamide, xylene, or else higher-boiling aromatics or hydrocarbons or mixtures of the organic solvents with the addition of one or more ionic or non-ionic surfactants (emulsifiers). Emulsifiers which can be used are, for example: calcium salts of alkylarylsulfonic acids, such as calcium dodecylbenzenesulfonate, or non-ionic emulsifiers such as fatty acid polyglycol esters, alkylaryl polyglycol ethers, fatty alcohol polyglycol ethers, propylene oxide/ethylene oxide condensates, alkyl polyethers, sorbitan esters, such as, for example, sorbitan fatty acid esters or polyoxyethylene sorbitan esters such as, for example, polyoxyethylene sorbitan fatty acid esters.

Dusts are obtained by grinding the active ingredient with finely divided solid substances, for example talc or natural clays such as kaolin, bentonite and pyrophyllite, or diatomaceous earth.

Suspension concentrates can be water- or oil-based. They can be obtained, for example, by wet grinding by means of commercially available bead mills and, if appropriate, an addition of surfactants as have already been mentioned for example above in the case of the other formulation types.

Emulsions, for example oil-in-water emulsions (EW), can be prepared for example by means of stirrers, colloid mills and/or static mixers using aqueous organic solvents and, if appropriate, surfactants as have already been mentioned for example above in the case of the other formulation types.

Granules can be prepared either by spraying the active ingredient onto adsorptive, granulated inert material or by applying active ingredient concentrates to the surface of carriers such as sand, kaolinites or of granulated inert material, by means of binders, for example polyvinyl alcohol, sodium polyacrylate or else mineral oils. Suitable active ingredients can also be granulated in a manner which is conventional for the production of fertilizer granules, if desired in a mixture with fertilizers.

Water-dispersible granules are prepared, as a rule, by the customary processes such as spray drying, fluidized-bed granulation, disk granulation, mixing with high-speed mixers and extrusion without solid inert material.

To prepare disk, fluidized-bed, extruder and spray granules, see, for example, processes in "Spray-Drying Handbook" 3rd Ed. 1979, G. Goodwin Ltd., London; J. E. Browning, "Agglomeration", Chemical and Engineering 1967, pages 147 et seq.; "Perry's Chemical Engineer's Handbook", 5th Ed., McGraw-Hill, New York 1973, pp. 8–57.

For further information on the formulation of crop protection products see, for example, G. C. Klingman, "Weed Control as a Science", John Wiley and Sons, Inc., New York, 1961, pages 81–96 and J. D. Freyer, S. A. Evans, "Weed Control Handbook", 5th Ed., Blackwell Scientific Publications, Oxford, 1968, pages 101–103.

As a rule, the agrochemical preparations comprise 0.1 to 99% by weight, in particular 0.1 to 95% by weight, of active ingredient of the formula (I). In wettable powders, the active ingredient concentration is, for example, approximately 10 to 90% by weight, the remainder to 100% by weight being composed of customary formulation components. In the case of emulsifiable concentrates, the active ingredient concentration can be about 1 to 90, preferably from 5 to 80, % by weight. Formulations in the form of dusts comprise. 1 to 30% by weight of active ingredient, preferably in most cases 5 to 20% by weight of active ingredient, and sprayable solutions comprise approximately 0.05 to 80, preferably 2 to 50, % by weight of active ingredient. In the case of water-dispersible granules, the active ingredient content depends partly on whether the active compound is present in liquid or solid form and on which granulation auxiliaries, fillers and the like are being used. The water-dispersible granules comprise, for example, between 1 and 95% by weight, preferably between 10 and 80% by weight, of active ingredient.

In addition, the active ingredient formulations mentioned comprise, if appropriate, the adhesives, wetters, dispersants, emulsifiers, penetrants, preservatives, antifreeze agents, solvents, fillers, carriers, colorants, antifoams, evaporation inhibitors and pH and viscosity regulators which are conventional in each case.

Suitable active ingredients which can be combined with the active ingredients according to the invention in mixed formulations or in a tank mix are, for example, known active ingredients as described for example in Weed Research 26, 441–445 (1986), or "The Pesticide Manual", 10th edition, The British Crop Protection Council and the Royal Soc. of Chemistry, 1994 and in the literature cited therein. For example the following active ingredients may be mentioned as herbicides which are known from the literature and which can be combined with the compounds of the formula (I) (note: the compounds are either named by the "common name" in accordance with the International Organization for Standardization (ISO) or by the chemical names, if appropriate together with a customary code number):

acetochlor; acifluorfen; aclonifen; AKH 7088, i.e. [[[1-[5-[2-chloro-4-(trifluoromethyl)phenoxy]-2-nitrophenyl]-2-methoxyethylidene]amino]oxy] acetic acid and its methyl ester; alachlor; alloxydim; ametryn; amidosulfuron; amitrol; AMS, i.e. ammonium sulfamate; anilofos; asulam; atrazine; azimsulfurone (DPX-A8947); aziprotryn; barban; BAS 516 H, i.e. 5-fluoro-2-phenyl-4H-3,1-benzoxazin-4-one; benazolin; benfluralin; benfuresate; bensulfuron-methyl; bensulide; bentazone; benzofenap; benzofluor; benzoylprop-ethyl; benzthiazuron; bialaphos; bifenox; bromacil; bromobutide; bromofenoxim; bromoxynil;

bromuron; buminafos; busoxinone; butachlor; butamifos; butenachlor; buthidazole; butralin; butylate; cafenstrole (CH-900); carbetamide; cafentrazone (ICI-A0051); CDAA, i.e. 2-chloro-N,N-di-2-propenylacetamide; CDEC, i.e. 2-chloroallyl diethyldithiocarbamate; chlomethoxyfen; chloramben; chlorazifop-butyl, chlormesulon (ICI-A0051); chlorbromuron; chlorbufam; chlorfenac; chlorflurecol-methyl; chloridazon; chlorimuron ethyl; chlornitrofen; chlorotoluron; chloroxuron; chlorpropham; chlorsulfuron; chlorthal-dimethyl; chlorthiamid; cinmethylin; cinosulfuron; clethodim; clodinafop and its ester derivatives (for example clodinafop-propargyl); clomazone; clomaprop, cloproxydim; clopyralid; cumyluron (JC 940); cyanazine; cycloate; cyclosulfamuron (AC 104); cycloxydim; cycluron; cyhalofop and its ester derivatives (for example butyl ester, DEH-112); cyperquat; cyprazine; cyprazole; daimuron; 2,4-DB; dalapon; desmedipham; desmetryn; di-allate; dicamba; dichlobenil; dichlorprop; diclofop and its esters such as diclofop-methyl; diethatyl; difenoxuron; difenzoquat; diflufenican; dimefuron; dimethachlor; dimethametryn; dimethenamid (SAN-582H); dimethazone, dimethipin; dimetrasulfuron, dinitramine; dinoseb; dinoterb; diphenamid; dipropetryn; diquat; dithiopyr; diuron; DNOC; eglinazine-ethyl; EL 77, i.e. 5-cyano-1-(1,1-dimethylethyl)-N-methyl-1H-pyrazole-4-carboxamide; endothal; EPTC; esprocarb; ethalfluralin; ethametsulfuron-methyl; ethidimuron; ethiozin; ethofumesate; F5231, i.e. N-[2-chloro-4-fluoro-5-[4-(3-fluoropropyl)-4,5-dihydro-5-oxo-1H-tetrazol-1-yl]-phenyl]ethanesulfonamide; ethoxyfen and its esters (for example ethyl ester, HN-252); etobenzanid (HW 52); fenoprop; fenoxan, fenoxaprop and fenoxaprop-P and their esters, for example fenoxaprop-P-ethyl and fenoxaprop-ethyl; fenoxydim; fenuron; flampropmethyl; flazasulfuron; fluazifop and fluazifop-P and their esters, for example fluazifop-butyl and fluazifop-P-butyl; fluchloralin; flumetsulam; flumeturon; flumiclorac and its esters (for example pentyl ester, S-23031); flumioxazin (S-482); flumipropyn; flupoxam (KNW-739); fluorodifen; fluoroglycofen-ethyl; flupropacil (UBIC-4243); fluridone; flurochloridone; fluroxypyr; flurtamone; fomesafen; fosamine; furyloxyfen; glufosinate; glyphosate; halosafen; halosulfuron and its esters (for example methyl ester, NC-319); haloxyfop and its esters; haloxyfop-P(=R-haloxyfop) and its esters; hexazinone; imazamethabenz-methyl; imazapyr; imazaquin and salts such as the ammonium salt; imazethamethapyr; imazethapyr; imazosulfuron; ioxynil; isocarbamid; isopropalin; isoproturon; isouron; isoxaben; isoxapyrifop; karbutilate; lactofen; lenacil; linuron; MCPA; MCPB; mecoprop; mefenacet; mefluidid; metamitron; metazachlor; methabenzthiazuron; metham; methazole; methoxyphenone; methyldymron; metabenzuron, methobenzuron; metobromuron; metolachlor; metosulam (XRD 511); metoxuron; metribuzin; metsulfuron-methyl; MH; molinate; monalide; monocarbamide dihydrogensulfate; monolinuron; monuron; MT 128, i.e. 6-chloro-N-(3-chlor-2-propenyl)-5-methyl-N-phenyl-3-pyridazinamine; MT 5950, i.e. N-[3-chloro-4-(1-methylethyl)-phenyl]-2-methylpentanamide; naproanilide; napropamide; naptalam; NC 310, i.e. 4-(2,4-dichlorobenzoyl)-1-methyl-5-benzyloxypyrazole; neburon; nicosulfuron; nipyraclophen; nitralin; nitrofen; nitrofluorfen; norflurazon; orbencarb; oryzalin; oxadiargyl (RP-020630); oxadiazon; oxyfluorfen; paraquat; pebulate; pendimethalin; perfluidone; phenisopham; phenmedipham; picloram; piperophos; piributicarb; pirifenop-butyl; pretilachlor; primisulfuron-methyl; procyazine; prodiamine; profluralin; proglinazine-ethyl; prometon; prometryn; propachlor; propanil; propaquizafop and its esters; propazine; propham; propisochlor; propyzamide; prosulfalin; prosulfocarb; prosulfuron (CGA-152005); prynachlor; pyrazolinate; pyrazon; pyrazosulfuronethyl; pyrazoxyfen; pyridate; pyrithiobac (KIH-2031); pyroxofop and its esters (for example propargyl ester); quinclorac; quinmerac; quinofop and its ester derivatives, quizalofop and quizalofop-P and their ester derivatives, for example quizalofop-ethyl; quizalofop-P-tefuryl and -ethyl; renriduron; rimsulfuron (DPX-E 9636); S 275, i.e. 2-[4-chloro-2-fluoro-5-(2-propynyloxy)phenyl]-4,5,6,7-tetrahydro-2H-indazole; secbumeton; sethoxydim; siduron; simazine; simetryn; SN 106279, i.e. 2-[[7-[2-chloro-4-(trifluoromethyl)phenoxy]-2-naphthalenyl]oxy]propanoic acid and its methyl ester; sulfentrazon (FMC-97285, F-6285); sulfazuron; sulfometuron-methyl; sulfosate (ICI-A0224); TCA; tebutam (GCP-5544); tebuthiuron; terbacil; terbucarb; terbuchlor; terbumeton; terbuthylazine; terbutryn; TFH 450, i.e. N,N-diethyl-3-[(2-ethyl-6-methylphenyl)sulfonyl]-1H-1,2,4-triazol-1-carboxamide; thenylchlor (NSK-850); thiazafluron; thiazopyr (Mon-13200); thidiazimin (SN-24085); thifensulfuron-methyl; thiobencarb; tiocarbazil; tralkoxydim; tri-allate; triasulfuron; triazofenamide; tribenuron-methyl; triclopyr; tridiphane; trietazine; trifluralin; triflusulfuron and its esters (for example methyl ester, DPX-66037); trimeturon; tsitodef; vernolate; WL 110547, i.e. 5-phenoxy-1-[3-(trifluoromethyl)phenyl]-1H-tetrazole; UBH-509; D-489; LS 82-556; KPP-300; NC-324; NC-330; KH-218; DPX-N8189; SC-0774; DOWCO-536; DK-8910; V-53482; PP-600; MBH-001; KIH-9201; ET-751; KIH-6127 and KIH-2023.

For use, the formulations which are present in commercially available form are, if appropriate, diluted in the customary manner, for example using water in the case of wettable powders, emulsifiable concentrates, dispersions and water-dispersible granules. Products in the form of dusts, granules for soil application or broadcasting and sprayable solutions are usually not further diluted with other inert substances prior to use.

The application rate of the compounds of the formula (I) required varies with the external conditions, such as temperature, humidity, the nature of the herbicide used and the like. It can vary within wide limits, for example between 0.001 and 10.0 kg/ha or more of active substance, but it is preferably between 0.005 and 5 kg/ha.

A. CHEMICAL EXAMPLES

Abbreviations: Terms like percentages and ratios are based on weight, unless otherwise specified; in vacuo means under reduced pressure; h=hour(s)

Example A1

Methyl 2-(tert-Butylaminosulfonyl)-4-cyanomethylbenzoate

A two-phase mixture of 100 g of 61.5% pure methyl 2-(tert-butylaminosulfonyl)-4-bromomethylbenzoate (61.5 g=0.169 mol), 12.09 g (0.186 mol) of potassium cyanide and 10.89 g (33.8 mmol) of tetrabutylammonium bromide in 750 ml of dichloromethane and 150 ml of water is stirred for 6 hours at room temperature.

For working-up, the batch was diluted with water, the phases were separated, and the aqueous phase was re-extracted twice with dichloromethane. The combined organic extracts were dried over Na$_2$SO$_4$. The crude product obtained after concentration was separated by chromatography on silica gel using an ethyl acetate/petroleum ether mixture (1:2, v/v). Concentration of the fractions with R$_F$=0.18 yielded 48.1 g (91.8%) of methyl 2-(tert-butylaminosulfonyl)-4-cyanomethylbenzoate of m.p.: 86–88° C.

Example A2
Methyl 4-(2-Aminoethyl)-2-tert-butylaminosulfonylbenzoate

After 0.5 g of platinum oxide hydrate had been added to a solution of 2.5 g (8.05 mmol) of methyl 2-(tert-butylaminosulfonyl)-4-cyanomethylbenzoate in 200 ml of methanol and 4 ml of concentrated HCl, the mixture was hydrogenated for 10 hours at room temperature and under a hydrogen pressure of 20 bar. For working-up, the catalyst was removed by filtration and the filtrate was concentrated. After the residue had been taken up in ethyl acetate, the solution was washed four times with 2 N HCl. The combined acidic aqueous phases are brought to pH 10–11 with concentrated ammonia and extracted three times with ethyl acetate. The organic extracts were dried over Na$_2$SO$_4$ and concentrated in vacuo. This gave 1.9 g (75%) of methyl 4-(2-aminoethyl)-2-tert-butylaminosulfonylbenzoate as an oil.

$^1$H NMR (300 MHz, CDCl$_3$): δ: 1.26 (s, 9H, C(CH$_2$)$_3$); 1.70 (bs, 2H, NH$_2$); 2.88 and 3.02 (2 m, in each case 2H, Ar—CH$_2$CH$_2$.N); 3.96 (s, 3H, OCH$_3$); 6.04 (bs, 1H, SO$_2$NH); 7.42 (dd, 1H, Ar—H, J=2 Hz, 8 Hz); 7.77 (d, 1H, Ar—H, J=8 Hz); 8.00 (d, 1H, Ar—H, J=2 Hz).

Example A3
Methyl 2-tert-Butylaminosulfonyl-4-[2-(methoxycarbonylamino)ethyl]benzoate A solution of 1.45 g (4.6 mmol) of methyl 4-(2-aminoethyl)-2-tert-butylaminosulfonylbenzoate and 0.71 ml (5.1 mmol) of triethylamine in 10 ml of dichloromethane was added dropwise to an ice-cooled solution of 1.31 g (13.8 mmol) of methyl chloroformate in 20 ml of dichloromethane. After 2 h at room temperature, water was added, the phases were separated, and the aqueous phase was re-extracted twice with dichloromethane. The combined organic extracts were washed with water, dried over Na$_2$SO$_4$ and concentrated in vacuo. This gave 1.4 g (81%) of methyl 2-tert-butylaminosulfonyl-4-[2-(methoxycarbonylamino) ethyl]benzoate as a viscous oil.

$^1$H NMR (300 MHz, CDCl$_3$): δ=1.24 (s, 9H, C(CH$_3$)$_3$); 2.95 (m, 2H, Ar—CH$_2$—CH$_2$N); 3.45 (m, 2H, Ar—CH$_2$CH$_2$N); 3.65 (s, 3H, OCH$_3$); 3.95 (s, 3H, OCH$_3$); 4.70 (bs, 1H, CONH); 6.20 (s, 1H, SO$_2$NH); 7.40 (bd, 1H, Ar—H, J=8 Hz); 7.80 (d, 1H, Ar—H, J=8 Hz); 8.00 (bs, 1H, Ar—H).

Example A4
Methyl 2-Aminosulfonyl-4-[2-(methoxycarbonylamino) ethyl]benzoate

A solution of 1.4 g (3.8 mmol) of methyl 2-tert-butylaminosulfonyl-4-[2-(methoxycarbonylamino]ethyl] benzoate in 20 ml of trifluoroacetic acid was stirred for 8 hours at room temperature. The batch was evaporated completely, re-evaporated with toluene, and the residue obtained was crystallized with ethyl acetate/diisopropyl ether. This gave 0.54 g (45%) of methyl 2-aminosulfonyl-4-[2-(methoxycarbonylamino)-ethyl]benzoate of m.p.: 146–149° C.

Example A5
Methyl 2-[(4,6-Dimethoxypyrimidin-2-yl) aminocarbonylaminosulfonyl]-4-[2-(methoxycarbonylamino)ethyl]benzoate 0.26 ml (1.7 mmol) of DBU was added dropwise to a suspension of 0.54 g (1.7 mmol) of methyl 2-aminosulfonyl-4-[2-(methoxycarbonylamino)ethyl]benzoate and 0.47 g (1.7 mmol) of N-(4,6-dimethoxypyrimidin-2-yl) phenylcarbamate in 15 ml of acetonitrile. After 2 h, the mixture was diluted with water and diethyl ether and acidified with HCl to pH 1–2, and the product precipitated was removed by filtration, washed with water and diethyl ether and dried. Yield: 0.47 g (55.6%) of methyl 2-[(4,6-dimethoxypyrimidin-2-yl)aminocarbonylaminosulfonyl]-4-[2-(methoxycarbonylamino)ethyl]benzoate of m.p.: 165–169° C./decomp.

The compounds of Tables 1 and 2 which follow are obtained analogously to Examples A1 to A5 and the above-mentioned chemical processes or generally known processes.

Abbreviations and explanations regarding Tables 1 and 2:
No.=Example number, exemplary compound No.
Me=CH$_3$=methyl
Et=C$_2$H$_5$=ethyl
Pr=n-Pr=n-Pr=n-C$_3$H$_7$=n-propyl,
i-Pr=iPr=i-C$_3$H$_7$=isopropyl
n-, i-, s-, tert-Bu=n-, i-, s-, tert-butyl
c-Alkyl=cycloalkyl
Sub-structures of the formula T* (for columns 4 and 5 in Tables 1 and 2, respectively) are radicals of the formula

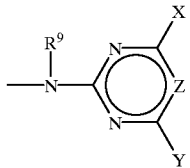

(T*)

with the meanings given in the table which follows:

| T*  | R$^9$ | X      | Y        | Z  |
|-----|-------|--------|----------|----|
| T1  | H     | OMe    | OMe      | CH |
| T2  | H     | OMe    | Me       | CH |
| T3  | H     | Me     | Me       | CH |
| T4  | H     | Me     | OEt      | CH |
| T5  | H     | Et     | OMe      | CH |
| T6  | H     | OEt    | OEt      | CH |
| T7  | H     | OCHF$_2$ | OCHF$_2$ | CH |
| T8  | H     | Me     | OCHF$_2$ | CH |
| T9  | H     | Cl     | OMe      | CH |
| T10 | H     | OMe    | OMe      | N  |
| T11 | H     | OMe    | Me       | N  |
| T12 | H     | Me     | Me       | N  |
| T13 | H     | NMe$_2$ | OCH$_2$CF$_3$ | N |
| T14 | H     | OMe    | CF$_3$   | N  |
| T15 | H     | OEt    | NHMe     | N  |
| T16 | Me    | OMe    | OMe      | CH |
| T17 | Me    | OMe    | Me       | N  |

Specific information regarding Table 1:

In combined Table 1 there are listed examples of compounds of the formulae (Ia), (Ib), (Ic) and (Id). One line in Table 1 characterizes a definition of the combination of the radicals R$^6$, R$^7$ and T* for each of the formulae (Ia), (Ib), (Ic) and (Id), in which R$^1$ is in each case rigidly defined. The compound of the formula (Ia) in one line is given the example number from the line number with the letter "a" attached. The same applies analogously to compounds of the formulae (Ib), (Ic) and (Id) which, in each line, correspond with the example with "b", "c" and "d", respectively, attached.

Any information on physical data, generally the melting point of the examples in question, are given in the box which is located in the line with the example number and in the column underneath the formula number (Ia, Ib, Ic or Id) and which is thus unambiguously assigned to the compound.

A box in the column underneath (Ia) thus exactly defines a compound of the formula (Ia) whose example number is the number given in the column under "No." with the letter "a" attached; the same applies analogously to the examples of the compounds of the formulae (Ib) to (Id).

Unless otherwise specified, the numbers in the boxes in the column underneath (Ia), (Ib), (Ic) or (Id) indicate melting points in degrees Celsius (° C.).

TABLE 1

Compounds of the formulae (Ia), (Ib), (Ic) and (Id)

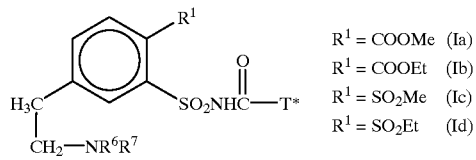

R¹ = COOMe (Ia)
R¹ = COOEt (Ib)
R¹ = SO$_2$Me (Ic)
R¹ = SO$_2$Et (Id)

| Ex. No. | R$^6$ | R$^7$ | T* | (Ia) | (Ib) | (Ic) | (Id) |
|---|---|---|---|---|---|---|---|
| 1 a-d | H | CHO | T1 | 110–115 | | | |
| 2 a-d | H | " | T2 | | | | |
| 3 a-d | H | " | T3 | | | | |
| 4 a-d | H | " | T4 | | | | |
| 5 a-d | H | " | T5 | | | | |
| 6 a-d | H | " | T6 | | | | |
| 7 a-d | H | " | T7 | | | | |
| 8 a-d | H | " | T8 | | | | |
| 9 a-d | H | " | T9 | | | | |
| 10 a-d | H | " | T10 | | | | |
| 11 a-d | H | " | T11 | | | | |
| 12 a-d | H | " | T12 | | | | |
| 13 a-d | H | " | T13 | | | | |
| 14 a-d | H | " | T14 | | | | |
| 15 a-d | H | " | T15 | | | | |
| 16 a-d | H | " | T16 | | | | |
| 17 a-d | H | " | T17 | | | | |
| 18 a-d | H | COMe | T1 | 199–200 | | | |
| 19 a-d | H | COMe | T2 | | | | |
| 20 a-d | H | COMe | T3 | | | | |
| 21 a-d | H | COMe | T4 | | | | |
| 22 a-d | H | COMe | T5 | | | | |
| 23 a-d | H | COMe | T6 | | | | |
| 24 a-d | H | COMe | T7 | | | | |
| 25 a-d | H | COMe | T8 | | | | |
| 26 a-d | H | COMe | T9 | | | | |
| 27 a-d | H | COMe | T10 | | | | |
| 28 a-d | H | COMe | T11 | | | | |
| 29 a-d | H | COMe | T12 | | | | |
| 30 a-d | H | COMe | T13 | | | | |
| 31 a-d | H | COMe | T14 | | | | |
| 32 a-d | H | COMe | T15 | | | | |
| 33 a-d | H | COMe | T16 | | | | |
| 34 a-d | H | COMe | T17 | | | | |
| 35 a-d | H | COEt | T1 | | | | |
| 36 a-d | H | COEt | T2 | | | | |
| 37 a-d | H | COEt | T3 | | | | |
| 38 a-d | H | COEt | T4 | | | | |
| 39 a-d | H | COEt | T5 | | | | |
| 40 a-d | H | COEt | T6 | | | | |
| 41 a-d | H | COEt | T7 | | | | |
| 42 a-d | H | COEt | T8 | | | | |
| 43 a-d | H | COEt | T9 | | | | |
| 44 a-d | H | COEt | T10 | | | | |
| 45 a-d | H | COEt | T11 | | | | |
| 46 a-d | H | COEt | T12 | | | | |
| 47 a-d | H | COEt | T13 | | | | |
| 48 a-d | H | COEt | T14 | | | | |
| 49 a-d | H | COEt | T15 | | | | |
| 50 a-d | H | COEt | T16 | | | | |
| 51 a-d | H | COEt | T17 | | | | |

TABLE 1-continued

Compounds of the formulae (Ia), (Ib), (Ic) and (Id)

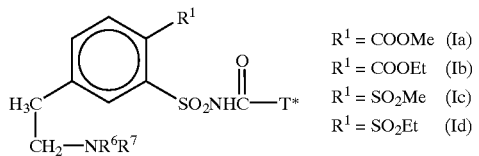

R¹ = COOMe (Ia)
R¹ = COOEt (Ib)
R¹ = SO₂Me (Ic)
R¹ = SO₂Et (Id)

| Ex. No. | R⁶ | R⁷ | T* | (Ia) | (Ib) | (Ic) | (Id) |
|---|---|---|---|---|---|---|---|
| 52 a–d | H | CO$_n$C$_3$H$_7$ | T1 | | | | |
| 53 a–d | H | CO$_n$C$_3$H$_7$ | T2 | | | | |
| 54 a–d | H | CO$_n$C$_3$H$_7$ | T3 | | | | |
| 55 a–d | H | CO$_n$C$_3$H$_7$ | T4 | | | | |
| 56 a–d | H | CO$_n$C$_3$H$_7$ | T5 | | | | |
| 57 a–d | H | CO$_n$C$_3$H$_7$ | T6 | | | | |
| 58 a–d | H | CO$_n$C$_3$H$_7$ | T7 | | | | |
| 59 a–d | H | CO$_n$C$_3$H$_7$ | T8 | | | | |
| 60 a–d | H | CO$_n$C$_3$H$_7$ | T9 | | | | |
| 61 a–d | H | CO$_n$C$_3$H$_7$ | T10 | | | | |
| 62 a–d | H | CO$_n$C$_3$H$_7$ | T11 | | | | |
| 63 a–d | H | CO$_n$C$_3$H$_7$ | T12 | | | | |
| 64 a–d | H | CO$_n$C$_3$H$_7$ | T13 | | | | |
| 65 a–d | H | CO$_n$C$_3$H$_7$ | T14 | | | | |
| 66 a–d | H | CO$_n$C$_3$H$_7$ | T15 | | | | |
| 67 a–d | H | CO$_n$C$_3$H$_7$ | T16 | | | | |
| 68 a–d | H | CO$_n$C$_3$H$_7$ | T17 | | | | |
| 69 a–d | H | CO-i-Pr | T1 | 103–108 | | | |
| 70 a–d | H | CO-i-Pr | T2 | | | | |
| 71 a–d | H | CO-i-Pr | T3 | | | | |
| 72 a–d | H | CO-i-Pr | T4 | | | | |
| 73 a–d | H | CO-i-Pr | T5 | | | | |
| 74 a–d | H | CO-i-Pr | T6 | | | | |
| 75 a–d | H | CO-i-Pr | T7 | | | | |
| 76 a–d | H | CO-i-Pr | T8 | | | | |
| 77 a–d | H | CO-i-Pr | T9 | | | | |
| 78 a–d | H | CO-i-Pr | T10 | | | | |
| 79 a–d | H | CO-i-Pr | T11 | | | | |
| 80 a–d | H | CO-i-Pr | T12 | | | | |
| 81 a–d | H | CO-i-Pr | T13 | | | | |
| 82 a–d | H | CO-i-Pr | T14 | | | | |
| 83 a–d | H | CO-i-Pr | T15 | | | | |
| 84 a–d | H | CO-i-Pr | T16 | | | | |
| 85 a–d | H | CO-i-Pr | T17 | | | | |
| 86 a–d | H | COCF$_3$ | T1 | 200–203 | | | |
| 87 a–d | H | COCF$_3$ | T2 | | | | |
| 88 a–d | H | COCF$_3$ | T3 | | | | |
| 89 a–d | H | COCF$_3$ | T4 | | | | |
| 90 a–d | H | COCF$_3$ | T5 | | | | |
| 91 a–d | H | COCF$_3$ | T6 | | | | |
| 92 a–d | H | COCF$_3$ | T7 | | | | |
| 93 a–d | H | COCF$_3$ | T8 | | | | |
| 94 a–d | H | COCF$_3$ | T9 | | | | |
| 95 a–d | H | COCF$_3$ | T10 | | | | |
| 96 a–d | H | COCF$_3$ | T11 | | | | |
| 97 a–d | H | COCF$_3$ | T12 | | | | |
| 98 a–d | H | COCF$_3$ | T13 | | | | |
| 99 a–d | H | COCF$_3$ | T14 | | | | |
| 100 a–d | H | COCF$_3$ | T15 | | | | |
| 101 a–d | H | COCF$_3$ | T16 | | | | |
| 102 a–d | H | COCF$_3$ | T17 | | | | |
| 103 a–d | H | COOCH$_3$ | T1 | 165–169 | | | |
| 104 a–d | H | COOCH$_3$ | T2 | | | | |
| 105 a–d | H | COOCH$_3$ | T3 | | | | |
| 106 a–d | H | COOCH$_3$ | T4 | | | | |
| 107 a–d | H | COOCH$_3$ | T5 | | | | |
| 108 a–d | H | COOCH$_3$ | T6 | | | | |
| 109 a–d | H | COOCH$_3$ | T7 | | | | |
| 110 a–d | H | COOCH$_3$ | T8 | | | | |
| 111 a–d | H | COOCH$_3$ | T9 | | | | |
| 112 a–d | H | COOCH$_3$ | T10 | | | | |
| 113 a–d | H | COOCH$_3$ | T11 | | | | |
| 114 a–d | H | COOCH$_3$ | T12 | | | | |
| 115 a–d | H | COOCH$_3$ | T13 | | | | |
| 116 a–d | H | COOCH$_3$ | T14 | | | | |
| 117 a–d | H | COOCH$_3$ | T15 | | | | |

TABLE 1-continued

Compounds of the formulae (Ia), (Ib), (Ic) and (Id)

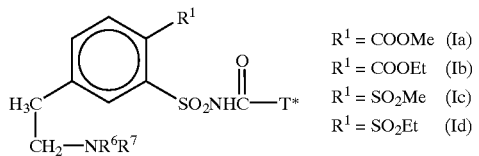

$R^1$ = COOMe (Ia)
$R^1$ = COOEt (Ib)
$R^1$ = SO$_2$Me (Ic)
$R^1$ = SO$_2$Et (Id)

| Ex. No. | $R^6$ | $R^7$ | T* | (Ia) | (Ib) | (Ic) | (Id) |
|---|---|---|---|---|---|---|---|
| 118 a-d | H | COOCH$_3$ | T16 | | | | |
| 119 a-d | H | COOCH$_3$ | T17 | | | | |
| 120 a-d | H | COOEt | T1 | | | | |
| 121 a-d | H | " | T2 | | | | |
| 122 a-d | H | " | T3 | | | | |
| 123 a-d | H | " | T4 | | | | |
| 124 a-d | H | " | T5 | | | | |
| 125 a-d | H | " | T6 | | | | |
| 126 a-d | H | " | T7 | | | | |
| 127 a-d | H | " | T8 | | | | |
| 128 a-d | H | " | T9 | | | | |
| 129 a-d | H | " | T10 | | | | |
| 130 a-d | H | " | T11 | | | | |
| 131 a-d | H | " | T12 | | | | |
| 132 a-d | H | " | T13 | | | | |
| 133 a-d | H | " | T14 | | | | |
| 134 a-d | H | " | T15 | | | | |
| 135 a-d | H | " | T16 | | | | |
| 136 a-d | H | " | T17 | | | | |
| 137 a-d | H | SO$_2$CH$_3$ | T1 | 112–114 | | | |
| 138 a-d | H | SO$_2$CH$_3$ | T2 | | | | |
| 139 a-d | H | SO$_2$CH$_3$ | T3 | | | | |
| 140 a-d | H | SO$_2$CH$_3$ | T4 | | | | |
| 141 a-d | H | SO$_2$CH$_3$ | T5 | | | | |
| 142 a-d | H | SO$_2$CH$_3$ | T6 | | | | |
| 143 a-d | H | SO$_2$CH$_3$ | T7 | | | | |
| 144 a-d | H | SO$_2$CH$_3$ | T8 | | | | |
| 145 a-d | H | SO$_2$CH$_3$ | T9 | | | | |
| 146 a-d | H | SO$_2$CH$_3$ | T10 | | | | |
| 147 a-d | H | SO$_2$CH$_3$ | T11 | | | | |
| 148 a-d | H | SO$_2$CH$_3$ | T12 | | | | |
| 149 a-d | H | SO$_2$CH$_3$ | T13 | | | | |
| 150 a-d | H | SO$_2$CH$_3$ | T14 | | | | |
| 151 a-d | H | SO$_2$CH$_3$ | T15 | | | | |
| 152 a-d | H | SO$_2$CH$_3$ | T16 | | | | |
| 153 a-d | H | SO$_2$CH$_3$ | T17 | | | | |
| 154 a-d | H | SO$_2$Et | T1 | 103–105 | | | |
| 155 a-d | H | SO$_2$Et | T2 | | | | |
| 156 a-d | H | SO$_2$Et | T3 | | | | |
| 157 a-d | H | SO$_2$Et | T4 | | | | |
| 158 a-d | H | SO$_2$Et | T5 | | | | |
| 159 a-d | H | SO$_2$Et | T6 | | | | |
| 160 a-d | H | SO$_2$Et | T7 | | | | |
| 161 a-d | H | SO$_2$Et | T8 | | | | |
| 162 a-d | H | SO$_2$Et | T9 | | | | |
| 163 a-d | H | SO$_2$Et | T10 | | | | |
| 164 a-d | H | SO$_2$Et | T11 | | | | |
| 165 a-d | H | SO$_2$Et | T12 | | | | |
| 166 a-d | H | SO$_2$Et | T13 | | | | |
| 167 a-d | H | SO$_2$Et | T14 | | | | |
| 168 a-d | H | SO$_2$Et | T15 | | | | |
| 169 a-d | H | SO$_2$Et | T16 | | | | |
| 170 a-d | H | SO$_2$Et | T17 | | | | |
| 171 a-d | H | SO$_2$nPr | T1 | | | | |
| 172 a-d | H | SO$_2$nPr | T2 | | | | |
| 173 a-d | H | SO$_2$nPr | T3 | | | | |
| 174 a-d | H | SO$_2$nPr | T4 | | | | |
| 175 a-d | H | SO$_2$nPr | T5 | | | | |
| 176 a-d | H | SO$_2$nPr | T6 | | | | |
| 177 a-d | H | SO$_2$nPr | T7 | | | | |
| 178 a-d | H | SO$_2$nPr | T8 | | | | |
| 179 a-d | H | SO$_2$nPr | T9 | | | | |
| 180 a-d | H | SO$_2$nPr | T10 | | | | |
| 181 a-d | H | SO$_2$nPr | T11 | | | | |
| 182 a-d | H | SO$_2$nPr | T12 | | | | |
| 183 a-d | H | SO$_2$nPr | T13 | | | | |

TABLE 1-continued

Compounds of the formulae (Ia), (Ib), (Ic) and (Id)

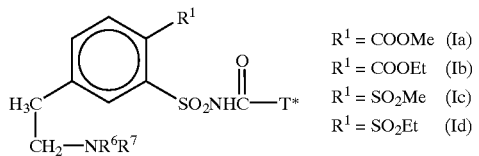

R¹ = COOMe (Ia)
R¹ = COOEt (Ib)
R¹ = SO₂Me (Ic)
R¹ = SO₂Et (Id)

| Ex. No. | R⁶ | R⁷ | T* | (Ia) | (Ib) | (Ic) | (Id) |
|---|---|---|---|---|---|---|---|
| 184 a-d | H | SO₂nPr | T14 | | | | |
| 185 a-d | H | SO₂nPr | T15 | | | | |
| 186 a-d | H | SO₂nPr | T16 | | | | |
| 187 a-d | H | SO₂nPr | T17 | | | | |
| 188 a-d | H | SO₂iPr | T1 | | | | |
| 189 a-d | H | SO₂iPr | T2 | | | | |
| 190 a-d | H | SO₂iPr | T3 | | | | |
| 191 a-d | H | SO₂iPr | T4 | | | | |
| 192 a-d | H | SO₂iPr | T5 | | | | |
| 193 a-d | H | SO₂iPr | T6 | | | | |
| 194 a-d | H | SO₂iPr | T7 | | | | |
| 195 a-d | H | SO₂iPr | T8 | | | | |
| 196 a-d | H | SO₂iPr | T9 | | | | |
| 197 a-d | H | SO₂iPr | T10 | | | | |
| 198 a-d | H | SO₂iPr | T11 | | | | |
| 199 a-d | H | SO₂iPr | T12 | | | | |
| 200 a-d | H | SO₂iPr | T13 | | | | |
| 201 a-d | H | SO₂iPr | T14 | | | | |
| 202 a-d | H | SO₂iPr | T15 | | | | |
| 203 a-d | H | SO₂iPr | T16 | | | | |
| 204 a-d | H | SO₂iPr | T17 | | | | |
| 205 a-d | H | ClCH₂CO— | T1 | | | | |
| 206 a-d | H | ClCH₂CO— | T2 | | | | |
| 207 a-d | H | ClCH₂CO— | T3 | | | | |
| 208 a-d | H | ClCH₂CO— | T9 | | | | |
| 209 a-d | H | ClCH₂CO— | T10 | | | | |
| 210 a-d | H | ClCH₂CO— | T11 | | | | |
| 211 a-d | H | ClCH₂CO— | T14 | | | | |
| 212 a-d | H | ClCH₂CO— | T16 | | | | |
| 213 a-d | H | ClCH₂CO— | T17 | | | | |
| 214 a-d | H | Cl₂CHCO— | T1 | | | | |
| 215 a-d | H | Cl₂CHCO— | T2 | | | | |
| 216 a-d | H | Cl₂CHCO— | T3 | | | | |
| 217 a-d | H | Cl₂CHCO— | T9 | | | | |
| 218 a-d | H | Cl₂CHCO— | T10 | | | | |
| 219 a-d | H | Cl₂CHCO— | T11 | | | | |
| 220 a-d | H | Cl₂CHCO— | T14 | | | | |
| 221 a-d | H | Cl₂CHCO— | T16 | | | | |
| 222 a-d | H | Cl₂CHCO— | T17 | | | | |
| 223 a-d | H | Cl₃CCO— | T1 | | | | |
| 224 a-d | H | Cl₃CCO— | T2 | | | | |
| 225 a-d | H | Cl₃CCO— | T3 | | | | |
| 226 a-d | H | Cl₃CCO— | T9 | | | | |
| 227 a-d | H | Cl₃CCO— | T10 | | | | |
| 228 a-d | H | Cl₃CCO— | T11 | | | | |
| 229 a-d | H | Cl₃CCO— | T14 | | | | |
| 230 a-d | H | Cl₃CCO— | T16 | | | | |
| 231 a-d | H | Cl₃CCO— | T17 | | | | |
| 232 a-d | H | CH₃OCH₂CO | T1 | | | | |
| 233 a-d | H | CH₃OCH₂CO | T2 | | | | |
| 234 a-d | H | CH₃OCH₂CO | T3 | | | | |
| 235 a-d | H | CH₃OCH₂CO | T9 | | | | |
| 236 a-d | H | CH₃OCH₂CO | T10 | | | | |
| 237 a-d | H | CH₃OCH₂CO | T11 | | | | |
| 238 a-d | H | CH₃OCH₂CO | T14 | | | | |
| 239 a-d | H | CH₃OCH₂CO | T16 | | | | |
| 240 a-d | H | CH₃OCH₂CO | T17 | | | | |
| 241 a-d | H | CH₂=CHCO | T1 | | | | |
| 242 a-d | H | CH₂=CHCO | T2 | | | | |
| 243 a-d | H | CH₂=CHCO | T3 | | | | |
| 244 a-d | H | CH₂=CHCO | T9 | | | | |
| 245 a-d | H | CH₂=CHCO | T10 | | | | |
| 246 a-d | H | CH₂=CHCO | T11 | | | | |
| 247 a-d | H | CH₂=CHCO | T14 | | | | |
| 248 a-d | H | CH₂=CHCO | T16 | | | | |
| 249 a-d | H | CH₂=CHCO | T17 | | | | |

TABLE 1-continued

Compounds of the formulae (Ia), (Ib), (Ic) and (Id)

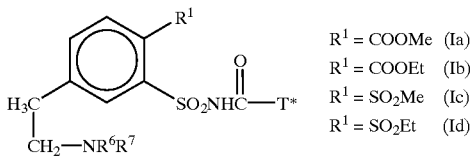

R¹ = COOMe (Ia)
R¹ = COOEt (Ib)
R¹ = SO₂Me (Ic)
R¹ = SO₂Et (Id)

| Ex. No. | R⁶ | R⁷ | T* | (Ia) | (Ib) | (Ic) | (Id) |
|---|---|---|---|---|---|---|---|
| 250 a-d | H | CH≡CCO | T1 | | | | |
| 251 a-d | H | CH≡CCO | T2 | | | | |
| 252 a-d | H | CH≡CCO | T3 | | | | |
| 253 a-d | H | CH≡CCO | T9 | | | | |
| 254 a-d | H | CH≡CCO | T10 | | | | |
| 255 a-d | H | CH≡CCO | T11 | | | | |
| 256 a-d | H | CH≡CCO | T14 | | | | |
| 257 a-d | H | CH≡CCO | T16 | | | | |
| 258 a-d | H | CH≡CCO | T17 | | | | |
| 259 a-d | H | CO-cyclopropyl | T1 | 180–181 | | | |
| 260 a-d | H | " | T2 | | | | |
| 261 a-d | H | " | T3 | | | | |
| 262 a-d | H | " | T9 | | | | |
| 263 a-d | H | " | T10 | | | | |
| 264 a-d | H | " | T11 | | | | |
| 265 a-d | H | " | T14 | | | | |
| 266 a-d | H | " | T16 | | | | |
| 267 a-d | H | " | T17 | | | | |
| 268 a-d | H | CO-cyclobutyl | T1 | | | | |
| 269 a-d | H | " | T2 | | | | |
| 270 a-d | H | " | T3 | | | | |
| 271 a-d | H | " | T9 | | | | |
| 272 a-d | H | " | T10 | | | | |
| 273 a-d | H | " | T11 | | | | |
| 274 a-d | H | " | T14 | | | | |
| 275 a-d | H | " | T16 | | | | |
| 276 a-d | H | " | T17 | | | | |
| 277 a-d | H | CO-cyclopentyl | T1 | | | | |
| 278 a-d | H | " | T2 | | | | |
| 279 a-d | H | " | T3 | | | | |
| 280 a-d | H | " | T9 | | | | |
| 281 a-d | H | " | T10 | | | | |
| 282 a-d | H | " | T11 | | | | |
| 283 a-d | H | " | T14 | | | | |
| 284 a-d | H | " | T16 | | | | |
| 285 a-d | H | " | T17 | | | | |
| 286 a-d | H | CO-cyclohexyl | T1 | | | | |
| 287 a-d | H | " | T2 | | | | |
| 288 a-d | H | " | T3 | | | | |
| 289 a-d | H | " | T9 | | | | |
| 290 a-d | H | " | T10 | | | | |
| 291 a-d | H | " | T11 | | | | |
| 292 a-d | H | " | T14 | | | | |
| 293 a-d | H | " | T16 | | | | |
| 294 a-d | H | " | T17 | | | | |
| 295 a-d | H | SO₂CF₃ | T1 | | | | |

TABLE 1-continued

Compounds of the formulae (Ia), (Ib), (Ic) and (Id)

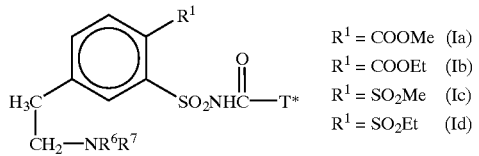

R$^1$ = COOMe (Ia)
R$^1$ = COOEt (Ib)
R$^1$ = SO$_2$Me (Ic)
R$^1$ = SO$_2$Et (Id)

| Ex. No. | R$^6$ | R$^7$ | T* | (Ia) | (Ib) | (Ic) | (Id) |
|---|---|---|---|---|---|---|---|
| 296 a-d | H | SO$_2$CF$_3$ | T2 | | | | |
| 297 a-d | H | SO$_2$CF$_3$ | T3 | | | | |
| 298 a-d | H | SO$_2$CF$_3$ | T9 | | | | |
| 299 a-d | H | SO$_2$CF$_3$ | T10 | | | | |
| 300 a-d | H | SO$_2$CF$_3$ | T11 | | | | |
| 301 a-d | H | SO$_2$CF$_3$ | T14 | | | | |
| 302 a-d | H | SO$_2$CF$_3$ | T16 | | | | |
| 303 a-d | H | SO$_2$CF$_3$ | T17 | | | | |
| 304 a-d | H | SO$_2$CH$_2$F | T1 | | | | |
| 305 a-d | H | SO$_2$CH$_2$F | T2 | | | | |
| 306 a-d | H | SO$_2$CH$_2$F | T3 | | | | |
| 307 a-d | H | SO$_2$CH$_2$F | T9 | | | | |
| 308 a-d | H | SO$_2$CH$_2$F | T10 | | | | |
| 309 a-d | H | SO$_2$CH$_2$F | T11 | | | | |
| 310 a-d | H | SO$_2$CH$_2$F | T14 | | | | |
| 311 a-d | H | SO$_2$CH$_2$F | T16 | | | | |
| 312 a-d | H | SO$_2$CH$_2$F | T17 | | | | |
| 313 a-d | H | SO$_2$CH$_2$Cl | T1 | | | | |
| 314 a-d | H | SO$_2$CH$_2$Cl | T2 | | | | |
| 315 a-d | H | SO$_2$CH$_2$Cl | T3 | | | | |
| 316 a-d | H | SO$_2$CH$_2$Cl | T9 | | | | |
| 317 a-d | H | SO$_2$CH$_2$Cl | T10 | | | | |
| 318 a-d | H | SO$_2$CH$_2$Cl | T11 | | | | |
| 319 a-d | H | SO$_2$CH$_2$Cl | T14 | | | | |
| 320 a-d | H | SO$_2$CH$_2$Cl | T16 | | | | |
| 321 a-d | H | SO$_2$CH$_2$Cl | T17 | | | | |
| 322 a-d | H | SO$_2$CHCl$_2$ | T1 | | | | |
| 323 a-d | H | SO$_2$CHCl$_2$ | T2 | | | | |
| 324 a-d | H | SO$_2$CHCl$_2$ | T3 | | | | |
| 325 a-d | H | SO$_2$CHCl$_2$ | T9 | | | | |
| 326 a-d | H | SO$_2$CHCl$_2$ | T10 | | | | |
| 327 a-d | H | SO$_2$CHCl$_2$ | T11 | | | | |
| 328 a-d | H | SO$_2$CHCl$_2$ | T14 | | | | |
| 329 a-d | H | SO$_2$CHCl$_2$ | T16 | | | | |
| 330 a-d | H | SO$_2$CHCl$_2$ | T17 | | | | |
| 331 a-d | H | SO$_2$CCl$_3$ | T1 | | | | |
| 332 a-d | H | SO$_2$CCl$_3$ | T2 | | | | |
| 333 a-d | H | SO$_2$CCl$_3$ | T3 | | | | |
| 334 a-d | H | SO$_2$CCl$_3$ | T9 | | | | |
| 335 a-d | H | SO$_2$CCl$_3$ | T10 | | | | |
| 336 a-d | H | SO$_2$CCl$_3$ | T11 | | | | |
| 337 a-d | H | SO$_2$CCl$_3$ | T14 | | | | |
| 338 a-d | H | SO$_2$CCl$_3$ | T16 | | | | |
| 339 a-d | H | SO$_2$CCl$_3$ | T17 | | | | |
| 340 a-d | H | SO$_2$n-Bu | T1 | | | | |
| 341 a-d | H | SO$_2$n-Bu | T2 | | | | |
| 342 a-d | H | SO$_2$n-Bu | T3 | | | | |
| 343 a-d | H | SO$_2$n-Bu | T9 | | | | |
| 344 a-d | H | SO$_2$n-Bu | T10 | | | | |
| 345 a-d | H | SO$_2$n-Bu | T11 | | | | |
| 346 a-d | H | SO$_2$n-Bu | T14 | | | | |
| 347 a-d | H | SO$_2$n-Bu | T16 | | | | |
| 348 a-d | H | SO$_2$n-Bu | T17 | | | | |
| 349 a-d | H | SO$_2$CH$_2$CF$_3$ | T1 | | | | |
| 350 a-d | H | SO$_2$CH$_2$CF$_3$ | T2 | | | | |
| 351 a-d | H | SO$_2$CH$_2$CF$_3$ | T3 | | | | |
| 352 a-d | H | SO$_2$CH$_2$CF$_3$ | T9 | | | | |
| 353 a-d | H | SO$_2$CH$_2$CF$_3$ | T10 | | | | |
| 354 a-d | H | SO$_2$CH$_2$CF$_3$ | T11 | | | | |
| 355 a-d | H | SO$_2$CH$_2$CF$_3$ | T14 | | | | |
| 356 a-d | H | SO$_2$CH$_2$CF$_3$ | T16 | | | | |
| 357 a-d | H | SO$_2$CH$_2$CF$_3$ | T17 | | | | |
| 358 a-d | H | SO$_2$NHCH$_3$ | T1 | | | | |
| 359 a-d | H | SO$_2$NHCH$_3$ | T2 | | | | |
| 360 a-d | H | SO$_2$NHCH$_3$ | T3 | | | | |
| 361 a-d | H | SO$_2$NHCH$_3$ | T9 | | | | |

TABLE 1-continued

Compounds of the formulae (Ia), (Ib), (Ic) and (Id)

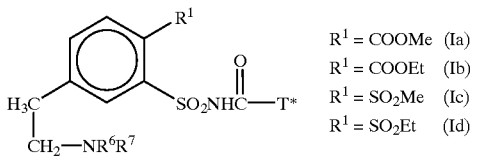

$R^1$ = COOMe (Ia)
$R^1$ = COOEt (Ib)
$R^1$ = SO$_2$Me (Ic)
$R^1$ = SO$_2$Et (Id)

| Ex. No. | R$^6$ | R$^7$ | T* | (Ia) | (Ib) | (Ic) | (Id) |
|---|---|---|---|---|---|---|---|
| 362 a-d | H | SO$_2$NHCH$_3$ | T10 | | | | |
| 363 a-d | H | SO$_2$NHCH$_3$ | T11 | | | | |
| 364 a-d | H | SO$_2$NHCH$_3$ | T14 | | | | |
| 365 a-d | H | SO$_2$NHCH$_3$ | T16 | | | | |
| 366 a-d | H | SO$_2$NHCH$_3$ | T17 | | | | |
| 367 a-d | H | SO$_2$N(CH$_3$)$_2$ | T1 | | | | |
| 368 a-d | H | SO$_2$N(CH$_3$)$_2$ | T2 | | | | |
| 369 a-d | H | SO$_2$N(CH$_3$)$_2$ | T3 | | | | |
| 370 a-d | H | SO$_2$N(CH$_3$)$_2$ | T9 | | | | |
| 371 a-d | H | SO$_2$N(CH$_3$)$_2$ | T10 | | | | |
| 372 a-d | H | SO$_2$N(CH$_3$)$_2$ | T11 | | | | |
| 373 a-d | H | SO$_2$N(CH$_3$)$_2$ | T14 | | | | |
| 374 a-d | H | SO$_2$N(CH$_3$)$_2$ | T16 | | | | |
| 375 a-d | H | SO$_2$N(CH$_3$)$_2$ | T17 | | | | |
| 376 a-d | H | (CH$_3$)$_3$COCO | T1 | | | | |
| 377 a-d | H | (CH$_3$)$_3$COCO | T2 | | | | |
| 378 a-d | H | (CH$_3$)$_3$COCO | T3 | | | | |
| 379 a-d | H | (CH$_3$)$_3$COCO | T9 | | | | |
| 380 a-d | H | (CH$_3$)$_3$COCO | T10 | | | | |
| 381 a-d | H | (CH$_3$)$_3$COCO | T11 | | | | |
| 382 a-d | H | (CH$_3$)$_3$COCO | T14 | | | | |
| 383 a-d | H | (CH$_3$)$_3$COCO | T16 | | | | |
| 384 a-d | H | (CH$_3$)$_3$COCO | T17 | | | | |
| 385 a-d | H | PhCO | T1 | | | | |
| 386 a-d | H | PhCO | T2 | | | | |
| 387 a-d | H | PhCO | T3 | | | | |
| 388 a-d | H | PhCO | T9 | | | | |
| 389 a-d | H | PhCO | T10 | | | | |
| 390 a-d | H | PhCO | T11 | | | | |
| 391 a-d | H | PhCO | T14 | | | | |
| 392 a-d | H | PhCO | T16 | | | | |
| 393 a-d | H | PhCO | T17 | | | | |
| 394 a-d | H | PhSO$_2$ | T1 | | | | |
| 395 a-d | H | PhSO$_2$ | T2 | | | | |
| 396 a-d | H | PhSO$_2$ | T3 | | | | |
| 397 a-d | H | PhSO$_2$ | T9 | | | | |
| 398 a-d | H | PhSO$_2$ | T10 | | | | |
| 399 a-d | H | PhSO$_2$ | T11 | | | | |
| 400 a-d | H | PhSO$_2$ | T14 | | | | |
| 401 a-d | H | PhSO$_2$ | T16 | | | | |
| 402 a-d | H | PhSO$_2$ | T17 | | | | |
| 403 a-d | H | MeNHCO | T1 | | | | |
| 404 a-d | H | MeNHCO | T2 | | | | |
| 405 a-d | H | MeNHCO | T3 | | | | |
| 406 a-d | H | MeNHCO | T9 | | | | |
| 407 a-d | H | MeNHCO | T10 | | | | |
| 408 a-d | H | MeNHCO | T11 | | | | |
| 409 a-d | H | MeNHCO | T14 | | | | |
| 410 a-d | H | MeNHCO | T16 | | | | |
| 411 a-d | H | MeNHCO | T17 | | | | |
| 412 a-d | H | EtNHCO | T1 | | | | |
| 413 a-d | H | EtNHCO | T2 | | | | |
| 414 a-d | H | EtNHCO | T3 | | | | |
| 415 a-d | H | EtNHCO | T9 | | | | |
| 416 a-d | H | EtNHCO | T10 | | | | |
| 417 a-d | H | EtNHCO | T11 | | | | |
| 418 a-d | H | EtNHCO | T14 | | | | |
| 419 a-d | H | EtNHCO | T16 | | | | |
| 420 a-d | H | EtNHCO | T17 | | | | |
| 421 a-d | H | MeNHCS | T1 | | | | |
| 422 a-d | H | MeNHCS | T2 | | | | |
| 423 a-d | H | MeNHCS | T3 | | | | |
| 424 a-d | H | MeNHCS | T9 | | | | |
| 425 a-d | H | MeNHCS | T10 | | | | |
| 426 a-d | H | MeNHCS | T11 | | | | |
| 427 a-d | H | MeNHCS | T14 | | | | |

TABLE 1-continued

Compounds of the formulae (Ia), (Ib), (Ic) and (Id)

$R^1$ = COOMe (Ia)
$R^1$ = COOEt (Ib)
$R^1$ = SO$_2$Me (Ic)
$R^1$ = SO$_2$Et (Id)

| Ex. No. | $R^6$ | $R^7$ | T* | (Ia) | (Ib) | (Ic) | (Id) |
|---|---|---|---|---|---|---|---|
| 428 a-d | H | MeNHCS | T16 | | | | |
| 429 a-d | H | MeNHCS | T17 | | | | |
| 430 a-d | H | EtNHCS | T1 | | | | |
| 431 a-d | H | EtNHCS | T2 | | | | |
| 432 a-d | H | EtNHCS | T3 | | | | |
| 433 a-d | H | EtNHCS | T9 | | | | |
| 434 a-d | H | EtNHCS | T10 | | | | |
| 435 a-d | H | EtNHCS | T11 | | | | |
| 436 a-d | H | EtNHCS | T14 | | | | |
| 437 a-d | H | EtNHCS | T16 | | | | |
| 438 a-d | H | EtNHCS | T17 | | | | |
| 439 a-d | cyclopentanone | | T1 | | | | |
| 440 a-d | " | | T2 | | | | |
| 441 a-d | " | | T3 | | | | |
| 442 a-d | " | | T9 | | | | |
| 443 a-d | " | | T10 | | | | |
| 444 a-d | " | | T11 | | | | |
| 445 a-d | " | | T14 | | | | |
| 446 a-d | " | | T16 | | | | |
| 447 a-d | " | | T17 | | | | |
| 448 a-d | cyclohexanone | | T1 | | | | |
| 449 a-d | " | | T2 | | | | |
| 450 a-d | " | | T3 | | | | |
| 451 a-d | " | | T9 | | | | |
| 452 a-d | " | | T10 | | | | |
| 453 a-d | " | | T11 | | | | |
| 454 a-d | " | | T14 | | | | |
| 455 a-d | " | | T16 | | | | |
| 456 a-d | " | | T17 | | | | |
| 457 a-d | tetrahydrothiophene-SO$_2$ | | T1 | | | | |
| 458 a-d | " | | T2 | | | | |
| 459 a-d | " | | T3 | | | | |
| 460 a-d | " | | T9 | | | | |
| 461 a-d | " | | T10 | | | | |
| 462 a-d | " | | T11 | | | | |
| 463 a-d | " | | T14 | | | | |
| 464 a-d | " | | T16 | | | | |
| 465 a-d | " | | T17 | | | | |
| 466 a-d | tetrahydrothiopyran-SO$_2$ | | T1 | | | | |
| 467 a-d | " | | T2 | | | | |
| 468 a-d | " | | T3 | | | | |
| 469 a-d | " | | T9 | | | | |
| 470 a-d | " | | T10 | | | | |
| 471 a-d | " | | T11 | | | | |

TABLE 1-continued

Compounds of the formulae (Ia), (Ib), (Ic) and (Id)

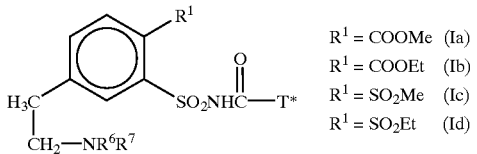

$R^1$ = COOMe (Ia)
$R^1$ = COOEt (Ib)
$R^1$ = SO$_2$Me (Ic)
$R^1$ = SO$_2$Et (Id)

| Ex. No. | R$^6$ | R$^7$ | T* | (Ia) | (Ib) | (Ic) | (Id) |
|---|---|---|---|---|---|---|---|
| 472 a–d | | " | T14 | | | | |
| 473 a–d | | " | T16 | | | | |
| 474 a–d | | " | T17 | | | | |
| 475 a–d | | | T1 | | | | |
| 476 a–d | | " | T2 | | | | |
| 477 a–d | | " | T3 | | | | |
| 478 a–d | | " | T9 | | | | |
| 479 a–d | | " | T10 | | | | |
| 480 a–d | | " | T11 | | | | |
| 481 a–d | | " | T14 | | | | |
| 482 a–d | | " | T16 | | | | |
| 483 a–d | | " | T17 | | | | |
| 484 a–d | H | COSMe | T1 | | | | |
| 485 a–d | H | COSMe | T2 | | | | |
| 486 a–d | H | COSMe | T3 | | | | |
| 487 a–d | H | COSMe | T9 | | | | |
| 488 a–d | H | COSMe | T10 | | | | |
| 489 a–d | H | COSMe | T11 | | | | |
| 490 a–d | H | COSMe | T14 | | | | |
| 491 a–d | H | COSMe | T16 | | | | |
| 492 a–d | H | COSMe | T17 | | | | |
| 493 a–d | H | CSOMe | T1 | | | | |
| 494 a–d | H | CSOMe | T2 | | | | |
| 495 a–d | H | CSOMe | T3 | | | | |
| 496 a–d | H | CSOMe | T9 | | | | |
| 497 a–d | H | CSOMe | T10 | | | | |
| 498 a–d | H | CSOMe | T11 | | | | |
| 499 a–d | H | CSOMe | T14 | | | | |
| 500 a–d | H | CSOMe | T16 | | | | |
| 501 a–d | H | CSOMe | T17 | | | | |
| 502 a–d | H | CSSMe | T1 | | | | |
| 503 a–d | H | CSSMe | T2 | | | | |
| 504 a–d | H | CSSMe | T3 | | | | |
| 505 a–d | H | CSSMe | T9 | | | | |
| 506 a–d | H | CSSMe | T10 | | | | |
| 507 a–d | H | CSSMe | T11 | | | | |
| 508 a–d | H | CSSMe | T14 | | | | |
| 509 a–d | H | CSSMe | T16 | | | | |
| 510 a–d | H | CSSMe | T17 | | | | |
| 511 a–d | H | COCOOMe | T1 | | | | |
| 512 a–d | H | COCOOMe | T2 | | | | |
| 513 a–d | H | COCOOMe | T3 | | | | |
| 514 a–d | H | COCOOMe | T9 | | | | |
| 515 a–d | H | COCOOMe | T10 | | | | |
| 516 a–d | H | COCOOMe | T11 | | | | |
| 517 a–d | H | COCOOMe | T14 | | | | |
| 518 a–d | H | COCOOMe | T16 | | | | |
| 519 a–d | H | COCOOMe | T17 | | | | |
| 520 a–d | H | i-C$_3$H$_7$OCO | T1 | | | | |
| 521 a–d | H | i-C$_3$H$_7$OCO | T2 | | | | |
| 522 a–d | H | i-C$_3$H$_7$OCO | T3 | | | | |
| 523 a–d | H | i-C$_3$H$_7$OCO | T9 | | | | |
| 524 a–d | H | i-C$_3$H$_7$OCO | T10 | | | | |
| 525 a–d | H | i-C$_3$H$_7$OCO | T11 | | | | |
| 526 a–d | H | i-C$_3$H$_7$OCO | T14 | | | | |
| 527 a–d | H | i-C$_3$H$_7$OCO | T16 | | | | |
| 528 a–d | H | i-C$_3$H$_7$OCO | T17 | | | | |
| 529 a–d | H | CHO | T1 | Na salt 75–77 | | | |
| 530 a–d | H | Me$_2$CHCO | T1 | Na salt | | | |

TABLE 1-continued

Compounds of the formulae (Ia), (Ib), (Ic) and (Id)

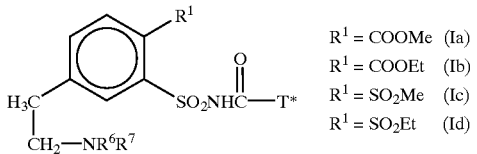

R$^1$ = COOMe (Ia)
R$^1$ = COOEt (Ib)
R$^1$ = SO$_2$Me (Ic)
R$^1$ = SO$_2$Et (Id)

| Ex. No. | R$^6$ | R$^7$ | T* | (Ia) | (Ib) | (Ic) | (Id) |
|---|---|---|---|---|---|---|---|
| 531 a-d | H | SO$_2$Et | T1 | 179–183 Na salt 154–160 | | | |
| 532 a-d | Me | CHO | T1 | 179–181 | | | |
| 533 a-d | Me | CHO | T2 | | | | |
| 534 a-d | Me | CHO | T3 | | | | |
| 535 a-d | Me | CHO | T4 | | | | |
| 536 a-d | Me | CHO | T5 | | | | |
| 537 a-d | Me | CHO | T6 | | | | |
| 538 a-d | Me | CHO | T7 | | | | |
| 539 a-d | Me | CHO | T8 | | | | |
| 540 a-d | Me | CHO | T9 | | | | |
| 541 a-d | Me | CHO | T10 | | | | |
| 542 a-d | Me | CHO | T11 | | | | |
| 543 a-d | Me | CHO | T12 | | | | |
| 544 a-d | Me | CHO | T13 | | | | |
| 545 a-d | Me | CHO | T14 | | | | |
| 546 a-d | Me | CHO | T15 | | | | |
| 547 a-d | Me | CHO | T16 | | | | |
| 548 a-d | Me | CHO | T17 | | | | |
| 549 a-d | Me | COCH$_3$ | T1 | 217–218 | | | |
| 550 a-d | Me | COCH$_3$ | T2 | | | | |
| 551 a-d | Me | COCH$_3$ | T3 | | | | |
| 552 a-d | Me | COCH$_3$ | T4 | | | | |
| 553 a-d | Me | COCH$_3$ | T5 | | | | |
| 554 a-d | Me | COCH$_3$ | T6 | | | | |
| 555 a-d | Me | COCH$_3$ | T7 | | | | |
| 556 a-d | Me | COCH$_3$ | T8 | | | | |
| 557 a-d | Me | COCH$_3$ | T9 | | | | |
| 558 a-d | Me | COCH$_3$ | T10 | | | | |
| 559 a-d | Me | COCH$_3$ | T11 | | | | |
| 560 a-d | Me | COCH$_3$ | T12 | | | | |
| 561 a-d | Me | COCH$_3$ | T13 | | | | |
| 562 a-d | Me | COCH$_3$ | T14 | | | | |
| 563 a-d | Me | COCH$_3$ | T15 | | | | |
| 564 a-d | Me | COCH$_3$ | T16 | | | | |
| 565 a-d | Me | COCH$_3$ | T17 | | | | |
| 566 a-d | Me | COEt | T1 | 163–165 | | | |
| 567 a-d | Me | COEt | T2 | | | | |
| 568 a-d | Me | COEt | T3 | | | | |
| 569 a-d | Me | COEt | T4 | | | | |
| 570 a-d | Me | COEt | T5 | | | | |
| 571 a-d | Me | COEt | T6 | | | | |
| 572 a-d | Me | COEt | T7 | | | | |
| 573 a-d | Me | COEt | T8 | | | | |
| 574 a-d | Me | COEt | T9 | | | | |
| 575 a-d | Me | COEt | T10 | | | | |
| 576 a-d | Me | COEt | T11 | | | | |
| 577 a-d | Me | COEt | T12 | | | | |
| 578 a-d | Me | COEt | T13 | | | | |
| 579 a-d | Me | COEt | T14 | | | | |
| 580 a-d | Me | COEt | T15 | | | | |
| 581 a-d | Me | COEt | T16 | | | | |
| 582 a-d | Me | COEt | T17 | | | | |
| 583 a-d | Me | CO$_n$C$_3$H$_7$ | T1 | | | | |
| 584 a-d | Me | CO$_n$C$_3$H$_7$ | T2 | | | | |
| 585 a-d | Me | CO$_n$C$_3$H$_7$ | T3 | | | | |
| 586 a-d | Me | CO$_n$C$_3$H$_7$ | T4 | | | | |
| 587 a-d | Me | CO$_n$C$_3$H$_7$ | T5 | | | | |
| 588 a-d | Me | CO$_n$C$_3$H$_7$ | T6 | | | | |
| 589 a-d | Me | CO$_n$C$_3$H$_7$ | T7 | | | | |
| 590 a-d | Me | CO$_n$C$_3$H$_7$ | T8 | | | | |
| 591 a-d | Me | CO$_n$C$_3$H$_7$ | T9 | | | | |
| 592 a-d | Me | CO$_n$C$_3$H$_7$ | T10 | | | | |
| 593 a-d | Me | CO$_n$C$_3$H$_7$ | T11 | | | | |
| 594 a-d | Me | CO$_n$C$_3$H$_7$ | T12 | | | | |

TABLE 1-continued

Compounds of the formulae (Ia), (Ib), (Ic) and (Id)

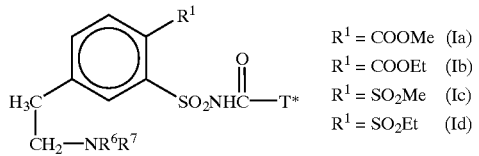

R¹ = COOMe (Ia)
R¹ = COOEt (Ib)
R¹ = SO₂Me (Ic)
R¹ = SO₂Et (Id)

| Ex. No. | R⁶ | R⁷ | T* | (Ia) | (Ib) | (Ic) | (Id) |
|---|---|---|---|---|---|---|---|
| 595 a–d | Me | CO$_n$C$_3$H$_7$ | T13 | | | | |
| 596 a–d | Me | CO$_n$C$_3$H$_7$ | T14 | | | | |
| 597 a–d | Me | CO$_n$C$_3$H$_7$ | T15 | | | | |
| 598 a–d | Me | CO$_n$C$_3$H$_7$ | T16 | | | | |
| 599 a–d | Me | CO$_n$C$_3$H$_7$ | T17 | | | | |
| 600 a–d | Me | CO-i-C$_3$H$_7$ | T1 | | | | |
| 601 a–d | Me | CO-i-C$_3$H$_7$ | T2 | | | | |
| 602 a–d | Me | CO-i-C$_3$H$_7$ | T3 | | | | |
| 603 a–d | Me | CO-i-C$_3$H$_7$ | T4 | | | | |
| 604 a–d | Me | CO-i-C$_3$H$_7$ | T5 | | | | |
| 605 a–d | Me | CO-i-C$_3$H$_7$ | T6 | | | | |
| 606 a–d | Me | CO-i-C$_3$H$_7$ | T7 | | | | |
| 607 a–d | Me | CO-i-C$_3$H$_7$ | T8 | | | | |
| 608 a–d | Me | CO-i-C$_3$H$_7$ | T9 | | | | |
| 609 a–d | Me | CO-i-C$_3$H$_7$ | T10 | | | | |
| 610 a–d | Me | CO-i-C$_3$H$_7$ | T11 | | | | |
| 611 a–d | Me | CO-i-C$_3$H$_7$ | T12 | | | | |
| 612 a–d | Me | CO-i-C$_3$H$_7$ | T13 | | | | |
| 613 a–d | Me | CO-i-C$_3$H$_7$ | T14 | | | | |
| 614 a–d | Me | CO-i-C$_3$H$_7$ | T15 | | | | |
| 615 a–d | Me | CO-i-C$_3$H$_7$ | T16 | | | | |
| 616 a–d | Me | CO-i-C$_3$H$_7$ | T17 | | | | |
| 617 a–d | Me | COCF$_3$ | T1 | | | | |
| 618 a–d | Me | COCF$_3$ | T2 | | | | |
| 619 a–d | Me | COCF$_3$ | T3 | | | | |
| 620 a–d | Me | COCF$_3$ | T4 | | | | |
| 621 a–d | Me | COCF$_3$ | T5 | | | | |
| 622 a–d | Me | COCF$_3$ | T6 | | | | |
| 623 a–d | Me | COCF$_3$ | T7 | | | | |
| 624 a–d | Me | COCF$_3$ | T8 | | | | |
| 625 a–d | Me | COCF$_3$ | T9 | | | | |
| 626 a–d | Me | COCF$_3$ | T10 | | | | |
| 627 a–d | Me | COCF$_3$ | T11 | | | | |
| 628 a–d | Me | COCF$_3$ | T12 | | | | |
| 629 a–d | Me | COCF$_3$ | T13 | | | | |
| 630 a–d | Me | COCF$_3$ | T14 | | | | |
| 631 a–d | Me | COCF$_3$ | T15 | | | | |
| 632 a–d | Me | COCF$_3$ | T16 | | | | |
| 633 a–d | Me | COCF$_3$ | T17 | | | | |
| 634 a–d | Me | COOMe | T1 | 181–183 | | | |
| 635 a–d | Me | COOMe | T2 | | | | |
| 636 a–d | Me | COOMe | T3 | | | | |
| 637 a–d | Me | COOMe | T4 | | | | |
| 638 a–d | Me | COOMe | T5 | | | | |
| 639 a–d | Me | COOMe | T6 | | | | |
| 640 a–d | Me | COOMe | T7 | | | | |
| 641 a–d | Me | COOMe | T8 | | | | |
| 642 a–d | Me | COOMe | T9 | | | | |
| 643 a–d | Me | COOMe | T10 | | | | |
| 644 a–d | Me | COOMe | T11 | | | | |
| 645 a–d | Me | COOMe | T12 | | | | |
| 646 a–d | Me | COOMe | T13 | | | | |
| 647 a–d | Me | COOMe | T14 | | | | |
| 648 a–d | Me | COOMe | T15 | | | | |
| 649 a–d | Me | COOMe | T16 | | | | |
| 650 a–d | Me | COOMe | T17 | | | | |
| 651 a–d | Me | COOEt | T1 | | | | |
| 652 a–d | Me | COOEt | T2 | | | | |
| 653 a–d | Me | COOEt | T3 | | | | |
| 654 a–d | Me | COOEt | T4 | | | | |
| 655 a–d | Me | COOEt | T5 | | | | |
| 656 a–d | Me | COOEt | T6 | | | | |
| 657 a–d | Me | COOEt | T7 | | | | |
| 658 a–d | Me | COOEt | T8 | | | | |
| 659 a–d | Me | COOEt | T9 | | | | |
| 660 a–d | Me | COOEt | T10 | | | | |

TABLE 1-continued

Compounds of the formulae (Ia), (Ib), (Ic) and (Id)

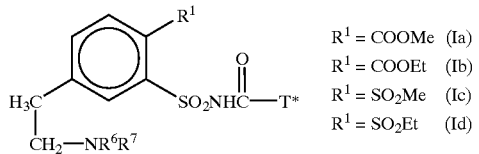

R¹ = COOMe (Ia)
R¹ = COOEt (Ib)
R¹ = SO₂Me (Ic)
R¹ = SO₂Et (Id)

| Ex. No. | R⁶ | R⁷ | T* | (Ia) | (Ib) | (Ic) | (Id) |
|---|---|---|---|---|---|---|---|
| 661 a-d | Me | COOEt | T11 | | | | |
| 662 a-d | Me | COOEt | T12 | | | | |
| 663 a-d | Me | COOEt | T13 | | | | |
| 664 a-d | Me | COOEt | T14 | | | | |
| 665 a-d | Me | COOEt | T15 | | | | |
| 666 a-d | Me | COOEt | T16 | | | | |
| 667 a-d | Me | COOEt | T17 | | | | |
| 668 a-d | Me | SO₂CH₃ | T1 | 201–203 | | | |
| 669 a-d | Me | SO₂CH₃ | T2 | | | | |
| 670 a-d | Me | SO₂CH₃ | T3 | | | | |
| 671 a-d | Me | SO₂CH₃ | T4 | | | | |
| 672 a-d | Me | SO₂CH₃ | T5 | | | | |
| 673 a-d | Me | SO₂CH₃ | T6 | | | | |
| 674 a-d | Me | SO₂CH₃ | T7 | | | | |
| 675 a-d | Me | SO₂CH₃ | T8 | | | | |
| 676 a-d | Me | SO₂CH₃ | T9 | | | | |
| 677 a-d | Me | SO₂CH₃ | T10 | | | | |
| 678 a-d | Me | SO₂CH₃ | T11 | | | | |
| 679 a-d | Me | SO₂CH₃ | T12 | | | | |
| 680 a-d | Me | SO₂CH₃ | T13 | | | | |
| 681 a-d | Me | SO₂CH₃ | T14 | | | | |
| 682 a-d | Me | SO₂CH₃ | T15 | | | | |
| 683 a-d | Me | SO₂CH₃ | T16 | | | | |
| 684 a-d | Me | SO₂CH₃ | T17 | | | | |
| 685 a-d | Me | SO₂Et | T1 | 149–151 | | | |
| 686 a-d | Me | SO₂Et | T2 | | | | |
| 687 a-d | Me | SO₂Et | T3 | | | | |
| 688 a-d | Me | SO₂Et | T4 | | | | |
| 689 a-d | Me | SO₂Et | T5 | | | | |
| 690 a-d | Me | SO₂Et | T6 | | | | |
| 691 a-d | Me | SO₂Et | T7 | | | | |
| 692 a-d | Me | SO₂Et | T8 | | | | |
| 693 a-d | Me | SO₂Et | T9 | | | | |
| 694 a-d | Me | SO₂Et | T10 | | | | |
| 695 a-d | Me | SO₂Et | T11 | | | | |
| 696 a-d | Me | SO₂Et | T12 | | | | |
| 697 a-d | Me | SO₂Et | T13 | | | | |
| 698 a-d | Me | SO₂Et | T14 | | | | |
| 699 a-d | Me | SO₂Et | T15 | | | | |
| 700 a-d | Me | SO₂Et | T16 | | | | |
| 701 a-d | Me | SO₂Et | T17 | | | | |
| 702 a-d | Me | SO₂nPr | T1 | | | | |
| 703 a-d | Me | SO₂nPr | T2 | | | | |
| 704 a-d | Me | SO₂nPr | T3 | | | | |
| 705 a-d | Me | SO₂nPr | T4 | | | | |
| 706 a-d | Me | SO₂nPr | T5 | | | | |
| 707 a-d | Me | SO₂nPr | T6 | | | | |
| 708 a-d | Me | SO₂nPr | T7 | | | | |
| 709 a-d | Me | SO₂nPr | T8 | | | | |
| 710 a-d | Me | SO₂nPr | T9 | | | | |
| 711 a-d | Me | SO₂nPr | T10 | | | | |
| 712 a-d | Me | SO₂nPr | T11 | | | | |
| 713 a-d | Me | SO₂nPr | T12 | | | | |
| 714 a-d | Me | SO₂nPr | T13 | | | | |
| 715 a-d | Me | SO₂nPr | T14 | | | | |
| 716 a-d | Me | SO₂nPr | T15 | | | | |
| 717 a-d | Me | SO₂nPr | T16 | | | | |
| 718 a-d | Me | SO₂nPr | T17 | | | | |
| 719 a-d | Me | SO₂iPr | T1 | | | | |
| 720 a-d | Me | SO₂iPr | T2 | | | | |
| 721 a-d | Me | SO₂iPr | T3 | | | | |
| 722 a-d | Me | SO₂iPr | T4 | | | | |
| 723 a-d | Me | SO₂iPr | T5 | | | | |
| 724 a-d | Me | SO₂iPr | T6 | | | | |
| 725 a-d | Me | SO₂iPr | T7 | | | | |
| 726 a-d | Me | SO₂iPr | T8 | | | | |

TABLE 1-continued

Compounds of the formulae (Ia), (Ib), (Ic) and (Id)

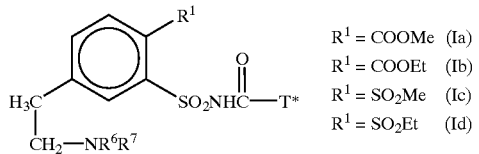

R¹ = COOMe (Ia)
R¹ = COOEt (Ib)
R¹ = SO₂Me (Ic)
R¹ = SO₂Et (Id)

| Ex. No. | R⁶ | R⁷ | T* | (Ia) | (Ib) | (Ic) | (Id) |
|---|---|---|---|---|---|---|---|
| 727 a–d | Me | SO₂iPr | T9 | | | | |
| 728 a–d | Me | SO₂iPr | T10 | | | | |
| 729 a–d | Me | SO₂iPr | T11 | | | | |
| 730 a–d | Me | SO₂iPr | T12 | | | | |
| 731 a–d | Me | SO₂iPr | T13 | | | | |
| 732 a–d | Me | SO₂iPr | T14 | | | | |
| 733 a–d | Me | SO₂iPr | T15 | | | | |
| 734 a–d | Me | SO₂iPr | T16 | | | | |
| 735 a–d | Me | SO₂iPr | T17 | | | | |
| 736 a–d | Me | ClCH₂CO | T1 | | | | |
| 737 a–d | Me | ClCH₂CO | T2 | | | | |
| 738 a–d | Me | ClCH₂CO | T3 | | | | |
| 739 a–d | Me | ClCH₂CO | T9 | | | | |
| 740 a–d | Me | ClCH₂CO | T10 | | | | |
| 741 a–d | Me | ClCH₂CO | T11 | | | | |
| 742 a–d | Me | ClCH₂CO | T14 | | | | |
| 743 a–d | Me | ClCH₂CO | T16 | | | | |
| 744 a–d | Me | ClCH₂CO | T17 | | | | |
| 745 a–d | Me | Cl₂CHCO | T1 | | | | |
| 746 a–d | Me | Cl₂CHCO | T2 | | | | |
| 747 a–d | Me | Cl₂CHCO | T3 | | | | |
| 748 a–d | Me | Cl₂CHCO | T9 | | | | |
| 749 a–d | Me | Cl₂CHCO | T10 | | | | |
| 750 a–d | Me | Cl₂CHCO | T11 | | | | |
| 751 a–d | Me | Cl₂CHCO | T14 | | | | |
| 752 a–d | Me | Cl₂CHCO | T16 | | | | |
| 753 a–d | Me | Cl₂CHCO | T17 | | | | |
| 754 a–d | Me | Cl₃CCO | T1 | | | | |
| 755 a–d | Me | Cl₃CCO | T2 | | | | |
| 756 a–d | Me | Cl₃CCO | T3 | | | | |
| 757 a–d | Me | Cl₃CCO | T9 | | | | |
| 758 a–d | Me | Cl₃CCO | T10 | | | | |
| 759 a–d | Me | Cl₃CCO | T11 | | | | |
| 760 a–d | Me | Cl₃CCO | T14 | | | | |
| 761 a–d | Me | Cl₃CCO | T16 | | | | |
| 762 a–d | Me | Cl₃CCO | T17 | | | | |
| 763 a–d | Me | CH₃OCH₂CO | T1 | | | | |
| 764 a–d | Me | CH₃OCH₂CO | T2 | | | | |
| 765 a–d | Me | CH₃OCH₂CO | T3 | | | | |
| 766 a–d | Me | CH₃OCH₂CO | T9 | | | | |
| 767 a–d | Me | CH₃OCH₂CO | T10 | | | | |
| 768 a–d | Me | CH₃OCH₂CO | T11 | | | | |
| 769 a–d | Me | CH₃OCH₂CO | T14 | | | | |
| 770 a–d | Me | CH₃OCH₂CO | T16 | | | | |
| 771 a–d | Me | CH₃OCH₂CO | T17 | | | | |
| 772 a–d | Me | CH₂=CHCO | T1 | | | | |
| 773 a–d | Me | CH₂=CHCO | T2 | | | | |
| 774 a–d | Me | CH₂=CHCO | T3 | | | | |
| 775 a–d | Me | CH₂=CHCO | T9 | | | | |
| 776 a–d | Me | CH₂=CHCO | T10 | | | | |
| 777 a–d | Me | CH₂=CHCO | T11 | | | | |
| 778 a–d | Me | CH₂=CHCO | T14 | | | | |
| 779 a–d | Me | CH₂=CHCO | T16 | | | | |
| 780 a–d | Me | CH₂=CHCO | T17 | | | | |
| 781 a–d | Me | CH≡CCO | T1 | | | | |
| 782 a–d | Me | CH≡CCO | T2 | | | | |
| 783 a–d | Me | CH≡CCO | T3 | | | | |
| 784 a–d | Me | CH≡CCO | T9 | | | | |
| 785 a–d | Me | CH≡CCO | T10 | | | | |
| 786 a–d | Me | CH≡CCO | T11 | | | | |
| 787 a–d | Me | CH≡CCO | T14 | | | | |
| 788 a–d | Me | CH≡CCO | T16 | | | | |
| 789 a–d | Me | CH≡CCO | T17 | | | | |

TABLE 1-continued

Compounds of the formulae (Ia), (Ib), (Ic) and (Id)

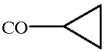

R¹ = COOMe (Ia)
R¹ = COOEt (Ib)
R¹ = SO₂Me (Ic)
R¹ = SO₂Et (Id)

| Ex. No. | R⁶ | R⁷ | T* | (Ia) | (Ib) | (Ic) | (Id) |
|---|---|---|---|---|---|---|---|
| 790 a-d | Me | CO-△ | T1 | | | | |
| 791 a-d | Me | " | T2 | | | | |
| 792 a-d | Me | " | T3 | | | | |
| 793 a-d | Me | " | T9 | | | | |
| 794 a-d | Me | " | T10 | | | | |
| 795 a-d | Me | " | T11 | | | | |
| 796 a-d | Me | " | T14 | | | | |
| 797 a-d | Me | " | T16 | | | | |
| 798 a-d | Me | " | T17 | | | | |
| 799 a-d | Me | CO-◇ | T1 | | | | |
| 800 a-d | Me | " | T2 | | | | |
| 801 a-d | Me | " | T3 | | | | |
| 802 a-d | Me | " | T9 | | | | |
| 803 a-d | Me | " | T10 | | | | |
| 804 a-d | Me | " | T11 | | | | |
| 805 a-d | Me | " | T14 | | | | |
| 806 a-d | Me | " | T16 | | | | |
| 807 a-d | Me | " | T17 | | | | |
| 808 a-d | Me | CO-⬠ | T1 | | | | |
| 809 a-d | Me | " | T2 | | | | |
| 810 a-d | Me | " | T3 | | | | |
| 811 a-d | Me | " | T9 | | | | |
| 812 a-d | Me | " | T10 | | | | |
| 813 a-d | Me | " | T11 | | | | |
| 814 a-d | Me | " | T14 | | | | |
| 815 a-d | Me | " | T16 | | | | |
| 816 a-d | Me | " | T17 | | | | |
| 817 a-d | Me | CO-⬡ | T1 | | | | |
| 818 a-d | Me | " | T2 | | | | |
| 819 a-d | Me | " | T3 | | | | |
| 820 a-d | Me | " | T9 | | | | |
| 821 a-d | Me | " | T10 | | | | |
| 822 a-d | Me | " | T11 | | | | |
| 823 a-d | Me | " | T14 | | | | |
| 824 a-d | Me | " | T16 | | | | |
| 825 a-d | Me | " | T17 | | | | |
| 826 a-d | Me | SO₂CF₃ | T1 | | | | |
| 827 a-d | Me | SO₂CF₃ | T2 | | | | |
| 828 a-d | Me | SO₂CF₃ | T3 | | | | |
| 829 a-d | Me | SO₂CF₃ | T9 | | | | |
| 830 a-d | Me | SO₂CF₃ | T10 | | | | |
| 831 a-d | Me | SO₂CF₃ | T11 | | | | |
| 832 a-d | Me | SO₂CF₃ | T14 | | | | |
| 833 a-d | Me | SO₂CF₃ | T16 | | | | |
| 834 a-d | Me | SO₂CF₃ | T17 | | | | |
| 835 a-d | Me | SO₂CH₂F | T1 | 164–166 | | | |
| 836 a-d | Me | SO₂CH₂F | T2 | | | | |
| 837 a-d | Me | SO₂CH₂F | T3 | | | | |
| 838 a-d | Me | SO₂CH₂F | T9 | | | | |

TABLE 1-continued

Compounds of the formulae (Ia), (Ib), (Ic) and (Id)

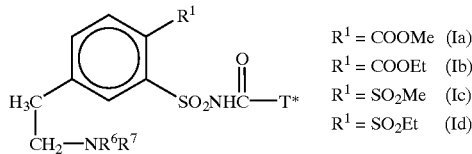

R¹ = COOMe (Ia)
R¹ = COOEt (Ib)
R¹ = SO₂Me (Ic)
R¹ = SO₂Et (Id)

| Ex. No. | R⁶ | R⁷ | T* | (Ia) | (Ib) | (Ic) | (Id) |
|---|---|---|---|---|---|---|---|
| 839 a-d | Me | SO₂CH₂F | T10 | | | | |
| 840 a-d | Me | SO₂CH₂F | T11 | | | | |
| 841 a-d | Me | SO₂CH₂F | T14 | | | | |
| 842 a-d | Me | SO₂CH₂F | T16 | | | | |
| 843 a-d | Me | SO₂CH₂F | T17 | | | | |
| 844 a-d | Me | SO₂CH₂Cl | T1 | | | | |
| 845 a-d | Me | SO₂CH₂Cl | T2 | | | | |
| 846 a-d | Me | SO₂CH₂Cl | T3 | | | | |
| 847 a-d | Me | SO₂CH₂Cl | T9 | | | | |
| 848 a-d | Me | SO₂CH₂Cl | T10 | | | | |
| 849 a-d | Me | SO₂CH₂Cl | T11 | | | | |
| 850 a-d | Me | SO₂CH₂Cl | T14 | | | | |
| 851 a-d | Me | SO₂CH₂Cl | T16 | | | | |
| 852 a-d | Me | SO₂CH₂Cl | T17 | | | | |
| 853 a-d | Me | SO₂CHCl₂ | T1 | | | | |
| 854 a-d | Me | SO₂CHCl₂ | T2 | | | | |
| 855 a-d | Me | SO₂CHCl₂ | T3 | | | | |
| 856 a-d | Me | SO₂CHCl₂ | T9 | | | | |
| 857 a-d | Me | SO₂CHCl₂ | T10 | | | | |
| 858 a-d | Me | SO₂CHCl₂ | T11 | | | | |
| 859 a-d | Me | SO₂CHCl₂ | T14 | | | | |
| 860 a-d | Me | SO₂CHCl₂ | T16 | | | | |
| 861 a-d | Me | SO₂CHCl₂ | T17 | | | | |
| 862 a-d | Me | SO₂CCl₃ | T1 | | | | |
| 863 a-d | Me | SO₂CCl₃ | T2 | | | | |
| 864 a-d | Me | SO₂CCl₃ | T3 | | | | |
| 865 a-d | Me | SO₂CCl₃ | T9 | | | | |
| 866 a-d | Me | SO₂CCl₃ | T10 | | | | |
| 867 a-d | Me | SO₂CCl₃ | T11 | | | | |
| 868 a-d | Me | SO₂CCl₃ | T14 | | | | |
| 869 a-d | Me | SO₂CCl₃ | T16 | | | | |
| 870 a-d | Me | SO₂CCl₃ | T17 | | | | |
| 871 a-d | Me | SO₂nBu | T1 | | | | |
| 872 a-d | Me | SO₂nBu | T2 | | | | |
| 873 a-d | Me | SO₂nBu | T3 | | | | |
| 874 a-d | Me | SO₂nBu | T9 | | | | |
| 875 a-d | Me | SO₂nBu | T10 | | | | |
| 876 a-d | Me | SO₂nBu | T11 | | | | |
| 877 a-d | Me | SO₂nBu | T14 | | | | |
| 878 a-d | Me | SO₂nBu | T16 | | | | |
| 879 a-d | Me | SO₂nBu | T17 | | | | |
| 880 a-d | Me | SO₂CH₂CF₃ | T1 | | | | |
| 881 a-d | Me | SO₂CH₂CF₃ | T2 | | | | |
| 882 a-d | Me | SO₂CH₂CF₃ | T3 | | | | |
| 883 a-d | Me | SO₂CH₂CF₃ | T9 | | | | |
| 884 a-d | Me | SO₂CH₂CF₃ | T10 | | | | |
| 885 a-d | Me | SO₂CH₂CF₃ | T11 | | | | |
| 886 a-d | Me | SO₂CH₂CF₃ | T14 | | | | |
| 887 a-d | Me | SO₂CH₂CF₃ | T16 | | | | |
| 888 a-d | Me | SO₂CH₂CF₃ | T17 | | | | |
| 889 a-d | Me | SO₂NHCH₃ | T1 | | | | |
| 890 a-d | Me | SO₂NHCH₃ | T2 | | | | |
| 891 a-d | Me | SO₂NHCH₃ | T3 | | | | |
| 892 a-d | Me | SO₂NHCH₃ | T9 | | | | |
| 893 a-d | Me | SO₂NHCH₃ | T10 | | | | |
| 894 a-d | Me | SO₂NHCH₃ | T11 | | | | |
| 895 a-d | Me | SO₂NHCH₃ | T14 | | | | |
| 896 a-d | Me | SO₂NHCH₃ | T16 | | | | |
| 897 a-d | Me | SO₂NHCH₃ | T17 | | | | |
| 898 a-d | Me | SO₂N(CH₃)₂ | T1 | | | | |
| 899 a-d | Me | SO₂N(CH₃)₂ | T2 | | | | |
| 900 a-d | Me | SO₂N(CH₃)₂ | T3 | | | | |
| 901 a-d | Me | SO₂N(CH₃)₂ | T9 | | | | |
| 902 a-d | Me | SO₂N(CH₃)₂ | T10 | | | | |
| 903 a-d | Me | SO₂N(CH₃)₂ | T11 | | | | |
| 904 a-d | Me | SO₂N(CH₃)₂ | T14 | | | | |

TABLE 1-continued

Compounds of the formulae (Ia), (Ib), (Ic) and (Id)

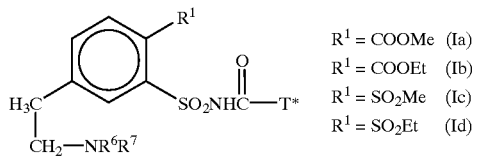

R¹ = COOMe (Ia)
R¹ = COOEt (Ib)
R¹ = SO₂Me (Ic)
R¹ = SO₂Et (Id)

| Ex. No. | R⁶ | R⁷ | T* | (Ia) | (Ib) | (Ic) | (Id) |
|---|---|---|---|---|---|---|---|
| 905 a-d | Me | SO₂N(CH₃)₂ | T16 | | | | |
| 906 a-d | Me | SO₂N(CH₃)₂ | T17 | | | | |
| 907 a-d | Me | (CH₃)₃COCO | T1 | | | | |
| 908 a-d | Me | (CH₃)₃COCO | T2 | | | | |
| 909 a-d | Me | (CH₃)₃COCO | T3 | | | | |
| 910 a-d | Me | (CH₃)₃COCO | T9 | | | | |
| 911 a-d | Me | (CH₃)₃COCO | T10 | | | | |
| 912 a-d | Me | (CH₃)₃COCO | T11 | | | | |
| 913 a-d | Me | (CH₃)₃COCO | T14 | | | | |
| 914 a-d | Me | (CH₃)₃COCO | T16 | | | | |
| 915 a-d | Me | (CH₃)₃COCO | T17 | | | | |
| 916 a-d | Me | PhCO | T1 | | | | |
| 917 a-d | Me | PhCO | T2 | | | | |
| 918 a-d | Me | PhCO | T3 | | | | |
| 919 a-d | Me | PhCO | T9 | | | | |
| 920 a-d | Me | PhCO | T10 | | | | |
| 921 a-d | Me | PhCO | T11 | | | | |
| 922 a-d | Me | PhCO | T14 | | | | |
| 923 a-d | Me | PhCO | T16 | | | | |
| 924 a-d | Me | PhCO | T17 | | | | |
| 925 a-d | Me | PhSO₂ | T1 | | | | |
| 926 a-d | Me | PhSO₂ | T2 | | | | |
| 927 a-d | Me | PhSO₂ | T3 | | | | |
| 928 a-d | Me | PhSO₂ | T9 | | | | |
| 929 a-d | Me | PhSO₂ | T10 | | | | |
| 930 a-d | Me | PhSO₂ | T11 | | | | |
| 931 a-d | Me | PhSO₂ | T14 | | | | |
| 932 a-d | Me | PhSO₂ | T16 | | | | |
| 933 a-d | Me | PhSO₂ | T17 | | | | |
| 934 a-d | Me | MeNHCO | T1 | | | | |
| 935 a-d | Me | MeNHCO | T2 | | | | |
| 936 a-d | Me | MeNHCO | T3 | | | | |
| 937 a-d | Me | MeNHCO | T9 | | | | |
| 938 a-d | Me | MeNHCO | T10 | | | | |
| 939 a-d | Me | MeNHCO | T11 | | | | |
| 940 a-d | Me | MeNHCO | T14 | | | | |
| 941 a-d | Me | MeNHCO | T16 | | | | |
| 942 a-d | Me | MeNHCO | T17 | | | | |
| 943 a-d | Me | EtNHCO | T1 | | | | |
| 944 a-d | Me | EtNHCO | T2 | | | | |
| 945 a-d | Me | EtNHCO | T3 | | | | |
| 946 a-d | Me | EtNHCO | T9 | | | | |
| 947 a-d | Me | EtNHCO | T10 | | | | |
| 948 a-d | Me | EtNHCO | T11 | | | | |
| 949 a-d | Me | EtNHCO | T14 | | | | |
| 950 a-d | Me | EtNHCO | T16 | | | | |
| 951 a-d | Me | EtNHCO | T17 | | | | |
| 952 a-d | Me | MeNHCS | T1 | | | | |
| 953 a-d | Me | MeNHCS | T2 | | | | |
| 954 a-d | Me | MeNHCS | T3 | | | | |
| 955 a-d | Me | MeNHCS | T9 | | | | |
| 956 a-d | Me | MeNHCS | T10 | | | | |
| 957 a-d | Me | MeNHCS | T11 | | | | |
| 958 a-d | Me | MeNHCS | T14 | | | | |
| 959 a-d | Me | MeNHCS | T16 | | | | |
| 960 a-d | Me | MeNHCS | T17 | | | | |
| 961 a-d | Me | EtNHCS | T1 | | | | |
| 962 a-d | Me | EtNHCS | T2 | | | | |
| 963 a-d | Me | EtNHCS | T3 | | | | |
| 964 a-d | Me | EtNHCS | T9 | | | | |
| 965 a-d | Me | EtNHCS | T10 | | | | |
| 966 a-d | Me | EtNHCS | T11 | | | | |
| 967 a-d | Me | EtNHCS | T14 | | | | |
| 968 a-d | Me | EtNHCS | T16 | | | | |
| 969 a-d | Me | EtNHCS | T17 | | | | |
| 970 a-d | Me | COSMe | T1 | | | | |

TABLE 1-continued

Compounds of the formulae (Ia), (Ib), (Ic) and (Id)

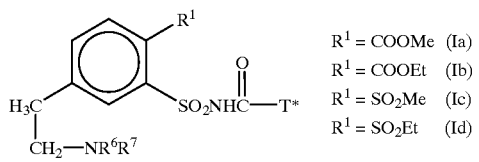

$R^1$ = COOMe (Ia)
$R^1$ = COOEt (Ib)
$R^1$ = SO$_2$Me (Ic)
$R^1$ = SO$_2$Et (Id)

| Ex. No. | R⁶ | R⁷ | T* | (Ia) | (Ib) | (Ic) | (Id) |
|---|---|---|---|---|---|---|---|
| 971 a-d | Me | COSMe | T2 | | | | |
| 972 a-d | Me | COSMe | T3 | | | | |
| 973 a-d | Me | COSMe | T9 | | | | |
| 974 a-d | Me | COSMe | T10 | | | | |
| 975 a-d | Me | COSMe | T11 | | | | |
| 976 a-d | Me | COSMe | T14 | | | | |
| 977 a-d | Me | COSMe | T16 | | | | |
| 978 a-d | Me | COSMe | T17 | | | | |
| 979 a-d | Me | CSOMe | T1 | | | | |
| 980 a-d | Me | CSOMe | T2 | | | | |
| 981 a-d | Me | CSOMe | T3 | | | | |
| 982 a-d | Me | CSOMe | T9 | | | | |
| 983 a-d | Me | CSOMe | T10 | | | | |
| 984 a-d | Me | CSOMe | T11 | | | | |
| 985 a-d | Me | CSOMe | T14 | | | | |
| 986 a-d | Me | CSOMe | T16 | | | | |
| 987 a-d | Me | CSOMe | T17 | | | | |
| 988 a-d | Me | CSSMe | T1 | | | | |
| 989 a-d | Me | CSSMe | T2 | | | | |
| 990 a-d | Me | CSSMe | T3 | | | | |
| 991 a-d | Me | CSSMe | T9 | | | | |
| 992 a-d | Me | CSSMe | T10 | | | | |
| 993 a-d | Me | CSSMe | T11 | | | | |
| 994 a-d | Me | CSSMe | T14 | | | | |
| 995 a-d | Me | CSSMe | T16 | | | | |
| 996 a-d | Me | CSSMe | T17 | | | | |
| 997 a-d | Me | COCOOMe | T1 | | | | |
| 998 a-d | Me | COCOOMe | T2 | | | | |
| 999 a-d | Me | COCOOMe | T3 | | | | |
| 1000 a-d | Me | COCOOMe | T9 | | | | |
| 1001 a-d | Me | COCOOMe | T10 | | | | |
| 1002 a-d | Me | COCOOMe | T11 | | | | |
| 1003 a-d | Me | COCOOMe | T14 | | | | |
| 1004 a-d | Me | COCOOMe | T16 | | | | |
| 1005 a-d | Me | COCOOMe | T17 | | | | |
| 1006 a-d | Me | i-PrOCO | T1 | | | | |
| 1007 a-d | Me | i-PrOCO | T2 | | | | |
| 1008 a-d | Me | i-PrOCO | T3 | | | | |
| 1009 a-d | Me | i-PrOCO | T9 | | | | |
| 1010 a-d | Me | i-PrOCO | T10 | | | | |
| 1011 a-d | Me | i-PrOCO | T11 | | | | |
| 1012 a-d | Me | i-PrOCO | T14 | | | | |
| 1013 a-d | Me | i-PrOCO | T16 | | | | |
| 1014 a-d | Me | i-PrOCO | T17 | | | | |
| 1015 a-d | Et | CHO | T1 | | | | |
| 1016 a-d | Et | CHO | T2 | | | | |
| 1017 a-d | Et | CHO | T3 | | | | |
| 1018 a-d | Et | CHO | T9 | | | | |
| 1019 a-d | Et | CHO | T10 | | | | |
| 1020 a-d | Et | CHO | T11 | | | | |
| 1021 a-d | Et | CHO | T14 | | | | |
| 1022 a-d | Et | CHO | T16 | | | | |

TABLE 1-continued

Compounds of the formulae (Ia), (Ib), (Ic) and (Id)

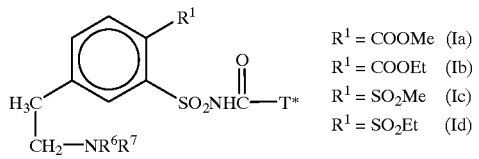

R$^1$ = COOMe (Ia)
R$^1$ = COOEt (Ib)
R$^1$ = SO$_2$Me (Ic)
R$^1$ = SO$_2$Et (Id)

| Ex. No. | R$^6$ | R$^7$ | T* | (Ia) | (Ib) | (Ic) | (Id) |
|---|---|---|---|---|---|---|---|
| 1023 a-d | Et | CHO | T17 | | | | |
| 1024 a-d | Et | COMe | T1 | | | | |
| 1025 a-d | Et | COMe | T2 | | | | |
| 1026 a-d | Et | COMe | T3 | | | | |
| 1027 a-d | Et | COMe | T9 | | | | |
| 1028 a-d | Et | COMe | T10 | | | | |
| 1029 a-d | Et | COMe | T11 | | | | |
| 1030 a-d | Et | COMe | T14 | | | | |
| 1031 a-d | Et | COMe | T16 | | | | |
| 1032 a-d | Et | COMe | T17 | | | | |
| 1033 a-d | Et | COOMe | T1 | | | | |
| 1034 a-d | Et | COOMe | T2 | | | | |
| 1035 a-d | Et | COOMe | T3 | | | | |
| 1036 a-d | Et | COOMe | T9 | | | | |
| 1037 a-d | Et | COOMe | T10 | | | | |
| 1038 a-d | Et | COOMe | T11 | | | | |
| 1039 a-d | Et | COOMe | T14 | | | | |
| 1040 a-d | Et | COOMe | T16 | | | | |
| 1041 a-d | Et | COOMe | T17 | | | | |
| 1042 a-d | Et | COOEt | T1 | | | | |
| 1043 a-d | Et | COOEt | T2 | | | | |
| 1044 a-d | Et | COOEt | T3 | | | | |
| 1045 a-d | Et | COOEt | T9 | | | | |
| 1046 a-d | Et | COOEt | T10 | | | | |
| 1047 a-d | Et | COOEt | T11 | | | | |
| 1048 a-d | Et | COOEt | T14 | | | | |
| 1049 a-d | Et | COOEt | T16 | | | | |
| 1050 a-d | Et | COOEt | T17 | | | | |
| 1051 a-d | Et | SO$_2$Me | T1 | | | | |
| 1052 a-d | Et | SO$_2$Me | T2 | | | | |
| 1053 a-d | Et | SO$_2$Me | T3 | | | | |
| 1054 a-d | Et | SO$_2$Me | T9 | | | | |
| 1055 a-d | Et | SO$_2$Me | T10 | | | | |
| 1056 a-d | Et | SO$_2$Me | T11 | | | | |
| 1057 a-d | Et | SO$_2$Me | T14 | | | | |
| 1058 a-d | Et | SO$_2$Me | T16 | | | | |
| 1059 a-d | Et | SO$_2$Me | T17 | | | | |
| 1060 a-d | Et | SO$_2$Et | T1 | | | | |
| 1061 a-d | Et | SO$_2$Et | T2 | | | | |
| 1062 a-d | Et | SO$_2$Et | T3 | | | | |
| 1063 a-d | Et | SO$_2$Et | T9 | | | | |
| 1064 a-d | Et | SO$_2$Et | T10 | | | | |
| 1065 a-d | Et | SO$_2$Et | T11 | | | | |
| 1066 a-d | Et | SO$_2$Et | T14 | | | | |
| 1067 a-d | Et | SO$_2$Et | T16 | | | | |
| 1068 a-d | Et | SO$_2$Et | T17 | | | | |
| 1069 a-d | H | CO—△ | T1 | Na salt 187–190 | | | |
| 1070 a-d | H | CO—Me | T1 | Na salt 179–181 | | | |
| 1071 a-d | Me | SO$_2$Et | T1 | Na salt 125–135 | | | |
| 1072 a-d | Me | SO$_2$CH$_2$F | T1 | Na salt 170–175 | | | |

TABLE 2

Compounds of the formula (Ie)

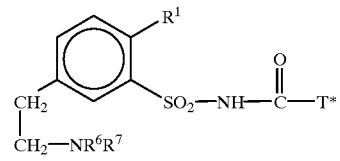

(Ie)

| No. | R¹ | R⁶ | R⁷ | T* | Physical data |
|---|---|---|---|---|---|
| 1e | COO— | H | CHO | T1 | |
| 2e | " | H | CHO | T11 | |
| 3e | " | Me | CHO | T1 | |
| 4e | " | Me | CHO | T11 | |
| 5e | " | H | COCH₃ | T1 | |
| 6e | " | H | COCH₃ | T11 | |
| 7e | " | Me | COCH₃ | T1 | |
| 8e | " | Me | COCH₃ | T11 | |
| 9e | " | H | COCF₃ | T1 | |
| 10e | " | H | COCF₃ | T11 | |
| 11e | " | Me | COCF₃ | T1 | |
| 12e | " | Me | COCF₃ | T11 | |
| 13e | " | H | COOMe | T1 | |
| 14e | " | H | COOMe | T11 | |
| 15e | " | Me | COOMe | T1 | |
| 16e | " | Me | COOMe | T11 | |
| 17e | " | H | COOEt | T1 | |
| 18e | " | H | COOEt | T11 | |
| 19e | " | Me | COOEt | T1 | |
| 20e | " | Me | COOEt | T11 | |
| 21e | " | H | SO₂Me | T1 | |
| 22e | " | H | " | T11 | |
| 23e | " | Me | " | T1 | |
| 24e | " | Me | " | T11 | |
| 25e | " | H | SO₂Et | T1 | |
| 26e | " | H | " | T11 | |
| 27e | " | Me | " | T1 | |
| 28e | " | Me | " | T11 | |
| 29e | COO—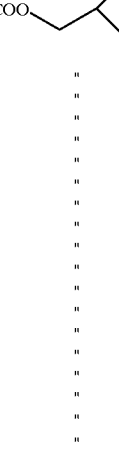 | H | CHO | T1 | |
| 30e | " | H | CHO | T11 | |
| 31e | " | Me | " | T1 | |
| 32e | " | Me | " | T11 | |
| 33e | " | H | COCH₃ | T1 | |
| 34e | " | H | COCH₃ | T11 | |
| 35e | " | Me | " | T1 | |
| 36e | " | Me | " | T11 | |
| 37e | " | H | COCF₃ | T1 | |
| 38e | " | H | COCF₃ | T11 | |
| 39e | " | Me | " | T1 | |
| 40e | " | Me | " | T11 | |
| 41e | " | H | COOMe | T1 | |
| 42e | " | H | COOMe | T11 | |
| 43e | " | Me | " | T1 | |
| 44e | " | Me | " | T11 | |
| 45e | " | H | COOEt | T1 | |
| 46e | " | H | COOEt | T11 | |
| 47e | " | Me | " | T1 | |
| 48e | COO— | Me | COOEt | T11 | |
| 49e | " | H | SO₂Me | T1 | |
| 50e | " | H | SO₂Me | T11 | |
| 51e | " | Me | " | T1 | |
| 52e | " | Me | " | T11 | |
| 53e | " | H | SO₂Et | T1 | |
| 54e | " | H | SO₂Et | T11 | |
| 55e | " | Me | " | T1 | |
| 56e | " | Me | " | T11 | |
| 57e | COO—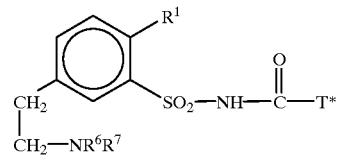 | H | CHO | T1 | |
| 58e | " | H | CHO | T11 | |
| 59e | " | Me | CHO | T1 | |
| 60e | " | Me | " | T11 | |
| 61e | " | H | COMe | T1 | |
| 62e | " | H | COMe | T11 | |
| 63e | " | Me | COMe | T1 | |
| 64e | " | Me | COMe | T11 | |
| 65e | " | H | COCF₃ | T1 | |
| 66e | " | H | COCF₃ | T11 | |
| 67e | " | Me | " | T1 | |
| 68e | " | Me | " | T11 | |
| 69e | " | H | COOMe | T1 | |
| 70e | " | H | COOMe | T11 | |
| 71e | " | Me | " | T1 | |
| 72e | " | Me | " | T11 | |
| 73e | " | H | COOEt | T1 | |
| 74e | " | H | COOEt | T11 | |
| 75e | " | Me | " | T1 | |
| 76e | " | Me | " | T11 | |
| 77e | " | H | SO₂Me | T1 | |
| 78e | " | H | " | T11 | |
| 79e | " | Me | " | T1 | |
| 80e | " | Me | " | T11 | |
| 81e | " | H | SO₂Et | T1 | |
| 82e | " | H | " | T11 | |
| 83e | " | Me | " | T1 | |
| 84e | " | Me | " | T11 | |
| 85e | " | H | SO₂CF₃ | T1 | |
| 86e | " | H | " | T11 | |
| 87e | " | Me | " | T1 | |
| 88e | " | Me | " | T11 | |
| 89e | SO₂n-Pr | H | CHO | T1 | |
| 90e | " | H | CHO | T11 | |
| 91e | " | H | COMe | T1 | |
| 92e | " | H | COMe | T11 | |
| 93e | " | H | COEt | T1 | |
| 94e | " | H | COEt | T11 | |
| 95e | " | H | COCF₃ | T1 | |
| 96e | " | H | COCF₃ | T11 | |
| 97e | " | H | COOMe | T1 | |
| 98e | " | H | COOMe | T11 | |
| 99e | " | H | COOEt | T1 | |
| 100e | " | H | COOEt | T11 | |
| 101e | " | H | SO₂Me | T1 | |
| 102e | " | H | SO₂Me | T11 | |
| 103e | " | H | SO₂Et | T1 | |
| 104e | " | H | SO₂Et | T11 | |
| 105e | " | Me | CHO | T1 | |
| 106e | " | Me | CHO | T11 | |
| 107e | " | Me | COMe | T1 | |
| 108e | " | Me | COMe | T11 | |
| 109e | " | Me | COEt | T1 | |
| 110e | " | Me | COEt | T11 | |
| 111e | " | Me | COCF₃ | T1 | |
| 112e | " | Me | COCF₃ | T11 | |
| 113e | " | Me | COOMe | T1 | |

TABLE 2-continued

Compounds of the formula (Ie)

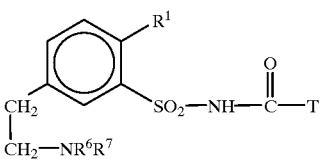

| No. | R¹ | R⁶ | R⁷ | T* | Physical data |
|---|---|---|---|---|---|
| 114e | " | Me | COOMe | T11 | |
| 115e | " | Me | COOEt | T1 | |
| 116e | " | Me | COOEt | T11 | |
| 117e | " | Me | SO₂Me | T1 | |
| 118e | " | Me | SO₂Me | T11 | |
| 119e | " | Me | SO₂Et | T1 | |
| 120e | " | Me | SO₂Et | T11 | |
| 121e | " | Et | CHO | T1 | |
| 122e | " | Et | CHO | T11 | |
| 123e | " | Et | COMe | T1 | |
| 124e | " | Et | COMe | T11 | |
| 125e | " | Et | COEt | T1 | |
| 126e | " | Et | COEt | T11 | |
| 127e | " | Et | COCF₃ | T1 | |
| 128e | " | Et | COCF₃ | T11 | |
| 129e | " | Et | COOMe | T1 | |
| 130e | " | Et | COOMe | T11 | |
| 131e | " | Et | COOEt | T1 | |
| 132e | " | Et | COOEt | T11 | |
| 133e | " | Et | SO₂Me | T1 | |
| 134e | " | Et | SO₂Me | T11 | |
| 135e | " | Et | SO₂Et | T1 | |
| 136e | " | Et | SO₂Et | T11 | |
| 137e | SO₂NMe₂ | H | CHO | T1 | |
| 138e | " | H | CHO | T11 | |
| 139e | " | H | COMe | T1 | |
| 140e | " | H | COMe | T11 | |
| 141e | " | H | COEt | T1 | |
| 142e | " | H | COCF₃ | T1 | |
| 143e | " | H | COCF₃ | T11 | |
| 144e | " | H | COOMe | T1 | |
| 145e | " | H | COOMe | T11 | |
| 146e | " | H | COOEt | T1 | |
| 147e | " | H | COOEt | T11 | |
| 148e | " | H | SO₂Me | T1 | |
| 149e | " | H | SO₂Me | T11 | |
| 150e | " | H | SO₂Et | T1 | |
| 151e | " | H | SO₂Et | T11 | |
| 152e | " | Me | CHO | T1 | |
| 153e | " | Me | CHO | T11 | |
| 154e | " | Me | COMe | T1 | |
| 155e | " | Me | COMe | T11 | |
| 156e | " | Me | COEt | T1 | |
| 157e | " | Me | COEt | T11 | |
| 158e | " | Me | COCF₃ | T1 | |
| 159e | " | Me | COCF₃ | T11 | |
| 160e | " | Me | COOMe | T1 | |
| 161e | " | Me | COOMe | T11 | |
| 162e | " | Me | COOEt | T1 | |
| 163e | " | Me | COOEt | T11 | |
| 164e | " | Me | SO₂Me | T1 | |
| 165e | " | Me | SO₂Me | T11 | |
| 166e | " | Me | SO₂Et | T1 | |
| 167e | " | Me | SO₂Et | T11 | |
| 168e | " | Et | CHO | T1 | |
| 169e | " | Et | CHO | T11 | |
| 170e | " | Et | COMe | T1 | |
| 171e | " | Et | COMe | T11 | |
| 172e | " | Et | COEt | T1 | |
| 173e | " | Et | COEt | T11 | |
| 174e | " | Et | COCF₃ | T1 | |
| 175e | " | Et | COCF₃ | T11 | |
| 176e | " | Et | COOMe | T1 | |
| 177e | " | Et | COOMe | T11 | |

TABLE 2-continued

Compounds of the formula (Ie)

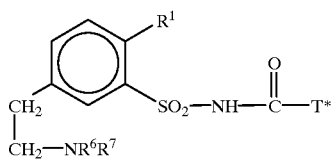

| No. | R¹ | R⁶ | R⁷ | T* | Physical data |
|---|---|---|---|---|---|
| 178e | " | Et | COOEt | T1 | |
| 179e | " | Et | COOEt | T11 | |
| 180e | " | Et | SO₂Me | T1 | |
| 181e | " | Et | SO₂Me | T11 | |
| 182e | " | Et | SO₂Et | T1 | |
| 183e | " | Et | SO₂Et | T11 | |
| 184e | SCH₃ | H | CHO | T1 | |
| 185e | " | H | CHO | T11 | |
| 186e | " | H | COOMe | T1 | |
| 187e | " | H | COOMe | T11 | |
| 188e | " | H | SO₂Me | T1 | |
| 189e | " | H | " | T11 | |
| 190e | " | Me | CHO | T1 | |
| 191e | " | Me | CHO | T11 | |
| 192e | " | Me | COOMe | T1 | |
| 193e | " | Me | COOMe | T11 | |
| 194e | " | Me | SO₂Me | T1 | |
| 195e | " | Me | SO₂Me | T11 | |
| 196e | SC₂H₅ | H | CHO | T1 | |
| 197e | " | H | CHO | T11 | |
| 198e | " | H | COOMe | T1 | |
| 199e | " | H | COOMe | T11 | |
| 200e | " | H | SO₂Me | T1 | |
| 201e | " | H | " | T11 | |
| 202e | " | Me | CHO | T1 | |
| 203e | " | Me | CHO | T11 | |
| 204e | " | Me | COOMe | T1 | |
| 205e | " | Me | COOMe | T11 | |
| 206e | " | Me | SO₂Me | T1 | |
| 207e | " | Me | SO₂Me | T11 | |
| 208e | SO—CH₃ | H | CHO | T1 | |
| 209e | " | H | CHO | T11 | |
| 210e | " | H | COOMe | T1 | |
| 211e | " | H | COOMe | T11 | |
| 212e | " | H | SO₂Me | T1 | |
| 213e | " | H | " | T11 | |
| 214e | " | Me | CHO | T1 | |
| 215e | " | Me | CHO | T11 | |
| 216e | " | Me | COOMe | T1 | |
| 217e | " | Me | COOMe | T11 | |
| 218e | " | Me | SO₂Me | T1 | |
| 219e | " | Me | SO₂Me | T11 | |
| 220e | SO—C₂H₅ | H | CHO | T1 | |
| 221e | " | H | CHO | T11 | |
| 222e | " | H | COOMe | T1 | |
| 223e | " | H | COOMe | T11 | |
| 224e | " | H | SO₂Me | T1 | |
| 225e | " | H | " | T11 | |
| 226e | " | Me | CHO | T1 | |
| 227e | " | Me | CHO | T11 | |
| 228e | " | Me | COOMe | T1 | |
| 229e | " | Me | COOMe | T11 | |
| 230e | " | Me | SO₂Me | T1 | |
| 231e | " | Me | SO₂Me | T11 | |
| 232e | " | Et | CHO | T1 | |
| 233e | " | Et | CHO | T11 | |
| 234e | " | Et | COOCH₃ | T1 | |
| 235e | " | Et | COOCH₃ | T11 | |
| 236e | " | Et | SO₂Me | T1 | |
| 237e | " | Et | SO₂Me | T11 | |
| 238e | CO—NMe₂ | H | CHO | T11 | |
| 239e | " | H | COMe | T1 | |
| 240e | " | H | COMe | T11 | |
| 241e | " | H | COEt | T1 | |

TABLE 2-continued

Compounds of the formula (Ie)

(Ie)

$$\text{structure: benzene ring with } R^1, CH_2-CH_2-NR^6R^7, SO_2-NH-C(=O)-T^*$$

| No. | R$^1$ | R$^6$ | R$^7$ | T* | Physical data |
|---|---|---|---|---|---|
| 242e | " | H | COEt | T11 | |
| 243e | " | H | COCF$_3$ | T1 | |
| 244e | " | H | COCF$_3$ | T11 | |
| 245e | " | H | COOMe | T1 | |
| 246e | " | H | COOMe | T11 | |
| 247e | " | H | COOEt | T1 | |
| 248e | " | H | COOEt | T11 | |
| 249e | " | H | SO$_2$Me | T1 | |
| 250e | " | H | SO$_2$Me | T11 | |
| 251e | " | H | SO$_2$Et | T1 | |
| 252e | " | H | SO$_2$Et | T11 | |
| 253e | " | Me | CHO | T1 | |
| 254e | " | Me | CHO | T11 | |
| 255e | " | Me | COMe | T1 | |
| 256e | " | Me | COMe | T11 | |
| 257e | " | Me | COEt | T1 | |
| 258e | " | Me | COEt | T11 | |
| 260e | " | Me | COCF$_3$ | T1 | |
| 261e | " | Me | COCF$_3$ | T11 | |
| 262e | " | Me | COOMe | T1 | |
| 263e | " | Me | COOMe | T11 | |
| 264e | " | Me | COOEt | T1 | |
| 265e | " | Me | COOEt | T11 | |
| 266e | " | Me | SO$_2$Me | T1 | |
| 267e | " | Me | SO$_2$Me | T11 | |
| 268e | " | Me | SO$_2$Et | T1 | |
| 269e | " | Me | SO$_2$Et | T11 | |
| 270e | " | Et | CHO | T1 | |
| 271e | " | Et | CHO | T11 | |
| 272e | " | Et | COMe | T1 | |
| 273e | " | Et | COMe | T11 | |
| 274e | " | Et | COEt | T1 | |
| 275e | " | Et | COEt | T11 | |
| 276e | " | Et | COCF$_3$ | T1 | |
| 278e | " | Et | COCF$_3$ | T11 | |
| 279e | " | Et | COOMe | T1 | |
| 280e | " | Et | COOMe | T11 | |
| 281e | " | Et | COOEt | T1 | |
| 282e | " | Et | COOEt | T11 | |
| 283e | " | Et | SO$_2$Me | T1 | |
| 284e | " | Et | SO$_2$Me | T11 | |
| 285e | " | Et | SO$_2$Et | T1 | |
| 286e | " | Et | SO$_2$Et | T11 | |
| 287e | " | H | CHO | T1 | |

B. FORMULATION EXAMPLES a) A dust is obtained by mixing 10 parts by weight of a compound of the formula (I) and 90 parts by weight of talc as inert substance and comminuting the mixture in a hammer mill.

b) A wettable powder which is readily dispersible in water is obtained by mixing 25 parts by weight of a compound of the formula (I), 64 parts by weight of kaolin-containing quartz as inert substance, 10 parts by weight of potassium lignosulfonate and 1 part by weight of sodium oleoylmethyltaurinate as wetter and dispersant and grinding the mixture in a pinned-disk mill.

c) A dispersion concentrate which is readily dispersible in water is obtained by mixing 20 parts by weight of a compound of the formula (I) with 6 parts by weight of alkylphenyl polyglycol ether (®Triton X 207), 3 parts by weight of isotridecanol polyglycol ether(8 EO) and 71 parts by weight of paraffinic mineral oil (boiling range for example approx. 255 to above 277° C.) and grinding the mixture in a ball mill to a fineness of below 5 microns.

d) An emulsifiable concentrate is obtained from 15 parts by weight of a compound of the formula (I), 75 parts by weight of cyclohexanone as the solvent and 10 parts by weight of ethoxylated nonylphenol as the emulsifier.

e) Water-dispersible granules are obtained by mixing

| 75 parts by weight | of a compound of the formula (I), |
|---|---|
| 10 parts by weight | of calcium lignosulfonate, |
| 5 parts by weight | of sodium lauryl sulfate, |
| 3 parts by weight | of polyvinyl alcohol and |
| 7 parts by weight | of kaolin, | grinding the mixture on a pinned-disk mill and granulating the powder in a fluidized bed by spraying on water as the granulation liquid.

f) Water-dispersible granules are also obtained by homogenizing and precomminuting, on a colloid mill,

| 25 parts by weight | of a compound of the formula (I), |
|---|---|
| 5 parts by weight | of sodium 2,2'-dinaphthylmethane-6,6'-disulfonate |
| 2 parts by weight | of sodium oleoylmethyltaurinate, |
| 1 part by weight | of polyvinyl alcohol, |
| 17 parts by weight | of calcium carbonate and |
| 50 parts by weight | of water, | subsequently grinding the mixture in a bead mill and atomizing and drying the resulting suspension in a spray tower by means of a single-substance nozzle.

C. BIOLOGICAL EXAMPLES

1. Pre-emergence Effect on Weeds

Seeds or rhizome pieces of monocotyledonous and dicotyledonous weed plants were placed in sandy loam soil in plastic pots and covered with soil. The compounds of the formula (I) according to the invention or salts thereof which were formulated in the form of wettable powders or emulsion concentrates were then applied to the surface of the soil cover in the form of aqueous suspensions or emulsions at an application rate of 600 to 800 l of water/ha (converted), in various dosages.

After the treatment, the pots were placed in a greenhouse and kept under good growth conditions for the weeds. After the test plants had emerged, the damage to the plants or the negative effects on the emergence was scored visually after a test period of 3 to 4 weeks by comparison with untreated controls. As shown by the test results, the compounds according to the invention have a good herbicidal pre-emergence activity against a broad spectrum of grass weeds and dicotyledonous weeds. For example, the compounds of Examples No. 1a, 18a, 69a, 86a, 103a, 137a,154a, 259a, 529a, 530a, 531a, 532a, 549a, 566a, 634a, 668a, 685a, 835a, 1069a, 1070a, 1071a and 1072a, (see Section A, Table 1) have a very good herbicidal activity against harmful plants such as Sinapis alba, Stellaria media, Chrysanthemum segetum and Lolium multiflorum pre-emergence at an application rate of 0.3 kg to 0.005 kg of active substance per hectare.

2. Post-emergence Effect on Weeds

Seeds or rhizome pieces of monocotyledonous and dicotyledonous weeds were placed in sandy loam soil in plastic pots, covered with soil and grown in a greenhouse under good growth conditions. Three weeks after sowing, the test plants were treated at the three-leaf stage. The compounds of the formula (I) according to the invention or salts thereof which were formulated as wettable powders or emulsion concentrates were sprayed, at various dosages, onto the green parts of the plants at an application rate of 600 to 800 l of water/ha (converted). After the test plants had remained in the greenhouse for about 3 to 4 weeks under ideal growth conditions, the effect of the preparations was scored visually by comparison with untreated controls. The agents according to the invention also have a good herbicidal activity post-emergence against a broad spectrum of economically important grass weeds and dicotyledonous weeds. For example, the compounds of Examples No. 1a, 18a, 69a, 86a, 103a, 137a, 154a, 259a, 529a, 530a, 531a, 532a, 549a, 566a, 634a, 668a, 685a, 835a, 1069a, 1070a, 1071a and 1072a, (see Section A, Table 1) have a very good herbicidal activity against harmful plants such as Sinapis alba, Stellaria media, Chrysanthemum segetum and Lolium multiflorum post-emergence at an application rate of 0.3 kg to 0.005 kg of active substance per hectare.

3. Tolerance by Crop Plants

In further greenhouse experiments, seeds of a substantial number of crop plants and weeds were placed in sandy loam soil and covered with soil.

Some of the pots were treated immediately as described under 1, and the remaining pots were placed in a greenhouse until the plants had developed two to three true leaves and then sprayed with various dosages of the substances of the formula (I) according to the invention or salts thereof, as described under 2.

Visual scoring four to five weeks after the application and after the plants had been in the greenhouse revealed that the compounds according to the invention did not inflict any damage to dicotyledonous crops such as, for example, soya, cotton, oil seed rape, sugar beet and potatoes when used pre- and post-emergence, even when high dosages of active ingredient were used. Moreover, some substances also left Gramineae crops such as for example, barley, wheat, rye, sorghum species, maize or rice unharmed. The compounds of the formula (I) or salts thereof thus have a high selectivity when used for controlling undesired plant growth in agricultural crops.

We claim:

1. A compound of the formula (1) or a salt thereof

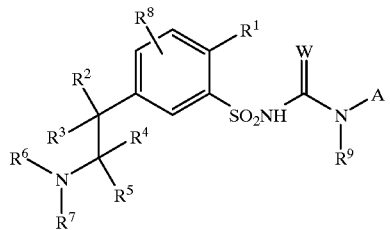

in which $R^1$ is an acyl radical of the formula $S(O)_n$—$R^{10}$ or CO—Q—$R^{11}$, $R^2$, $R^3$, $R^4$, $R^5$ are identical or different radicals selected from the group consisting of H, (1–6)alkyl, (1–4) alkoxy, (1–4)haloalkyl, (1–4)haloalkoxy and halogen, $R^6$ is H, OH, formyl, a radical of the formula R, R—O—, R—CO, R—O—CO—, R—$SO_2$—, R—SO— or RR°$NSO_2$—, in which each of the radicals R and R° is a hydrocarbon radical which is unsubstituted or substituted, and, $R^7$ is CHO, [(1–6)alkyl]carbonyl, [(2–6)alkenyl]carbonyl, [(2–6)alkynyl]carbonyl, (1–6)alkylsulfonyl, (2–6) alkenylsulfonyl, (2–6)alkynylsulfonyl, [(3–6) cycloalkyl]carbonyl, [(5–6)cycloalkenyl]carbonyl, [(3–6)cycloalkyl]-sulfonyl, (5–6)cycloalkenylsulfonyl, each of the 10 last-mentioned radicals being unsubstituted or substituted by one or more radicals selected from the group consisting of halogen, (1–4)alkoxy, (1–4)alkylthio, (1–4)alkyl sulfonyl, (1–4)alkylsulfinyl, (1–4)alkylcarbonyl, [(1–4)alkoxy]carbonyl, [(1–4) alkyl]carbonyloxy and CN and, in the case of cyclic radicals, also by (1–4)alkyl and (1–4)haloalkyl, or phenylcarbonyl or phenylsulfonyl, each of the two last-mentioned radicals being unsubstituted or substituted in the phenyl ring by one or more radicals selected from the group consisting of halogen, CN, $NO_2$, (1–4)alkyl, (1–4)haloalkyl, (1–4)alkoxy and (1–4)haloalkoxy, or mono- or di[(1–4)alkyl]aminosulfonyl which is unsubstituted or substituted in the alkyl moiety by one or more radicals selected from the group consisting of halogen, (1–4)alkoxy, (1–4)alkylthio, (1–4) alkylsulfinyl, (1–4)alkylsulfonyl, [(1–4)alkyl] carbonyl, [(1–4)alkyl]carbonyloxy, [(1–4)alkoxy] carbonyl and CN, or a group of the formula COCOR' in which R'=H, OH, (1–4)alkoxy or (1–4)alkyl, or a group of the formula

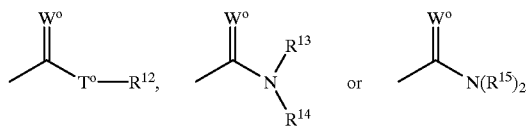

or $NR^6R^7$ together are a chain of the formula —$(CH_2)_{m1}B^1$ of —$B^1$—$(CH_2)_{m2}$—$B^2$—, where m1 is 3, 4 or 5 and m2 is 2, 3 or 4

$B^1$ is $SO_2$ or CO, $B^2$ is $SO_2$ or CO

W is an oxygen or sulfur atom, $W°$ is O or S, $T°$ is O or S, $R^8$ is H, (1–6)alkyl, (2–6)alkenyl, (1–6)alkoxy, (1–4) alkylthio, [(1–4)alkyl]-carbonyl or [(1–4)alkoxy] carbonyl, each of the six last-mentioned radicals being unsubstituted or substituted by one or more radicals selected from the group consisting of halogen, (1–4)alkoxy, (1–4)alkylthio and CN, or is halogen, $NO_2$, CN, $NH_2$ or mono- or disubstituted amino, $R^9$ is H or (1–6)alkyl, $R^{10}$ is $NH_2$, mono- or disubstituted amino or a hydrocarbon radical which is unsubstituted or substituted, and which, n is the number 0, 1 or 2, with the exception of the case $R^{10}$=$NH_2$ or mono- or disubstituted amino, in which case n=2, $R^{11}$ is H or a hydrocarbon radical which is unsubstituted or substituted, or is a heterocycle wherein said heterocycle is an aliphatic heterocyclyl radical having 3 to 7 ring atoms or a heteroaromatic radical having 5 to 6 ring atoms, wherein 1 of the ring atoms is a heteroatom selected from the group consisting of N, O, and S, or is pyrimidinyl, pyridazinyl, pyrazinyl, thiazolyl, oxazol, pyrazolyl, imidazol, piperidinyl, piperazinyl, dioxolanyl, or morpholinyl, wherein said groups are unsubstituted or substituted, and, $R^{12}$ is (1–4)alkyl, (3–4)alkenyl or (3–4)alkynyl, each of the three last-mentioned radicals being unsubstituted or substituted by one or more radicals selected from the group consisting of halogen, (1–4)alkoxy, (1–4)alkylthio, [(1–4)alkyl]carbonyl and [(1–4)alkoxy]carbonyl, $R^{13}$, $R^{14}$ independently of one another are H, (1–4)alkyl, (3–4)alkenyl or (3–4)alkynyl, each of the three last-mentioned radicals being unsubstituted or substituted by one or more of the radicals selected from the group consisting of halogen, (1–4)alkoxy, (1–4)alkylthio, [(1–4)alkyl]carbonyl and [(1–4)alkoxy]carbonyl, the radicals $R^{15}$ together with the nitrogen atom are a heterocyclic ring which has 5 or 6 ring members, may contain one further hetero atom selected from the group consisting of N, O and S at the oxidation levels which are possible and which is unsubstituted or substituted by (1–4)alkyl or the oxo group, or which is benzo-fused, Q is an oxygen or sulfur atom or a group of the formula —NR'— in which R' is H or a hydrocarbon radical which is unsubstituted or substituted, or is an acyl radical, A is a radical of the formula

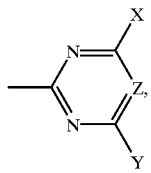

one of the radicals X and Y is hydrogen, halogen, (1–3)alkyl or (1–3)alkoxy, each of the two last-mentioned radicals being unsubstituted or substituted by one or more radicals selected from the group consisting of halogen, (1–3)alkoxy and (1–3)alkylthio, and the other of the radicals X and Y is hydrogen, halogen, (1–3)alkyl, (1–3)alkoxy or (1–3)alkylthio, each of the three last-mentioned alkyl containing radicals being unsubstituted or substituted by one or more radicals selected from the group consisting of halogen, (1–3)alkoxy and (1–3)alkylthio, or is a radical of the formula $NR^aR^b$, (3–6)cycloalkyl, (2–4)alkenyl, (2–4)alkynyl, (3–4)alkenyloxy or (3–4)alkynyloxy, Z is CH, $R^a$ and $R^b$ independently of one another are H, (1–4)alkyl or (2–4)alkenyl, wherein the hydrocarbon radical is defined as alkyl, alkenyl, alkynyl or aryl having up to 12 carbon atoms, and when substituted, the substituents are halogen, (1–4)alkoxy, (1–4)haloalkoxy, (1–4)alkylthio, hydroxy, amino, nitro, (1–4)carboxy, cyano, azido, [(1–4)alkoxy]carbonyl, [(1–4)alkyl]carbonyl, formyl, carbamoyl, mono(1–4)alkylaminocarbonyl, di(1–4)alkylaminocarbonyl, acylamino, mono(1–4)alkylamino, (1–4)alkylsulfinyl, (1–4)haloalkylsulfinyl, (1–4)alkylsulfonyl, (1–4)haloalkylsulfonyl, (2–4)alkenyl, (2–4)alkynyl, (2–4)alkenyloxy, (2–4)alkynyloxy, mono- or disubstituted amino, unsubstituted or N-substituted hydroxylamino, or unsubstituted or N-substituted hydrazino, wherein the substitution on the last 4 mentioned substituted radicals are selected from the groups consisting of (1–4)alkyl, (1–4)alkoxy, (1–4)acyl, and (6–12)aryl, wherein the substituents on the aryl or heterocyclic groups are those identified above for the hydrocarbon radical or when an aliphatic heterocycle radical are also oxo, and wherein the substitutents on the mono- and di-substituted amino radicals are selected from the group consisting of (1–4)alkyl, (1–4)alkoxy, (1–4)acyl and (6–12)aryl.

2. A compound or salt thereof as claimed in claim 1, wherein $R^1$ is $S(O)_n$—$R^{10}$ or $COQR^{11}$, $R^2$, $R^3$, $R^4$, $R^5$ independently of one another are H or (1–4)alkyl, $R^6$ is H, OH, formyl, (1–6)alkyl, (2–6)alkenyl, (2–4)alkynyl, (1–6)alkoxy, (2–6)alkenyloxy, (2–6)alkynyloxy, [(1–6)alkyl]carbonyl, [(2–6)alkenyl]carbonyl, [(2–6)alkynyl]carbonyl, (1–4)alkylsulfonyl, (2–6)alkenylsulfonyl, (2–6)alkynylsulfonyl, (3–6)cycloalkyl, (5–6)cycloalkenyl, [(3–6)cycloalkyl]carbonyl, [(5–6)cycloalkenyl]carbonyl, [(3–6)cycloalkyl]sulfonyl, [(5–6)cycloalkenyl]sulfonyl, each of the 18 last-mentioned radicals being unsubstituted or substituted by one or more radicals selected from the group consisting of halogen, (1–4)alkoxy, (1–4)alkylthio, (1–4)alkylsulfonyl, (1–4)alkylsulfonyl, [(1–4)alkoxyl]carbonyl, [(1–4)alkyl]carbonyl, [(1–4)alkyl]carbonyloxy and CN and, in the case of cyclic radicals, also by (1–4)alkyl and (1–4)haloalkyl, or phenylcarbonyl or phenylsulfonyl, each of the two last-mentioned radicals being unsubstituted or substituted in the phenyl ring by one or more radicals selected from the group consisting of halogen, CN, $NO_2$, (1–4)alkyl, (1–4)haloalkyl, (1–4)alkoxy and (1–4)haloalkoxy, $R^7$ is CHO, [(1–6)alkyl]carbonyl, [(2–6)alkenyl]carbonyl, [(2–6)alkynyl]-carbonyl, (1–6)alkylsulfonyl, (2–6)alkenylsulfonyl, (2–6)alkynylsulfonyl, [(3–6)cycloalkyl]carbonyl, [(5–6)cycloalkenyl]carbonyl, [(3–6)cycloalkyl]-sulfonyl, (5–6)cycloalkenylsulfonyl, each of the 10 last-mentioned radicals being unsubstituted or substituted by one or more radicals selected from the group consisting of halogen, (1–4)alkoxy, (1–4)alkylthio, (1–4)alkyl sulfonyl, (1–4)alkylsulfinyl, (1–4)alkylcarbonyl, [(1–4)alkoxy]-carbonyl, [(1–4)alkyl]carbonyloxy and CN and, in the case of cyclic radicals, also by (1–4)alkyl and (1–4)haloalkyl, or phenylcarbonyl or phenylsulfonyl, each of the two last-mentioned radicals being unsubstituted or substituted in the phenyl ring by one or more radicals selected from the group consisting of halogen, CN, $NO_2$, (1–4)alkyl, (1–4)haloalkyl, (1–4)alkoxy and (1–4)haloalkoxy, or mono- or di[(1–4)alkyl]aminosulfonyl which is unsubstituted or substituted in the alkyl moiety by one or more radicals selected from the group consisting of halogen, (1–4)alkoxy, (1–4)alkylthio, (1–4)alkylsulfinyl, (1–4)alkylsulfonyl, [(1–4)alkyl]

carbonyl, [(1–4)alkyl]carbonyloxy, [(1–4)alkoxy] carbonyl and CN, or a group of the formula COCOR' in which R'=H, OH, (1–4)alkoxy or (1–4)alkyl, or a group of the formula

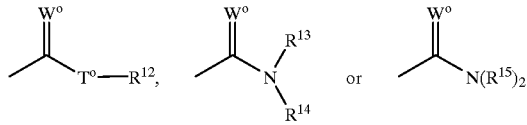

W, W° are an oxygen atom or a sulfur atom,

Q is O, S or $NR^{16}$,

T° is O or S, $R^8$ is H, (1–4)alkyl, (1–4)alkoxy, (1–4)alkylthio, [(1–4)alkyl]carbonyl or
 [(1–4)alkoxy]carbonyl, each of the last-mentioned 5 radicals being unsubstituted or substituted in the alkyl moiety by one or more halogen atoms, or is halogen, $NO_2$, CN or mono- or di(1–4)alkylamino, $R^9$ is H or $CH_3$, $R^{10}$ is $NR^{17}R^{18}$, (1–6)alkyl, (2–6)alkenyl, (2–6)alkynyl, (3–6)cycloalkyl, (5–6)cycloalkenyl or phenyl, each of the last-mentioned 6 radicals being unsubstituted or substituted by one or more radicals selected from the group consisting of halogen, CN, (1–4)alkoxy, (1–4)alkylthio, (1–4)alkylsulfinyl, (1–4)alkylsulfonyl, [(1–4)alkyl]carbonyl, [(1–4)alkoxy]carbonyl and [(1–4)alkyl]carbonyloxy, n is the number 0, 1 or 2, unless $R^{10}=NR^{17}R^{18}$, in which case n=2, and $R^{11}$ is H, (1–6)alkyl, (2–6)alkenyl, (2–6)alkynyl, (3–6)cycloalkyl, (5–6)cycloalkenyl or phenyl, each of the last-mentioned 6 radicals being unsubstituted or substituted by one or more radicals selected from the group consisting of halogen, CN, (1–4)alkoxy, (1–4)alkylthio, (1–4)alkylsulfinyl, (1–4)alkylsulfonyl, [(1–4)alkyl]carbonyl, [(1–4)alkoxy]carbonyl and [(1–4)alkyl]carbonyloxy, and, in the case of cyclic radicals, also by (1–4)alkyl and (1–4)haloalkyl, or is a radical of the heterocyclyl or heterocyclyl(1–4)alkyl which has 3 to 7 ring atoms and 1 of the ring atoms is selected from the group consisting of N, O and S, or is pyrimidinyl, pyridazinyl, pyrazinyl, thiazolyl, oxazol, pyrazolyl, imidazol, piperidinyl, piperazinyl, dioxolanyl, or morpholinyl, wherein said groups are unsubstituted or substituted, and, $R^{12}$ is (1–4)alkyl, (3–4)alkenyl or (3–4)alkynyl, each of the three last-mentioned radicals being unsubstituted or substituted by one or more radicals selected from the group consisting of halogen, (1–4)alkoxy, (1–4)alkylthio, [(1–4)alkyl]carbonyl and [(1–4)alkoxy]carbonyl, $R^{13}$, $R^{14}$ independently of one another are H, (1–4)alkyl, (3–4)alkenyl or (3–4)alkynyl, each of the three last-mentioned radicals being unsubstituted or substituted by one or more of the radicals selected from the group consisting of halogen, (1–4)alkoxy, (1–4)alkylthio, [(1–4)alkyl]carbonyl and [(1–4)alkoxy]carbonyl, the radicals $R^{15}$ together with the nitrogen atom are a heterocyclic ring which has 5 or 6 ring members, may contain one farther hetero atoms selected from the group consisting of N, O and S at the oxidation levels which are possible and which is unsubstituted or substituted by (1–4)alkyl or the oxo group, or which is benzo-fused, $R^{16}$ is H, (1–4)alkyl, (3–4)alkenyl or (3–4)alkynyl, each of the three last-mentioned radicals being unsubstituted or substituted by one or more radicals selected from the group consisting of halogen, (1–4)alkoxy and (1–4) alkylthio, $R^{17}$ is H, (1–4)alkyl or (1–4)alkoxy, and $R^{18}$ is H or (1–4)alkyl.

3. A compound or salt thereof as claimed in claim 1, wherein $R^1$ is $S(O)_n—R^{10}$ or $COQR^{11}$, $R^2$, $R^3$, $R^4$, $R^5$ independently of one another are H or (1–4)alkyl, $R^6$ and $R^7$ together are a chain of the formula $(—CH_2)_{m1}B^1—$ or $—B^1—(CH_2)_{m2}B^2—$, the chain being unsubstituted or substituted by one or more (1–3)alkyl radicals or halogen and m1 is 3, 4 or 5 and m2 is 2, 3 or 4, and W, W° are an oxygen atom or a sulfur atom, $B^1$, $B^2$ independently of one another are $SO_2$ or CO, Q is O, S or $NR^{16}$, T° is O or S, $R^8$ is H, (1–4)alkyl, (1–4)alkoxy, (1–4)alkylthio, [(1–4)alkyl]carbonyl or [(1–4)alkoxy]carbonyl, each of the last-mentioned 5 radicals being unsubstituted or substituted in the alkyl moiety by one or more halogen atoms, or is halogen, $NO_2$, CN or mono- or di(1–4)alkylamino, $R^9$ is H or $CH_3$, $R^{10}$ is $NR^{17}R^{18}$, (1–6)alkyl, (2–6)alkenyl, (2–6)alkynyl, (3–6)cycloalkyl, (5–6)cycloalkenyl or phenyl, each of the last-mentioned 6 radicals being unsubstituted or substituted by one or more radicals selected from the group consisting of halogen, CN, (1–4)alkoxy, (1–4)alkylthio, (1–4)alkylsulfinyl, (1–4)alkylsulfonyl, [(1–4)alkyl]carbonyl, [(1–4)alkoxy]carbonyl and [(1–4)alkyl]carbonyloxy, n is the number 0, 1 or 2, unless $R^{10}=N^{17}R^{18}$, in which case n=2, and $R^{11}$ is H, (1–6)alkyl, (2–6)alkenyl, (2–6)alkynyl, (3–6)cycloalkyl, (5–6)cycloalkenyl or phenyl, each of the last-mentioned 6 radicals being unsubstituted or substituted by one or more radicals selected from the group consisting of halogen, CN, (1–4)alkoxy, (1–4)alkylthio, (1–4)alkylsulfinyl, (1–4)alkylsulfonyl, [(1–4)alkyl]carbonyl, [(1–4)alkoxy]carbonyl and [(1–4)alkyl]carbonyloxy, and, in the case of cyclic radicals, also by (1–4)alkyl and (1–4)haloalkyl, or is a radical of the heterocyclyl or heterocyclyl(1–4)alkyl type which has 3 to 7 ring atoms and 1 of the ring atoms is selected from the group consisting of N, O and S, or is pyrimidinyl, pyridazinyl, pyrazinyl, thiazolyl, oxazol, pyrazolyl, imidazol, piperidinyl, piperazinyl, dioxolanyl, or morpholinyl, wherein said groups are unsubstituted or substituted, and, $R^{12}$ is (1–4)alkyl, (3–4)alkenyl or (3–4)alkynyl, each of the three last-mentioned radicals being unsubstituted or substituted by one or more radicals selected from the group consisting of halogen, (1–4)alkoxy, (1–4)alkylthio, [(1–4)alkyl]carbonyl and [(1–4)alkoxy]carbonyl, $R^{13}$, $R^{14}$ independently of one another are H, (1–4)alkyl, (3–4)alkenyl or (3–4)alkynyl, each of the three last-mentioned radicals being unsubstituted or substituted by one or more of the radicals selected from the group consisting of halogen, (1–4)alkoxy, (1–4)alkylthio, [(1–4)alkyl]carbonyl and [(1–4)alkoxy]carbonyl, the radicals $R^{15}$ together with the nitrogen atom are a heterocyclic ring which has 5 or 6 ring members, may contain one further hetero atoms selected from the group consisting of N, O and S at the oxidation levels which are possible and which is unsubstituted or substituted by (1–4)alkyl or the oxo group, or which is benzo-fused, $R^{16}$ is H, (1–4)alkyl, (3–4)alkenyl or (3–4)alkynyl, each of the three last-mentioned radicals being unsubstituted or substituted by one or more radicals selected from the group consisting of halogen, (1–4)alkoxy and (1–4) alkylthio, $R^{17}$ is H, (1–4)alkyl or (1–4)alkoxy, and $R^{18}$ is H or (1–4)alkyl.

4. A compound or salt thereof as claimed in claim 1, wherein $R^1$ is $S(O)_n$—$R^{10}$ or CO—Q—$R^{11}$, $R^2$, $R^3$, $R^4$, $R^5$ independently of one another are H or (1–4)alkyl, $R^6$ is H, OH, formyl, (1–6)alkyl, (2–6)alkenyl, (2–4) alkynyl, (1–6)alkoxy, (2–6)alkenyloxy, (2–6) alkynyloxy, [(1–6)alkyl]carbonyl, [(2–6)alkenyl] carbonyl, [(2–6)alkynyl]carbonyl, (1–4)alkylsulfonyl, (2–6)alkenylsulfonyl, (2–6)alkynylsulfonyl, (3–6) cycloalkyl, (5–6)cycloalkenyl, [(3–6)cycloalkyl]-carbonyl, [(5–6)cycloalkenyl]carbonyl, [(3–6) cycloalkyl]sulfonyl, [(5–6)cycloalkenyl]sulfonyl, each of the 18 last-mentioned radicals being unsubstituted or substituted by one or more radicals selected from the group consisting of halogen, (1–4)alkoxy, (1–4) alkylthio, (1–4)alkylsulfinyl, (1–4)alkylsulfonyl, [(1–4)alkoxyl]carbonyl, [(1–4)alkyl]carbonyl, [(1–4) alkyl]carbonyloxy and CN and, in the case of cyclic radicals, also by (1–4)alkyl and (1–4)haloalkyl, or phenylcarbonyl or phenylsulfonyl, each of the two last-mentioned radicals being unsubstituted or substituted in the phenyl ring by one or more radicals selected from the group consisting of halogen, CN, $NO_2$, (1–4)alkyl, (1–4)haloalkyl, (1–4)alkoxy and (1–4)haloalkoxy, $R^7$ is CHO, [(1–6)alkyl]carbonyl, [(2–6)alkenyl]carbonyl, [(2–6)alkynyl]-carbonyl, (1–6)alkylsulfonyl, (2–6) alkenylsulfonyl, (2–6)alkynylsulfonyl, [(3–6) cycloalkyl]carbonyl, [(5–6)cycloalkenyl]carbonyl, [(3–6)cycloalkyl]-sulfonyl, (5–6)cycloalkenylsulfonyl, each of the 10 last-mentioned radicals being unsubstituted or substituted by one or more radicals selected from the group consisting of halogen, (1–4)alkoxy, (1–4)alkylthio, (1–4)alkyl sulfonyl, (1–4)alkylsulfinyl, (1–4)alkylcarbonyl, [(1–4)alkoxy]-carbonyl, [(1–4) alkyl]carbonyloxy and CN and, in the case of cyclic radicals, also by (1–4)alkyl and (1–4)haloalkyl, or phenylcarbonyl or phenylsulfonyl, each of the two last-mentioned radicals being unsubstituted or substituted in the phenyl ring by one or more radicals selected from the group consisting of halogen, CN, $NO_2$, (1–4)alkyl, (1–4)haloalkyl, (1–4)alkoxy and (1–4)haloalkoxy, or mono- or di[(1–4)alkyl]aminosulfonyl which is unsubstituted or substituted in the alkyl moiety by one or more radicals selected from the group consisting of halogen, (1–4)alkoxy, (1–4)alkylthio, (1–4) alkylsulfinyl, (1–4)alkylsulfonyl, [(1–4)alkyl] carbonyl, [(1–4)alkyl]carbonyloxy, [(1–4)alkoxy] carbonyl and CN, or a group of the formula COCOR' in which R'=H, OH, (1–4)alkoxy or (1–4)alkyl, or a group of the formula

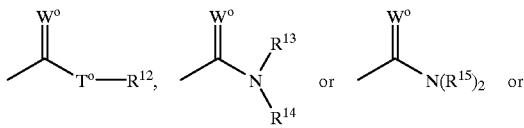

$R^6$ and $R^7$ together are a chain of the formula (—$CH_2$)$_{m1}B^1$— or —$B^1$—($CH_2$)$_{m2}B^2$—, the chain being unsubstituted or substituted buy one or more (1–3)alkyl radicals or halogens and m1 is 3, 4 or 5 and m2 is 2, 3, or 4, and W, $W^0$ are an oxygen atom or a sulfur atom, Q is O, S or $NR^{16}$, $T^0$ is O or S, $R^8$ is H, (1–4)alkyl, (1–4)alkoxy, (1–4)alkylthio, [(1–4) alkyl]carbonyl or [(1–4)alkoxy]carbonyl, each of the last-mentioned 5 radicals being unsubstituted or substituted in the alkyl moiety by one or more halogen atoms, or is halogen, $NO_2$, CN or mono- or di(1–4) alkylamino, $R^9$ is H or $CH_3$, $R^{10}$ is $N^{17}R^{18}$, (1–6)alkyl, (2–6)alkenyl, (2–6)alkynyl, (3–6)cycloalkyl, (5–6)cycloalkenyl or phenyl, each of the last-mentioned 6 radicals being unsubstituted or substituted by one or more radicals selected from the group consisting of halogen, CN, (1–4)alkoxy, (1–4)alkylthio, (1–4)alkylsulfinyl, (1–4) alkylsulfonyl, [(1–4)alkyl]carbonyl, [(1–4)alkoxy] carbonyl and [(1–4)alkyl]carbonyloxy, n is the number 0, 1 or 2, unless $R^{10}$=$NR^{17}R^{18}$, in which case n=2, and $R^{11}$ is H, (1–6)alkyl, (2–6)alkenyl, (2–6)alkynyl, (3–6) cycloalkyl, (5–6)cycloalkenyl or phenyl, each of the last-mentioned 6 radicals being unsubstituted or substituted by one or more radicals selected from the group consisting of halogen, CN, (1–4)alkoxy, (1–4) alkylthio, (1–4)alkylsulfinyl, (1–4)alkylsulfonyl, [(1–4)alkyl]carbonyl, [(1–4)alkoxy]carbonyl and [(1–4)alkyl]carbonyloxy, and, in the case of cyclic radicals, also by (1–4)alkyl and (1–4)haloalkyl, or is a radical of the heterocyclyl or heterocyclyl(1–4) alkyl which has 3 to 7 ring atoms and 1 of the ring atoms is a hetero atom selected from the group consisting of N, O and S, or is piperidinyl, piperazinyl, dioxolanyl or morpholinyl $R^{12}$ is (1–4)alkyl, (3–4)alkenyl or (3–4)alkynyl, each of the three last-mentioned radicals being unsubstituted or substituted by one or more radicals selected from the group consisting of halogen, (1–4)alkoxy, (1–4) alkylthio, [(1–4)alkyl]carbonyl and [(1–4)alkoxy] carbonyl, $R^{13}$, $R^{14}$ independently of one another are H, (1–4)alkyl, (3–4)alkenyl or (3–4)alkynyl, each of the three last-mentioned radicals being unsubstituted or substituted by one or more of the radicals selected from the group consisting of halogen, (1–4)alkoxy, (1–4)alkylthio, [(1–4)alkyl]carbonyl and [(1–4)alkoxy]carbonyl, the radicals $R^{15}$ together with the nitrogen atom are a heterocyclic ring which has 5 or 6 ring members, may contain one further hetero atom selected from the group consisting of N, O and S at the oxidation levels which are possible and which is unsubstituted or substituted by (1–4)alkyl or the oxo group, or which is benzo-fused, $R^{16}$ is H, (1–4)alkyl, (3–4)alkenyl or (3–4)alkynyl, each of the three last-mentioned radicals being unsubstituted or substituted by one or more radicals selected from the group consisting of halogen, (1–4)alkoxy and (1–4)alkylthio, $R^{17}$ is H, (1–4)alkyl or (1–4)alkoxy, and $R^{18}$ is H or (1–4)alkyl.

5. A compound of salt thereof as claimed in claim 1, wherein $R^1$ is $S(O)_n-R^{10}$ or $CO-Q-R^{11}$, n is the number 1, 2 or 2, with the exception of the case $R^{10}=NR^{17}R^{18}$, in which case n=2, $R^6$ is H or (1–4)alkyl which is substituted by one or more halogen atoms or by one or more radicals selected from the group (1–4)alkoxy and (1–4)alkylthio, $R^7$ is formyl, [(1–6)alkyl]carbonyl, [(2–4)alkenyl] carbonyl, [(2–4)alkynyl]-carbonyl, [(3–6)cycloalkyl] carbonyl or (1–6)alkylsulfonyl, each of the 5 last-mentioned radicals being unsubstituted or substituted by one or more radicals selected from the group consisting of halogen, (1–4)alkoxy, (1–4)alkylthio, (1–4) alkylsulfonyl, [(1–4)alkyl]carbonyl, [(1–4)alkoxy]-carbonyl, [(1–4)alkyl]carbonyloxy and CN and, in the case of cyclic radicals, also (1–4)alkyl and (1–4) haloalkyl, or phenylcarbonyl or phenylsulfonyl, each of the two last-mentioned radicals being unsubstituted or substituted by one or more radicals selected from the group consisting of halogen, CN, $SO_2$, (1–4)alkyl, (1–4)haloalkyl, (1–4)alkoxy and (1–4)haloalkoxy, or mono- or di[(1–4)alkyl]aminosulfonyl, or a group of the formula —CO—CO—R' in which R' is (1–4) alkoxy, or a group of the formula $—CW^o—R^{12}$, $—CW^o—NR^{13}R^{14}$ or $—CW^o—N(R^{15})_2$ or $R^6$ and $R^7$ together are a chain of the formula $(—CH_2)_{m1}B^1—$ or $—B^1—(CH_2)_{m2}B^2—$, m1 being 3, 4 or 5 and m2 being 2, 3, or 4, and W, $W^o$ in each case independently are an oxygen atom or a sulfur atom, $T^o$ is an oxygen or sulfur atom, $B^1$ is $SO_2$ or CO, $B^2$ is $SO_2$ or CO, Q is O, S or $NR^{16}$, $R^8$ is a hydrogen atom, $R^9$ is H or $CH_3$, $R^{10}$ is $NR^{17}R^{18}$, (1–6)alkyl, or (3–6)cycloalkyl, $R^{11}$ is H, (1–6)alkyl, (3–6)cycloalkyl or a radical of the formulae A-1 to A-6,

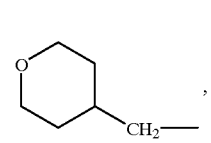

A-1

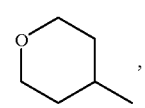

A-2

A-3

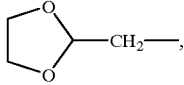

A-4

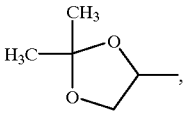

A-5

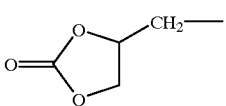

A-6

$R^{12}$ is (1–4)alkyl, or (1–4)haloalkyl, $R^{13}$, $R^{14}$ independently of one another are H or (1–4) alkyl, the radicals $R^{15}$ together are a divalent chain of the formula $—(CH_2)_{m3}—$ in which m3 is 3, 4 or 5, or of the formula $—CH_2CH_2—O—CH_2CH_2—$, $R^{16}$ is H or (1–4)alkyl, $R^{17}$ is H or (1–4)alkyl and $R^{18}$ is H or (1–4)alkyl.

6. A compound or salt thereof as claimed in claim 1, wherein $R^6$ is H or (1–4)alkyl, $R^7$ CHO, [(1–6)alkyl]carbonyl, [(1–4)haloalkyl]carbonyl, [(1–4)alkoxy(1–4)alkyl]carbonyl, [(3–6)cycloalkyl] carbonyl, phenylcarbonyl which is unsubstituted or substituted by one or more radicals selected form the group consisting of halogen, CN, $NO_2$, (1–4)alkyl, (1–4)haloalkyl, (1–4)alkoxy and (1–4)haloalkoxy, or is phenylsulfonyl which is unsubstituted or substituted by one or more radicals selected from the group consisting of (1–4)alkyl and (1–4)alkoxy, or is mono- or di[(1–4) alkyl]aminosulfonyl, (1–6)alkylsulfonyl, (1–4) haloalkylsulfonyl or a group of the formula $—CW^o—R^{12}$ or $—CW^o—NR^{13}R^{14}$ W, $W^o$ independently of one another are in each case O or S, $T^o$ is O or S, Q is O, S or $NR^{16}$, $R^{10}$ is $NR^{17}R^{18}$, (1–4)alkyl, or (3–6)cycloalkyl, $R^{11}$ is H or (1–4)alkyl $R^{12}$ is (1–4)alkyl, $R^{13}$, $R^{14}$ independently of one another are H or (1–4) alkyl, $R^{16}$ is H or (1–3)alkyl, $R^{17}$ is (1–4)alkyl and $R^{18}$ is H or (1–4)alkyl.

7. A compound of the formula (I) as claimed in claim 1 or a salt thereof, wherein $R^7$ is

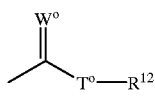 or 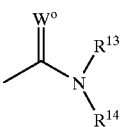

wherein
$W^0$ is O,
$T^0$ is O,
$R^{12}$ is (1–4)alkyl
$R^{13}$, $R^{14}$ are independently H or (1–4)alkyl.

8. A compound of the formula (I) as claimed in claim 1 or a salt thereof, wherein
$R^1$ is CO—O—CH$_3$,
$R^2$, $R^3$, $R^4$, $R^5$ are H,
$R^6$ is H,
$R^7$ is —SO$_2$CH$_3$,
W is an oxygen atom,
$R^9$ is hydrogen, and
X and Y are —OCH$_3$.

9. A herbicidal or plant-growth-regulating composition which comprises on or more compounds of the formula (I) or salts thereof as claimed in claim 1 and formulation auxiliaries conventionally used in crop protection.

10. A method of controlling harmful plants or for regulating the growth of plants, which comprises applying an effective amount of one or more compounds of the formula (I) or salts thereof as claimed in claim 1 to the plants, seeds of the plant or the area under cultivation.

* * * * *